(12) United States Patent
Stitz

(10) Patent No.: US 8,663,989 B2
(45) Date of Patent: Mar. 4, 2014

(54) RETROVIRAL VECTOR PARTICLES AND METHODS FOR THEIR GENERATION AND USE

(75) Inventor: Jörn Stitz, Basel (CH)

(73) Assignee: 4-Antibody AG, Basel (CH)

( * ) Notice: Subject to any disclaimer, the term of this patent is extended or adjusted under 35 U.S.C. 154(b) by 0 days.

(21) Appl. No.: 13/511,186

(22) PCT Filed: Nov. 22, 2010

(86) PCT No.: PCT/EP2010/067946
§ 371 (c)(1),
(2), (4) Date: May 22, 2012

(87) PCT Pub. No.: WO2011/061336
PCT Pub. Date: May 26, 2011

(65) Prior Publication Data
US 2012/0258494 A1    Oct. 11, 2012

Related U.S. Application Data

(60) Provisional application No. 61/263,539, filed on Nov. 23, 2009.

(30) Foreign Application Priority Data

Nov. 23, 2009   (EP) ..................... 09176789

(51) Int. Cl.

| | |
|---|---|
| C12N 15/86 | (2006.01) |
| C12N 5/02 | (2006.01) |
| C12N 5/00 | (2006.01) |
| C12P 21/06 | (2006.01) |
| C12P 21/04 | (2006.01) |
| C12N 5/07 | (2010.01) |
| C12N 7/00 | (2006.01) |

(52) U.S. Cl.
USPC ........ 435/456; 435/69.1; 435/70.1; 435/70.3; 435/325; 435/326; 435/352; 435/358; 435/320.1; 435/235.1

(58) Field of Classification Search
None
See application file for complete search history.

(56) References Cited

U.S. PATENT DOCUMENTS 5,834,589 A * 11/1998 Meruelo et al. ............... 530/350
7,071,301 B1 * 7/2006 Meruelo et al. ............... 530/350
2004/0228857 A1 * 11/2004 Page et al. .................. 424/141.1
2006/0099685 A1 * 5/2006 Yallop et al. ................. 435/69.1
2007/0003522 A1 * 1/2007 Albritton ..................... 424/93.2

FOREIGN PATENT DOCUMENTS

WO   WO 97/35996 A1   10/1997
WO   WO 02/022663      * 3/2002 ........... C07K 14/005

OTHER PUBLICATIONS

Masuda et al. "Molecular Characterization of a Neuropathogenic and Nonerythroleukemogenic Variant of Friend Murine Leukemia Virus PVC-211" 66(5) Journal of Virology 2798-2806 (1992).*
Seiss et al. "Exceptional Fusogenicity of Chinese Hamster Overy Cells with Murine Retroviruses Suggests Roles for Cellular Factor(s) and Receptor Clusters in the Membrane Fusion Process" 70(6) 3432-3439 (1996).*
Bleck "An Alternative Method for the Rapid Generation of STable, High-Expressing Mammalian Cell Lines" Bioprocessing Journal 1-7 (2005).*
Albritton et al. "A putative murine ecotropic retrovirus receptor gene encodes a multiple membrane-spanning protein and confers susceptibility to virus infection" 57 Cell 659-666 (1989).*
Masuda et al., "Capillary endothelial cell tropism of PVC-211 murine leukemia virus and its application for gene transduction," Journal of Virology 71(8):6168-6173 (1997), American Society for Microbiology, Washington, D.C.
Kozak et al., "Genetic Mapping of a Cloned Sequence Responsible for Susceptibility to Ecotropic Murine Leukemia Viruses," Journal of Virology 64(6):3119-3121 (1990), American Society for Microbiology, Washington, D.C.
Database EMBL (European Molecular Biology Laboratory), "Friend murine leukemia virus (circular intermediate) env polyprotein gene, complete cds.," EMBL database accession No. K02714, Jan. 28, 1986.
Database EMBL (European Molecular Biology Laboratory), "Friend murine leukemia virus, complete genome," EMBL database accession No. M93134, Jun. 8, 1992.

* cited by examiner

*Primary Examiner* — Jennifer Dunston
*Assistant Examiner* — Nancy J Leith
(74) *Attorney, Agent, or Firm* — Nevrivy Patent Law Group P.L.L.C.

(57) ABSTRACT

The present invention relates to methods of host cell transduction utilizing ecotropic retroviral vector particles. The retroviral vector particle may comprise an envelope of Friend murine leukaemia virus, in particular the envelope encoded by molecular clone PVC-211 and the host cell may be engineered to recombinantly express the Rec1 receptor. The retroviral vector particles and methods of the invention can be used to introduce expressible polynucleotide sequences of interest into host cells with high efficiency. This results in protein production methods with higher yield (mg/L) and a reduction in manufacturing costs that could be used in a range of applications including for example, the production of therapeutic proteins, vaccines and antibodies.

20 Claims, 30 Drawing Sheets

FIG. 1H-1

5'-
GACGGATCGGGAGATCTCCCGATCCCCTATGGTCGACTCTCAGTACAATCTGCTCTGATGCCGCA
TAGTTAAGCCAGTATCTGCTCCCTGCTTGTGTGTTGGAGGTCGCTGAGTAGTGCGCGAGCAAAA
TTTAAGCTACAACAAGGCAAGGCTTGACCGACAATTGCATGAAGAATCTGCTTAGGGTTAGGCG
TTTTGCGCTGCTTCGCGATGTACGGGCCAGATATACGC<u>GTTGACATTGATTATTGACTAGTTAT</u>
                                                    230 CMV promoter
<u>TAATAGTAATCAATTACGGGGTCATTAGTTCATAGCCCATATATGGAGTTCCGCGTTACATAAC</u>
<u>TTACGGTAAATGGCCCGCCTGGCTGACCGCCCAACGACCCCCGCCCATTGACGTCAATAATGACG</u>
<u>TATGTTCCCATAGTAACGCCAATAGGGACTTTCCATTGACGTCAATGGGTGGACTATTTACGGT</u>
<u>AAACTGCCCACTTGGCAGTACATCAAGTGTATCATATGCCAAGTACGCCCCCTATTGACGTCAA</u>
<u>TGACGGTAAATGGCCCGCCTGGCATTATGCCCAGTACATGACCTTATGGGACTTTCCTACTTGG</u>
<u>CAGTACATCTACGTATTAGTCATCGCTATTACCATGGTGATGCGGTTTTGGCAGTACATCAATG</u>
<u>GGCGTGGATAGCGGTTTGACTCACGGGGATTTCCAAGTCTCCACCCCATTGACGTCAATGGGAG</u>
<u>TTTGTTTTGGCACCAAAATCAACGGGACTTTCCAAAATGTCGTAACAACTCCGCCCCATTGACG</u>
<u>CAAATGGGCGGTAGGCGTGTACGGTGGGAGGTCTATATAAGCAGAGCTCT</u>CTGGCTAACTAGAG
                                                              820
AACCCACTGCTTACTGGCTTATCGAAATTAATACGACTCACTATAGGGAGACCCAAGCTTGGTA
CCGAGCTCGG<u>ATCGATATCTGCGGCCGCGTCGACGGAATTCAGTGGATCCACTAGTAACGGCCG</u>
          909 Multiple cloning site
<u>CCAGTGTGCTGGAATTAATTCGCTGTCTGCGAGGGCCAGCTGTTGGGGTGAGTACTCCCTCTCA</u>
     971   974 Synthetic intron
<u>AAAGCGGGCATGACTTCTGCGCTAAGATTGTCAGTTTCCAAAAACGAGGAGGATTTGATATTCA</u>
<u>CCTGGCCCGCGGTGATGCCTTTGAGGGTGGCCGCGTCCATCTGGTCAGAAAAGACAATCTTTTT</u>
<u>GTTGTCAAGCTTGAGGTGTGGCAGGCTTGAGATCTGGCCATACACTTGAGTGACAATGACATCC</u>
<u>ACTTTGCCTTTCTCTCCACAGGTGTCCACTCCCAGGTCCAACTGCAGGTC</u>GAGCATGCATCTAGG
                                                                   1269
GCGGCCAATT<u>CCGCCCCTCTCCCTCCCCCCCCCCTAACGTTACTGGCCGAAGCCGCTTGGAATAA</u>
          1295 IRES
<u>GGCCGGTGTGCGTTTGTCTATATGTGATTTTCCACCATATTGCCGTCTTTTGGCAATGTGAGGG</u>
<u>CCCGGAAACCTGGCCCTGTCTTCTTGACGAGCATTCCTAGGGGTCTTTCCCCTCTCGCCAAAGGA</u>
<u>ATGCAAGGTCTGTTGAATGTCGTGAAGGAAGCAGTTCCTCTGGAAGCTTCTTGAAGACAAACAA</u>
<u>CGTCTGTAGCGACCCTTTGCAGGCAGCGGAACCCCCCACCTGGCGACAGGTGCCTCTGCGGCCAA</u>
<u>AAGCCACGTGTATAAGATACACCTGCAAAGGCGGCACAACCCCAGTGCCACGTTGTGAGTTGGA</u>

FIG. 1H-2

TAGTTGTGGAAAGAGTCAAATGGCTCTCCTCAAGCGTATTCAACAAGGGGCTGAAGGATGCCCA
GAAGGTACCCCATTGTATGGGATCTGATCTGGGGCCTCGGTGCACATGCTTTACATGTGTTTAG
TCGAGGTTAAAAAAACGTCTAGGCCCCCCGAACCACGGGGACGTGGTTTTCCTTTGAAAAACAC
GATGATAAGCTTGCCACAACCCGGGATGACCGAGTACAAGCCCACGGTGCGCCTCGCCACCCGCG
            1881        1888 Puromycin resistance gene
ACGACGTCCCCAGGGCCGTACGCACCCTCGCCGCCGTTCGCCGACTACCCCGCCACGCGCCAC
ACCGTCGATCCGGACCGCCACATCGAGCGGGTCACCGAGCTGCAAGAACTCTTCCTCACGCGCGT
CGGGCTCGACATCGGCAAGGTGTGGGTCGCGGACGACGGCGCCGCGGTGGCGGTCTGGACCACG
CCGGAGAGCGTCGAAGCGGGGGCGGTGTTCGCCGAGATCGGCCCGCGCATGGCCGAGTTGAGCG
GTTCCCGGCTGGCCGCGCAGCAACAGATGGAAGGCCTCCTGGCGCCGCACCGGCCCAAGGAGCCC
GCGTGGTTCCTGGCCACCGTCGGCGTCTCGCCCGACCACCAGGGCAAGGGTCTGGGCAGCGCCGT
CGTGCTCCCCGGAGTGGAGGCGGCCGAGCGCGCCGGGGTGCCCGCCTTCCTGGAGACCTCCGCGC
CCCGCAACCTCCCCTTCTACGAGCGGCTCGGCTTCACCGTCACCGCCGACGTCGAGGTGCCCGAA
GGACCGCGCACCTGGTGCATGACCGGCAAGCCCGGTGCCTGACTCTAGAGGTCGGCTGATCAGCCT
                                                          2487   2489 Poly A signal
CGACTGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGGGAAGACA
ATAGCAGGCATGCTGGGGATGCGGTGGGCTCTATGGCTTCTGAGGCGGAAAGAACCAGCTGGGG
                                                                  2773
CTCGAGTGCATTCTAGTTGTGGTTTGTCCAAACTCATCAATGTATCTTATCATGTCTGTATACC
GTCGACCTCTAGCTAGAGCTTGGCGTAATCATGGTCATAGCTGTTTCCTGTGTGAAATTGTTAT
CCGCTCACAATTCCACACAACATACGAGCCGGAAGCATAAAGTGTAAAGCCTGGGGTGCCTAAT
GAGTGAGCTAACTCACATTAATTGCGTTGCGCTCACTGCCCGCTTTCCAGTCGGGAAACCTGTC
GTGCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAGCA
AAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCAATGCTCACGCTGT
AGGTATCTCAGTTCGGTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTAAGGGATTTTG

FIG. 1H-3

TCATGAGATTATCAAAAAGGATCTTCACCTAGATCCTTTTAAATTAAAAATGAAGTTTTAAATC
AATCTAAAGTATATATGAGTAAACTTGGTCTGACAGTTACCAATGCTTAATCAGTGAGGCACCT
ATCTCAGCGATCTGTCTATTTCGTTCATCCATAG<u>TTGCCTGACTCCCCGTCGTGTAGATAACTAC</u>
                                        4087 Ampicillin resistance gene
<u>GATACGGGAGGGCTTACCATCTGGCCCCAGTGCTGCAATGATACCGCGAGACCCACGCTCACCG</u>

<u>GCTCCAGATTTATCAGCAATAAACCAGCCAGCCGGAAGGGCCGAGCGCAGAAGTGGTCCTGCAA</u>

<u>CTTTATCCGCCTCCATCCAGTCTATTAATTGTTGCCGGGAAGCTAGAGTAAGTAGTTCGCCAGT</u>

<u>TAATAGTTTGCGCAACGTTGTTGCCATTGCTAC</u>AGGCATCGTGGTGTCACGCTCGTCGTTTGGT
                                    4603
ATGGCTTCATTCAGCTCCGGTTCCCAACGATCAAGGCGAGTTACATGATCCCCCATGTTGTGCA
AAAAAGCGGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATGCTTTTCT
GTGACTGGTGAGTACTCAACCAAGTCATTCTGAGAATAGTGTATGCGGCGACCGAGTTGCTCTT
GCCCGGCGTCAATACGGGATAATACCGCGCCACATAGCAGAACTTTAAAAGTGCTCATCATTGG
AAAACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGCAAA
AACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATA
TTTGAATGTATTTAGAAAAATAAACAAATAGGGGTTCCGCGCACATTTCCCCGAAAAGTGCCAC
CTGACGTC-3'

FIG. 1I-1

```
5'-
AGTGAAAGACCCCACCTGTAGGTTTGGCAAGCTAGCTTAAGTAACGCCATTTTGCAAGGCATGG
1  5' LTR
AAAATACATAACTGAGAATAGAGAAGTTCAGATCAAGGTTAGGAACAGAGAGACAGCAGAATA

TGGGCCAAACAGGATATCTGTGGTAAGCAGTTCCTGCCCCGGCTCAGGGCCAAGAACAGATGGT

CCCCAGATGCGGTCCCGCCCTCAGCAGTTTCTAGAGAACCATCAGATGTTTCCAGGGTGCCCCAA

GGACCTGAAAATGACCCTGTGCCTTATTTGAACTAACCAATCAGTTCGCTTCTCGCTTCTGTTC

GCGCGCTTCTGCTCCCCGAGCTCAATAAAAGAGCCCACAACCCCTCACTCGGCGCGCCAGTCCTC

CGATAGACTGCGTCGCCCGGGTACCCGTATTCCCAATAAAGCCTCTTGCTGTTTGCATCCGAATC
            400
GTGGACTCGCTGATCCTTGGGAGGGTCTCCTCAGATTGATTGACTGCCCACCTCGGGGGTCTTTC
ATTTGGAGGTTCCACCGAGATTTGGAGACCCCTGCCTAGGGACCACCGACCCCCCGCCGGGAGG
TAAGCTGGCCAGCGGTCGTTTCGTGTCTGTCTCTGTCTTTGTGCGTGTTTGTGCCGGCATCTAAT
GTTTGCGCCTGCGTCTGTACTAGTTAGCTAACTAGCTCTGTATCTGGCGGACCCGTGGTGGAAC
TGACGAGTTCTGAACACCCGGCCGGAACCCTGGGAGACGTCCCAGGGACTTTGGGGGCCGTTTT
TGTGGCCCGACCTGAGGAAGGGAGTCGATGTGGAATCCGACCCCGTCAGGATATGTGGTTCTGG
TAGGAGACGAGAACCTAAAACAGTTCCCGCCTCCGTCTGAATTTTTGCTTTCGGTTTGGAACCG
AAGCCGCGGTCTTGTCTGCTGCAGCGCTGCAGCATCGTTCTGTGTTGTCTCTGTCTGACTGTGT
TTCTGTATTTGTCTGAAAATTAGGGCCAGACTGTTACCACTCCCTTAAGTTTGACCTTAGGTCA
CTGGAAAGATGTCGAGCGGATCGCTCACAACCAGTCGGTAGATGTCAAGAAGAGACGTTGGGTT
ACCTTCTGCTCTGCAGAATGGCCAACCTTTAACGTCGGATGGCCGCGAGACGGCACCTTTAACCG
AGACCTCATCACCCAGGTTAAGATCAAGGTCTTTTCACCTGGCCCGCATGGACACCCAGACCAG
GTCCCCTACATCGTGACCTGGGAAGCCTTGGCTTTTGACCCCCTCCCTGGGTCAAGCCCTTTGT
ACACCCTAAGCCTCCGCCTCCTCTTCCTCCATCCGCCCCGTCTCTCCCCTTGAACCTCCTCGTTC
GACCCCGCCTCGATCCTCCCTTTATCCAGCCCTCACTCCTTCTCTAGGCGCCGGAATTAGATCTC
TCGAGGTTAACGAATTCCGCCCCTCTCCCTCCCCCCCCCCTAACGTTACTGGCCGAAGCCGCTTG
            1437 IRES
GAATAAGGCCGGTGTGCGTTTGTCTATATGTTATTTTCCACCATATTGCCGTCTTTTGGCAATG

TGAGGGCCCGGAAACCTGGCCCTGTCTTCTTGACGAGCATTCCTAGGGGTCTTTCCCCTCTCGCC

AAAGGAATGCAAGGTCTGTTGAATGTCGTGAAGGAAGCAGTTCCTCTGGAAGCTTCTTGAAGAC

AAACAACGTCTGTAGCGACCCTTTGCAGGCAGCGGAACCCCCCACCTGGCGACAGGTGCCTCTGC

GGCCAAAAGCCACGTGTATAAGATACACCTGCAAAGGCGGCACAACCCCAGTGCCACGTTGTGA

GTTGGATAGTTGTGGAAAGAGTCAAATGGCTCTCCTCAAGCGTATTCAACAAGGGGCTGAAGGA

TGCCCAGAAGGTACCCCATTGTATGGGATCTGATCTGGGGCCTCGGTGCACATGCTTTACATGT

GTTTAGTCGAGGTTAAAAAACGTCTAGGCCCCCCGAACCACGGGGACGTGGTTTTCCTTTGAAA
```

FIG. 1I-2

```
AACACGATGATAATATGGCCACAACCATGGTGAGCAAGGGCGAGGAGCTGTTCACCGGGGTGGT
               2012          2025 GFP
GCCCATCCTGGTCGAGCTGGACGGCGACGTAAACGGCCACAAGTTCAGCGTGTCCGGCGAGGGC
GAGGGCGATGCCACCTACGGCAAGCTGACCCTGAAGTTCATCTGCACCACCGGCAAGCTGCCCGT
GCCCTGGCCCACCCTCGTGACCACCCTGACCTACGGCGTGCAGTGCTTCAGCCGCTACCCCGACC
ACATGAAGCAGCACGACTTCTTCAAGTCCGCCATGCCCGAAGGCTACGTCCAGGAGCGCACCATC
TTCTTCAAGGACGACGGCAACTACAAGACCCGCGCCGAGGTGAAGTTCGAGGGCGACACCCTGG
TGAACCGCATCGAGCTGAAGGGCATCGACTTCAAGGAGGACGGCAACATCCTGGGGCACAAGCT
GGAGTACAACTACAACAGCCACAACGTCTATATCATGGCCGACAAGCAGAAGAACGGCATCAAG
GTGAACTTCAAGATCCGCCACAACATCGAGGACGGCAGCGTGCAGCTCGCCGACCACTACCAGC
AGAACACCCCCATCGGCGACGGCCCCGTGCTGCTGCCCGACAACCACTACCTGAGCACCCAGTCC
GCCCTGAGCAAAGACCCCAACGAGAAGCGCGATCACATGGTCCTGCTGGAGTTCGTGACCGCCG
CCGGGATCACTCTCGGCATGGACGAGCTGTACAAGTAAGTCGACCTGCAGCCAAGCTTATCGAT
                              2744
AAAATAAAAGATTTTATTTAGTCTCCAGAAAAAGGGGGGAATGAAAGACCCCACCTGTAGGTT
TGGCAAGCTAGCTTAAGTAACGCCATTTTGCAAGGCATGGAAAATACATAACTGAGAATAGAG
AAGTTCAGATCAAGGTTAGGAACAGAGAGACAGCAGAATATGGGCCAAACAGGATATCTGTGG
TAAGCAGTTCCTGCCCCGGCTCAGGGCCAAGAACAGATGGTCCCCAGATGCGGTCCCGCCCTCAG
CAGTTTCTAGAGAACCATCAGATGTTTCCAGGGTGCCCCAAGGACCTGAAAATGACCCTGTGCC
                            3050  3'LTR
TTATTTGAACTAACCAATCAGTTCGCTTCTCGCTTCTGTTCGCGCGCTTCTGCTCCCCGAGCCTCA
ATAAAAGAGCCCACAACCCCTCACTCGGCGCGCCAGTCCTCCGATAGACTGCGTCGCCCGGGTAC
CCGTGTATCCAATAAACCCTCTTGCAGTTGCATCCGACTTGTGGTCTCGCTGTTCCTTGGGAGGG
TCTCCTCTGAGTGATTGACTACCCGTCAGCGGGGGTCTTTCAGAATTGGTAATCATGGTCATAG
CTGTTTCCTGTGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGCGCTCACTGCC
CGCTTTCCAGTCGGGAAACCTGTCGTGCCAGCTGCATTAATGAATCGGCCAACGCGCGGGGAGA
GGCGGTTTGCGTATTGGGCGCTCTTCCGCTTCCTCGCTCACTGACTCGCTGCGCTCGGTCGTTCG
                  3550
GCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCG
TTGCTGGCGTTTTTCCATAGGCTCCGCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCGTTCGCTCCAAGCTG
```

FIG. 1I-3

GGCTGTGTGCACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACG
CGCAGAAAAAAGGATCTCAAGAAGATCCTTTGATCTTTTCTACGGGGTCTGACGCTCAGTGGA
ACGAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCATAGTT
5362 Ampicillin resistance gene
GCCTGACTCCCCGTCGTGTAGATAACTACGATACGGGAGGGCTTACCATCTGGCCCCAGTGCTGC

AATGATACCGCGAGACCCACGCTCACCGGCTCCAGATTTATCAGCAATAAACCAGCCAGCCGGA

AGGGCCGAGCGCAGAAGTGGTCCTGCAACTTTATCCGCCTCCATCCAGTCTATTAATTGTTGCC

GGGAAGCTAGAGTAAGTAGTTCGCCAGTTAATAGTTTGCGCAACGTTGTTGCCATTGCTACAGG

CATCGTGGTGTCACGCTCGTCGTTTGGTATGGCTTCATTCAGCTCCGGTTCCCAACGATCAAGGC

GAGTTACATGATCCCCCATGTTGTGCAAAAAAGCGGTTAGCTCCTTCGGTCCTCCGATCGTTGT

CAGAAGTAAGTTGGCCGCAGTGTTATCACTCATGGTTATGGCAGCACTGCATAATTCTCTTACT

GTCATGCCATCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGCGCCACATAG

CAGAACTTTAAAAGTGCTCATCATTGGAAAACGTTCTTCGGGGCGAAAACTCTCAAGGATCTTA

CCGCTGTTGAGATCCAGTTCGATGTAACCCACTCGTGCACCCAACTGATCTTCAGCATCTTTTAC

TTTCACCAGCGTTTCTGGGTGAGCAAAAACAGGAAGGCAAAATGCCGCAAAAAAGGGAATAAG

GGCGACACGGAAATGTTGAATACTCATACTCTTCCTTTTTCAATATTATTGAAGCATTTATCAG
4505
GGTTATTGTCTCATGAGCGGATACATATTTGAATGTATTTAGAAAAATAAACAAATAGGGGTT
CCGCGCACATTTCCCCGAAAAGTGCCACCTGACGTCTAAGAAACCATTATTATCATGACATTAA
CCTATAAAAATAGGCGTATCACGAGGCCCTTTCGTCTCGCGCGTTTCGGTGATGACGGTGAAAA
CCTCTGACACATGCAGCTCCCGGAGACGGTCACAGCTTGTCTGTAAGCGGATGCCGGGAGCAGA
CAAGCCCGTCAGGGCGCGTCAGCGGGTGTTGGCGGGTGTCGGGGCTGGCTTAACTATGCGGCAT
CAGAGCAGATTGTACTGAGAGTGCACCATATGCGGTGTGAAATACCGCACAGATGCGTAAGGAG
AAAATACCGCATCAGGCGCCATTCGCCATTCAGGCTGCGCAACTGTTGGGAAGGGCGATCGGTG
CGGGCCTCTTCGCTATTACGCCAGCTGGCGAAAGGGGGATGTGCTGCAAGGCGATTAAGTTGGG
TAACGCCAGGGTTTTCCCAGTCACGACGTTGTAAAACGACGGCCAGTGCCACGCTCTCCCTTATG
CGACTCCTGCATTAGGAAGCAGCCCAGTAGTAGGTTGAGGCCGTTGAGCACCGCCGCCGCAAGG
AATGGTGCATGCAAGGAGATGGCGCCCAACAGTCCCCCGGCCACGGGGCCTGCCACCATACCCAC
GCCGAAACAAGCGCTCATGAGCCCGAAGTGGCGAGCCCGATCTTCCCCATCGGTGATGTCGGCG
ATATAGGCGCCAGCAACCGCACCTGTGGCGCCGGTGATGCCGGCCACGATGCGTCCGGCGTAG

RETROVIRAL VECTOR PARTICLES AND METHODS FOR THEIR GENERATION AND USE

CROSS REFERENCE TO RELATED APPLICATIONS

This application is the U.S. National Stage under 35 U.S.C. §371 of International Application No.: PCT/EP2010/067946, filed Nov. 22, 2010, which claims the benefit of U.S. Provisional Appl. No. 61/263,539, filed Nov. 23, 2009.

REFERENCE TO A SEQUENCE LISTING SUBMITTED ELECTRONICALLY VIA EFS-WEB

The content of the sequence listing (Name: Sequence_listing_ST25.txt, Size: 116,665 bytes; and Date of Creation: May 18, 2012) electronically submitted via EFS-Web is incorporated by reference in its entirety.

FIELD OF THE INVENTION

The present invention describes methods for the generation of retroviral vector particles facilitating enhanced gene transfer efficiency upon transduction of host cells. In particular, the present invention relates to methods for retroviral transduction using ecotropic murine leukaemia virus (MLV)-derived vector particles and methods for modifying host cells to further increase gene transfer efficiency.

BACKGROUND

Over the last decade, the research work of many pharmaceutical and biotechnology companies has focused on the generation of biological products using recombinant DNA technology. Such biopharmaceutical products include e.g. enzymes, synthetic hormones, vaccines, monoclonal antibodies, cytokines. Whilst simple proteins can be produced using bacterial cultures, more complex proteins with a requirement for carbohydrate modification, e.g. glycosylation, assembly of different subunits, correct folding and functionality need to be produced in mammalian cells. Mammalian cell cultures are traditionally used for the production of glycosylated recombinant protein products and commonly used cell lines include, Chinese hamster ovary (CHO) cells, 293 Human embryonic Kidney (HEK) cells, COS cells, Baby Hamster Kidney (BHK) cells, PER.C6® and mouse myeloma cell lines such as NS0 or Sp2/0.

Since recombinant proteins for the therapy of human diseases need to have natural folding and post-translational modification and because they need to remain pharmacologically active for a defined shelf-life, supply of recombinant proteins for clinical studies and therapy requires the development of a highly reproducible and controlled production process. Such a process should ensure high quality and stability of the product in accordance with the quality obligations of the regulatory authorities at an acceptable cost of goods.

Mammalian cell lines, which allow the production of therapeutic proteins, are required to have high productivities and stable phenotypic and genotypic product expression profiles. The introduction of genetic information into a host cell genome by the process of DNA transfection is acknowledged to be an inefficient process. Therefore the present invention addresses this problem by utilising a method of retroviral transduction to achieve highly efficient transfer of genetic information into the genome of host cells. A current method of retroviral expression of recombinant proteins in the only industry approved production cell line utilises a pantropic vector with the ability to infect all species and therefore requires a Bio safety level 2 (BSL2) system (Bleck, 2005). This is a potential safety concern for the generation of therapeutic proteins resulting in higher costs during production to ensure staff safety and comply with the associated regulations. These drawbacks can be overcome by the use of an ecotropic retrovirus vector particle as described in the present invention, which has a restricted host cell infectivity and can therefore be used without safety concerns, resulting in lower production costs.

SUMMARY OF THE INVENTION

An embodiment of the present invention provides a method for transducing a host cell utilising a retroviral vector particle. The retroviral vector particle can comprise or be pseudotyped with an envelope of an ecotropic murine leukaemia virus (MLV) or a portion of the envelope that enables the pseudotyped retroviral vector particle to retain the host range and infectivity conferred by the full length envelope. Preferably the envelope is from Friend murine leukaemia virus (Fr-MLV), and more preferably the envelope is from a variant of Fr-MLV known as PVC-211 MLV. The envelope of PVC-211 (encoded by the nucleic acid of SEQ ID No: 1) displays the host range and infectivity of the native retrovirus (e.g. ecotropic MLV or Fr-MLV) but has not been used before for the generation of retroviral vector particles for the transduction of host cells. Since an ecotropic MLV envelope is used, the infectivity of the retroviral vector particle is limited to the same species and therefore these retroviral vector particles can only infect rodent species. Hence use of these retroviral vector particles in laboratory work requires only BSL 1 conditions, resulting in negligible safety concerns and significantly reduced costs, when compared to working under BSL2 conditions for example.

Host cells previously resistant to transfection or transduction with a retroviral vector particle comprising a wild type envelope (wtEnv) of Moloney murine leukaemia virus (Mo-MLV) show susceptibility or increased susceptibility to transduction when the retroviral vector particle comprises a Fr-MLV envelope. Preferably, the Fr-MLV envelope is from PVC-211. As such, the present invention provides a method for conferring or increasing susceptibility of a host cell to transduction comprising use of a retroviral vector particle comprising an envelope of Fr-MLV. In a preferred embodiment, the envelope of Fr-MLV is encoded by molecular clone PVC-211 (SEQ ID No: 1) or a fragment thereof, which when expressed has the same function as the full length PVC-211 envelope protein.

In one embodiment, said PVC-211 functional fragment effects transfection or transduction of a retroviral vector particle comprising an envelope of an ecotropic MLV into a host cell (e.g. a rodent cell). In one embodiment, said host cell is a host cell (e.g. a rodent cell) that is not (or is only poorly) susceptible to transfection or transduction with a retroviral vector particle comprising a wtEnv of Mo-MLV. In one embodiment, a functional fragment comprises a nucleotide sequence that has at least 80% (e.g. at least 85%, at least 90%, at least 92%, at least 94%, at least 96%, at least 98%, at least 99%) sequence identity to a nucleotide sequence consisting of at least 1500 contiguous nucleotides (eg. at least 1600 contiguous nucleotide, at least 1700 contiguous nucleotides, at least 1800 contiguous nucleotides, at least 1900 contiguous nucleotides, at least 2000 contiguous nucleotides) of SEQ ID NO: 1.

Use of a retroviral vector particle of the invention (e.g. comprising an envelope of PVC-211) results in much higher transduction efficiencies than the use of a retroviral vector particle comprising a wild type envelope of Mo-MLV.

Transduction efficiency can be further increased by the recombinant expression of the receptor for ecotropic MLV known as Rec1 (SEQ ID No: 32) or a functional fragment of this receptor sequence, in the target host cell. By expression of this receptor, host cells that were previously resistant to infection by ecotropic MLV particles become permissive to infection.

In one embodiment, expression of said Rec1 functional fragment in a host cell effects (e.g. facilitates or enhances) transfection or transduction of a retroviral vector particle comprising an envelope of an ecotropic MLV into said host cell (e.g. a rodent cell). In one embodiment, said host cell is a host cell (e.g. a rodent cell) that is not (or is only poorly) susceptible to transfection or transduction with a retroviral vector particle comprising a wtEnv of Mo-MLV. In one embodiment, a functional fragment comprises an amino acid sequence that has at least 80% (e.g. at least 85%, at least 90%, at least 92%, at least 94%, at least 96%, at least 98%, at least 99%) sequence identity to an amino acid sequence consisting of at least 400 contiguous amino acid residues (eg. at least 450 contiguous amino acid residues, at least 500 contiguous amino acid residues, at least 550 contiguous amino acid residues, at least 600 contiguous amino acid residues) of SEQ ID NO: 32.

The present invention therefore provides a method for increasing transduction efficiency comprising transducing a host cell with a retroviral vector particle comprising an ecotropic envelope of MLV, wherein the host cell recombinantly expresses the Rec1 receptor. Preferably the host cell is a hamster cell, more preferably the host cell is a Chinese hamster ovary (CHO) cell. Preferably the envelope of MLV is from a Fr-MLV, more preferably the envelope is encoded by molecular clone PVC-211 (SEQ ID No: 1) or a functional fragment thereof. The present invention demonstrates very high levels of transduction efficiency due to the synergistic effect resulting from the transduction of a host cell recombinantly expressing the Rec1 receptor with a retroviral vector particle comprising the envelope of PVC-211. The retroviral vector particles of the present invention can therefore be utilised to provide protein production methods with higher yields and a reduction in manufacturing costs, which could be used in a range of applications including for example, the production of therapeutic proteins, vaccines and antibodies. It has been demonstrated for the present invention that protein can be produced at a concentration of at least 1 mg/L in host cells recombinantly expressing the Rec1 receptor, transduced with a retroviral vector particle comprising the envelope of PVC-211.

In a further embodiment, the present invention provides a retroviral packaging cell for producing a retroviral vector particle comprising:
a) an envelope construct comprising a promoter operably linked to an envelope coding sequence of a Fr-MLV, wherein the envelope of Fr-MLV is encoded by molecular clone PVC-211 (SEQ ID NO: 1) or a functional fragment thereof; and
b) a packaging construct comprising a promoter operably linked to a nucleotide sequence encoding a retroviral gag and pol.

In addition to the envelope and packaging constructs, the packaging cell may also comprise a retroviral transfer vector. The transfer vector may comprise the components of a retroviral 5' LTR, a retroviral packaging sequence distal to the 5' LTR and a retroviral 3' LTR. In addition, the transfer vector may also comprise an internal ribosome entry site (IRES) and/or a marker gene such as a fluorescent protein, for example, GFP. Furthermore, the transfer vector may also comprise a heterologous nucleotide sequence, which encodes a protein of interest.

In an embodiment of the present invention, the packaging cell and transfer vector as described above can be coexpressed in a host cell under conditions effective to produce a retroviral vector particle. Suitable host cells can be selected from any mammalian or human cell line.

The retroviral vector particle generated by the above method can be used to transduce a target host cell so that the nucleotide sequence coding for a protein of interest is integrated into the host cell genome and the protein encoded by the gene is subsequently expressed by the host cell. Preferably the host cell is a hamster cell, more preferably a CHO cell.

Methods according to the present invention may be used to transduce host cells to produce a protein of interest. The transduced host cells are cultured under conditions so that a protein encoded by the gene of interest is expressed and then the expressed protein can be isolated from the culture and purified. The concentration of purified protein produced is preferably at a level of 1 mg/L or more.

The retroviral vector particle may encode at least one gene of interest, preferably at least two genes of interest. Preferably two genes of interest comprise an immunoglobulin heavy chain and an immunoglobulin light chain. However, in an alternative embodiment two genes of interest may be located on separate retroviral vector particles so that one retroviral vector particle comprises a gene that codes for an immunoglobulin heavy chain and another retroviral vector particle comprises a gene that code for an immunoglobulin light chain.

DESCRIPTION OF THE FIGURES

FIG. 1 shows schematic designs of expression constructs that can be used in the present invention. The drawings depict the schematic design of expression cassettes in a standard DNA cloning backbone (closed black line), containing the ampicilin-resistance gene (AmpR) and the bacterial origin of replication (ori). All non-retroviral expression vectors shown (FIGS. 1a to f) contain a poly-adenylation signal (polyA signal; black and white dashed box), an internal ribosome entry site (IRES; black box), a synthetic intron (black and white dotted box), and a promoter driving the expression of the transgene inserted 5' of the synthetic intron.

FIG. 1a: The construct pIRES-puro contains the reporter gene puromycin-resistance (puroR) flanked by the restriction-sites for XmaI and XbaI. This parental vector does not encompass any other transgene. The multiple cloning site 3' of the CMV-promoter includes unique restriction-sites for ClaI, NotI, EcoRI and BamHI in the multiple cloning site (MCS) for convenient insertion of an open reading frame (coding region) of choice.

FIG. 1b: pRec1-I-puro is derived from pIRES-puro and was modified by the insertion of the coding region of the receptor of ecotropic murine leukaemia virus (MLV) Rec1 using the restriction-sites NotI and BamHI.

FIG. 1c: pPVC-211 Env-I-puro was constructed by insertion of the envelope coding region of the molecular clone PVC-211 of ecotropic MLV into the recipient vector pIRES-puro using the sites in the MCS for NotI and EcoRI.

FIG. 1d: pwtEnv-I-puro was generated as for pPVC-211 Env-I-puro above, but encompasses the envelope coding region of wild type ecotropic MLV.

FIG. 1e: In contrast to FIGS. 1c and 1d, pIRES-bleo served as the recipient vector for the generation of the packaging construct pGP-1-bleo. In this vector, the selectable marker gene bleomycin-resistance (bleoR) is flanked by the restriction-sites XbaI and XmaI which allows for the controlled selection of transfected and bleomycin-resistant cells that will also express the structural genes of gag/pol of MLV (gag-pol (MLV)) inserted into the MCS employing NotI and EcoRI.

FIG. 1f: pPpgk-I-puro contains the murine phospho glycerol kinase gene promoter (Ppgk promoter) flanked by the restriction-sites MluI and ClaI replacing the CMV-promoter in the afore-mentioned constructs. The puromycin-resistance gene serves as a selectable marker (puroR).

FIGS. 1H-1 through 1H-3: Nucleotide sequence of the pIRES-puro construct (1-5021 base pairs (bp)), shown in FIG. 1a. The vector components are at the positions as indicated in FIG. 1h and as listed herein: CMV promoter (230-820 bp), Multiple cloning site (MCS; 909-971 bp), Synthetic intron (974-1269 bp), IRES (1295-1881 bp), puromycin resistance gene (1888-2487 bp), poly A signal (2489-2773 bp) and ampicillin resistance gene (4087-4603 bp).

FIGS. 1I-1 through 1I-3: Nucleotide sequence of the MigR1 vector (6231 bp), shown schematically in FIG. 1g. The vector components are at the positions as indicated in FIG. 1h and as listed herein: 5'LTR (1-400 bp), IRES (1437-2012), GFP (2025-2744), 3'LTR (3050-3550) and ampicillin resistance gene (5362-4505).

FIG. 3: FACS-analysis of transduced murine 1624-5 pre-B cells, CHO-S cells and CHO-S cell transfectants, expressing the recombinant receptor of ecotropic MLV Rec1 (CHO-S Rec1-I-puro). MLV-based vector particles displaying the envelope wtEnv of ecotropic MLV were used. Untransduced cells served as negative controls (NC). The expression of the transduced reporter gene GFP is detected.

Terminology

Figure 1A:
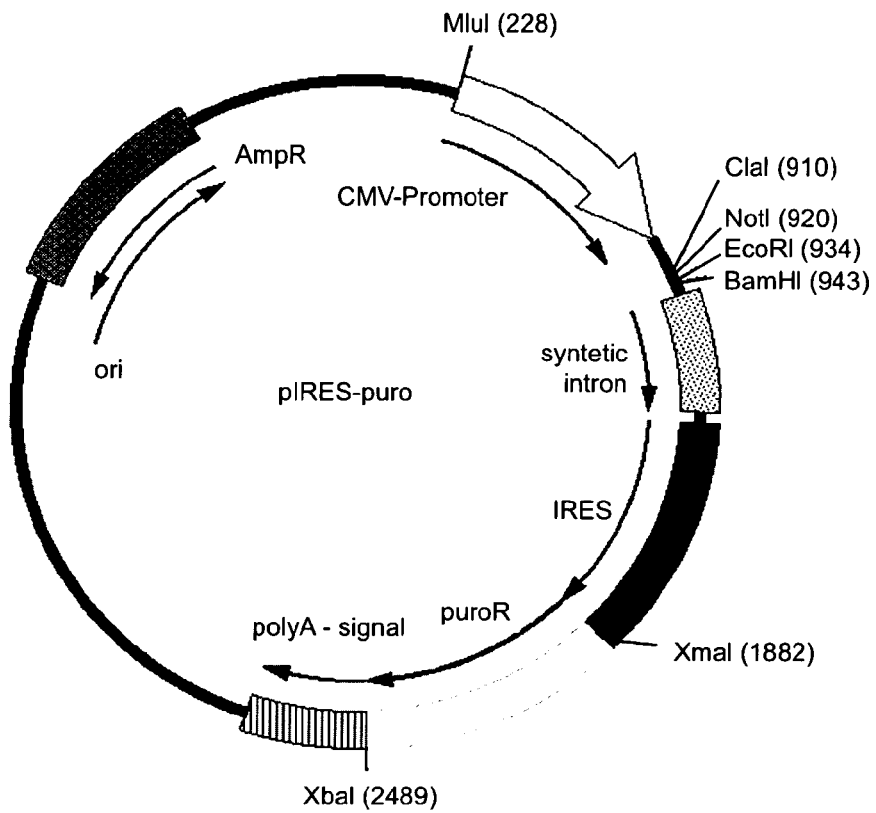
In FIGS. 1(a) to 1(e), the promoter is derived from human cytomegalovirus (CMV; white arrow).

Retroviral vector particle: A retroviral vector particle is a replication deficient retroviral particle that contains two copies of retroviral RNA (the transcript of the transfer vector), usually containing expression cassettes for a gene of interest. A retroviral vector particle is generated upon expression of helper virus constructs such as a packaging construct (providing the structural proteins Gag and Pol) and an envelope construct (providing the structural protein Env), wherein the constructs may or may not include a packaging signal, or a packaging construct providing all three structural proteins combined on one construct without a packaging signal, together with a transfer vector in one cell in a stable or transient fashion. A retroviral vector particle can be used to target delivery of a gene of interest encoded on the vector once only into target cells, a process called transduction.

A replication competent full-length retroviral genome is not used for the generation of retroviral vector particles and therefore the particles do not transfer full-length retroviral genomes and do not establish productive infection resulting in the generation of new infectious retroviral particles upon transduction into permissive or susceptible cells. Retroviral vector particles upon target cell entry deliver only transfer vector mRNA (the vector particle genome) comprising the long terminal repeats (LTRs) and the packaging signal psi (ψ), in addition to other nucleic acid sequences of choice, for example, reporter genes, IRES and/or coding regions of a gene of interest.

Retroviral vector particles can be derived from all members of the retrovirus family including Lentivirus, Spumavirus and Onco-retrovirus.

Retrovirus envelope proteins or Env proteins: the retroviral proteins found on the surface of the virion. The env gene typically encodes the envelope proteins/envelope of retroviruses. The native retroviral env gene product is generally a polyprotein precursor (in MLV it is referred to as gp85, a precursor protein) that is proteolytically cleaved during transport to yield two polypeptides. These two proteolytic cleavage products are (1) the surface protein (also referred to as SU protein and gp70) and (2) the transmembrane protein, TM or p15E. The SU protein is responsible for recognizing and binding to cellular receptors. The TM protein is involved in mediating the fusion of viral and cellular membranes necessary for virion entry and infection of the target cell.

Pseudotyped retrovirus: a retroviral vector comprising a heterologous envelope protein i.e. an envelope protein derived from a different retrovirus or virus.

Packaging cell/Packaging cell line: an engineered cell/cell line that does not produce a replication-competent retroviral genome but which provides the structural and functional Gag, Pol and Env proteins required for packaging of a replication-defective retroviral vector for the production of retroviral vector particles in the cell culture supernatant of the packaging cell/cell line.

Transfecting/Transfection: In the context of eukaryotic cells this is the process of introducing nucleic acid sequences into eukaryotic cells, usually associated with using chemical and/or physical methods.

Transforming/Transformation: In the context of eukaryotic cells this is the process of immortalizing a cell for the establishment of a continuously proliferating cell line.

Transducing: The process of delivering retroviral genomes into vertebrate host cells via the use of retroviral vector particles. For this, a packaging cell line, expressing structural proteins for viral particles (Gag, Pol and Env) is transfected with a recombinant viral vector construct comprising the regulatory elements for packaging of the viral vector construct into a retroviral vector particle. The produced retroviral vector particles can be used to transduce host cells leading to the stable integration of the retroviral vector encoded genetic information into the host cell genome.

Vector/Construct: A nucleic acid sequence which can be used to clone and to amplify genetic sequences and which allows the shuttling of genetic information between different organisms and species for further amplification and functional analysis.

DETAILED DESCRIPTION

Recombinant proteins can be produced in various expression systems such as prokaryotic (e.g. *E. coli*), eukaryotic (e.g. yeast, insect, vertebrate, mammalian), and in vitro expression systems.

Most commonly used methods for the large-scale production of protein-based biologics rely on the introduction of genetic material into host cells (production cells) by transfection of DNA vectors. While this leads to a transient expression of recombinant proteins, the transfected DNA vectors are rapidly degraded or get diluted upon culture of the production cells. Therefore, it is necessary to screen or to select for those host cells into which the transfected vector is stably maintained. However, only a small percentage of transfected cells will have integrated the foreign genetic material into their genome and so the process of identifying stable, high expressing cell lines is normally laborious and time consuming.

An alternative method for the insertion of genetic material into cells is the process of transduction, which utilises a viral vector. This process can result in almost 100% cell infectivity without severely affecting cell viability and some viruses can integrate into the host cell genome enabling stable expression of the foreign genetic material. A number of different viruses are commonly used, which include retroviruses, lentiviruses, adenoviruses and adeno-associated viruses. An object of the present invention is to provide a retroviral expression system for efficient and safe gene transfer into host cells for the production of protein-based biologics and an associated increase in yield of expressed protein.

As mentioned above, recombinant proteins can be produced in various expression systems. Recent developments include platforms such as yeast and plants but there are a number of drawbacks associated with these expression systems that need to be overcome before such systems can be approved for the production of recombinant proteins for therapeutic use in humans. Processing of yeast glycoproteins for example is different to that of mammalian glycoproteins, giving high-mannose type N-glycosylation, which results in a short circulatory half live in vivo and the possibility of altered protein activity (Wildt & Gerngross, 2005). For plant expression systems, the shortcomings relate to poor protein yields, poor protein stability and laborious downstream processing of the plant-derived proteins (Fischer et al., 2004).

Traditionally, recombinant proteins applicable for the treatment of human disease, like antibodies, have been expressed in mammalian cells such as rodent or human cells. A number of expression systems from these species have been approved by regulatory authorities for the production of clinical-grade therapeutic protein. However, vertebrate and mammalian cell based expression systems using the above-mentioned stable transfection of DNA vectors require long-time frames to establish stably producing cell lines and clones, and an efficient and controlled genetic modification of such cells is often not trivial. These systems have therefore been the focus of most major developments to improve product yield and developmental time lines. Such developments include novel or modified genetic elements to improve transcription rate, high throughput screening concepts to obtain highly productive clones and host cell lines that grow to densities in serum-free chemically defined media that have achieved specific productivities of values about 50 pg/cell/day (Bergmann et al., 2007). For example, use of the CHO DG-44 high producer cell line (BI HEX® CHO; Boehringer Ingelheim) can result in a constant specific productivity of a monoclonal antibody of 55 pg/cell/day for 120 days in culture. This cell line combines an efficient vector system with novel genetic elements for high-level product expression and the enrichment of high producers (Bergmann et al., ibid).

A further mammalian expression system that is well known in the art utilises a robust viral promoter and selection via glutamine metabolism to provide rapid development of high-yielding and stable cell lines. In the absence of glutamine in the growth medium, the glutamine synthetase (GS) enzyme plays an essential role in the survival of mammalian cells in culture. Some mammalian cell lines, such as mouse myeloma lines, do not express sufficient GS to survive without added glutamine. With these cell lines, a transfected GS gene can function as a selectable marker by permitting growth in a glutamine-free medium (WO 91/006657 A1; WO 89/010404 A1; WO 86/005807 A1). Other cell lines, such as CHO cell lines, express sufficient GS to survive without exogenous glutamine. In these cases, the GS inhibitor, methionine sulphoximine, can be used to inhibit endogenous GS activity such that only transfectants with additional GS activity can survive (WO 87/004462 A1). Maximum expression levels attainable depend on the product but cell lines producing over 5 g/L of recombinant antibody have been created, with specific production rates in the range 15-65 pg/cell/day.

Whilst the above mammalian expression systems have focused on the improvement of recombinant product expression by the use of genetic elements such as strong promoters and selection systems, the present invention describes an approach to increase recombinant protein expression by transferring the gene of interest into a mammalian host cell in a highly efficient manner by utilising retroviral vector particles.

The tropism of a retrovirus or retroviral vector particle is determined by the Env proteins on the surface of the virion. However, in addition to the amino acid sequence of the Env protein, retroviral Env proteins also undergo glycosylation by cellular enzymes in the lumen of the rough endoplasmic reticulum that attach oligosaccharides to N-linked glycosylation sites. Such carbohydrate moieties play a role in glycoprotein biosynthesis, transport and stability, and may, for example, mask susceptible residues from proteolytic enzymes. Glycosylation may even reduce the immunogenicity of the protein by masking immunogenic three dimensional epitope structures (Elder et al., 1986).

Hamster cells, in particular Chinese hamster ovary (CHO) cells, are highly resistant to transduction of a retroviral vector pseudotyped by ecotropic MLV under normal conditions. In fact, the ecotropic glycoprotein-binding site appears to be masked or modified by the presence of an oligosaccharide side chain resulting from N-linked glycosylation-dependent modification of the receptor Rec1. This can be shown by treatment of CHO-K1 or BHK21 cells with the glycosylation inhibitor tunicamycin, which renders the cells sensitive to infection (Wilson & Eiden, 1991; Miller & Miller, 1992).

Masuda and colleagues have characterised a neuropathogenic variant, a molecular clone, of the Fr-MLV, termed PVC-211 (SEQ ID Nos: 1 & 2), which causes rapidly progressive neurodegenerative disease in susceptible rodents. This ecotropic MLV variant has been shown to infect cells (rat brain endothelial cells) that are resistant to infection by Fr-MLV and other ecotropic MLVs (Masuda et al., 1993). The rat brain cell tropism was shown to be attributable to two amino acid changes: Glu to Gly at position 116 and Glu to Lys at position 129 in the putative receptor-binding domain of the envelope SU protein (Masuda et al., 1996a). Further work by Masuda et al (1996b) determined an expanded host range in addition to the expanded cellular tropism of PVC-211 MLV, in which this variant was shown to be highly infectious for CHO-K1 cells and could also efficiently infect other cell lines derived from Chinese and Syrian hamsters.

Whilst the work of Matsuda and colleagues has shown the high infectivity of PVC-211, this virus strain has not been used before to alter the host cell tropism of replication incompetent viral particles. The present invention teaches for the first time the use of ecotropic retroviral particles that utilise the envelope protein of PVC-211 (SEQ ID No: 2). It is also possible that a portion of this protein (SEQ ID No: 2) may be used in the present invention, providing that on expression, a functional envelope protein is produced, which confers infectivity on the viral particles for rodent host cells. In addition, the present invention demonstrates that PVC-211 pseudotyped retroviral vector particles are infective for rodent cells but are not infective for cells of other non-rodent species, such as humans. In a preferred embodiment of the present invention, the rodent host cells are Chinese hamster ovary (CHO) cells, for example but not limited to, CHO-K1, CHO-S, CHO-T-REx™, CHO-GS, A2, A2H, CHO/dhFr-, GRL101, M1WT3, P22, RR-CHOK1, UT-1, XrS6 and other CHO cell lines that can be found in the cell collections of ECACC and/or ATCC.

Retroviral expression vectors are known in the art and have been used as a tool to transfer genes of interest into a wide variety of host cells. Bleck and colleagues have developed a system (GPEx®) that utilises replication-defective retroviral vectors derived from MLV that are pseudotyped with vesicular stomatitis virus G protein (VSV-G) to stably insert single copies of genes into dividing cells (Bleck, 2005). Since the envelope of VSV-G is used, these vectors are therefore pantropic and can infect all known species including humans. Whilst initially this may appear to be an advantageous feature of this system, the use of a pantropic virus also has drawbacks. For example, use of a pantropic virus in the laboratory means that Bio safety level (BSL) 2 conditions apply and work must be performed in laboratories that are of BSL2 standard. In addition, staff require special training to work with BSL2 level organisms.

The present invention, besides providing means for increasing retroviral transduction efficiency and increased protein yield utilises ecotropic retroviral particles, which means that host cell infectivity is restricted to rodent cells and therefore only BSL1 conditions i.e. standard laboratory conditions are required for work with these particles.

The retroviral vector particles and constructs for their manufacture of the present invention can be used to introduce gene sequences of interest into host cells for subsequent expression. The retroviral vector particles are enveloped virion particles that contain an expressible polynucleotide sequence and are capable of binding to and penetrating a target host cell to deliver the expressible sequence into the cell. The enveloped particle may have a wild type (wt) envelope of Moloney MLV (Mo-MLV; often written as just MLV) or may be pseudotyped with a wild type or engineered envelope protein from another viral species. Use of a non-native envelope protein can alter the host range and infectivity of the native retrovirus. The pseudotype envelope may be from a non-retroviral species or from a retroviral species. In a preferred embodiment of the present invention, the envelope protein is from MLV and is a variant of the Friend MLV (F-MLV), termed PVC-211 (Masuda et al., 1996a). Use of this envelope in retroviral vector particles, as described in the Examples has resulted in an increase in transduction efficiency of up to 13 fold when compared to retroviral vector particles utilising a wild type envelope.

The retroviral vector particles of the present invention can be used in a wide range of applications including, for example, protein production. Examples of such proteins include therapeutic proteins (cytokines, hormones, growth factors), vaccines and monoclonal antibodies.

Also encompassed by the present invention are a number of retroviral vector components, which contain the elements useful for producing a functional retroviral vector particle in a compatible host cell and packaging it into an expressible heterologous sequence. These components include an envelope construct, a packaging construct and a transfer vector and are described in more detail below.

The envelope construct may comprise a heterologous promoter operably linked to an envelope coding sequence. By the term 'operably linked', it is meant that the promoter is positioned in such a way that it can drive transcription of the recited coding sequences for the viral envelope. The envelope polypeptide is displayed on the viral surface and as discussed earlier is involved in the recognition and infection of host cells by a virus particle. The host range and specificity can be changed by modifying or substituting the envelope polypeptide, for example, with an envelope expressed by a different (heterologous) viral species by the process of pseudotyping (Yee et al., 1994). Common envelope polypeptides include VSV-G, HIV gp20, MLV (including native and modified forms), murine mammary tumour virus, gibbon ape leukaemia virus, Rous sarcoma virus, hepatitis viruses, influenza viruses. In an embodiment of the present invention, the envelope protein is from a Friend murine leukaemia virus (Fr-MLV). Preferably the envelope protein is from a variant strain of Fr-MLV known as PVC-211 (Kai & Furuta, 1984; Hoffman et al., 1992; Remington et al., 1992; Masuda et al., 1992; 1993; 1996;). A viral envelope protein can be modified or engineered to contain polypeptide sequences that allow the vector particle to target and infect host cells outside its normal range or more specifically limit transduction to a cell or tissue type. For example, the envelope protein can be joined in frame with targeting sequences, such as receptor ligands, antibodies (using an antigen-binding portion of an antibody or a recombinant antibody-type molecule, such as a single chain antibody), and polypeptide moieties or modifications thereof (e.g., where a glycosylation site is present in the targeting sequence) that, when displayed on the vector particle coat, facilitate directed delivery of the virion particle to a target cell of interest. Furthermore, envelope proteins can further comprise sequences that modulate cell function and/or mediate additional host-cell protein recognition. Modulating cell function with a transducing vector may increase or decrease transduction efficiency for certain cell types in a mixed population of cells. Examples include e.g. antibodies (e.g. single-chain antibodies that are specific for a cell-type) and essentially any antigen (including receptors) that is specific for such tissues as lung, liver, pancreas, heart, endothelial, smooth, breast, prostate, epithelial, vascular cancer, etc.

A promoter can be utilized to drive expression of the viral envelope coding sequence when operably linked to it. The promoter may be a constitutive promoter such as the promoter present in the 5'LTR or a heterologous promoter such as a promoter derived from human cytomegalovirus (CMV), murine phospho glycerin kinase (Ppgk) promoter, murine V-kappa gene promoter ($Pv_\kappa$), β-actin promoter, EF-1α promoter, EF-1α-HTLV-1 hybrid promoter, ferritin promoters, inducible promoters, constitutive promoters, and other promoters mentioned herein. Inducible promoters, like the tetracycline-inducible promoter (Gossen & Bujard, 1992), may either upregulate or downregulate expression by addition or removal of tetracycline or other antibiotics and derivatives thereof, like doxycycline. Preferably the promoter used in a construct of the present invention is the CMV promoter.

In addition, the envelope construct can further comprise transcription termination signals, such as a polyA signal that is effective to terminate transcription driven by the promoter sequence. Any suitable polyA sequence can be utilized, e.g., sequences from beta globin (mammalian, human, rabbit, etc), thymidine kinase, bovine growth hormone, SV40, and many others.

The packaging construct may comprise sequences coding for structural proteins (e.g. gag precursor) and/or processing proteins (e.g. pol precursor). The Gag-Pol sequences can be native or modified Gag-Pol sequences. These modifications include chimeric Gag-Pol, where the Gag and Pol sequences are obtained from different viruses (e.g., different species, subspecies, strains) and/or where the sequences have been modified to improve transcription and/or translation and/or reduce recombination. In other embodiments of the present invention, the sequences coding for the gag and pol precursors can be separated and placed on different vector constructs. For these vector constructs, each sequence has its own expression signals, for example, additional promoter and enhancer sequences can be placed upstream of the gag/pol in order to increase, improve or enhance transcription of the gag/pol precursor. Examples of promoters include, mammalian promoters (e.g., constitutive, inducible, tissue-specific), CMV, RSV, LTR from other retroviral species and other promoters as mentioned above and below.

In addition, the packaging construct can further comprise transcription termination signals, such as a polyA signal that is effective to terminate transcription driven by the promoter sequence, as described above.

Although the components described above contain the envelope and gag-pol precursor on different constructs, they can, if desired, be placed on the same construct or utilise a separate construct for each protein.

The transfer vector may comprise the polynucleotide sequences, which are packaged into the transducing retroviral vector particles. The transfer vectors, when comprising 5' LTR and 3' LTR, can be used for the production of vector particles that are capable of integrating into the host genome. A suitable vector backbone, which can be used for the preparation of a transfer vector of the present invention, is that of the MigR1 vector (Pear et al., 1998; http://www.lablife.org/p?a=vdb_view&id=g2.531Ogh0E_Yc2k4vlr3OZM.EUaXE-; FIG. 1i; SEQ ID No: 43). The retroviral transfer vector may comprise one or more of the following elements, for example, a retroviral 5' LTR, a packaging signal (psi/Ψ) distal to the 5'LTR and a retroviral 3' LTR. At least one expressible heterologous polynucleotide sequence can be inserted into the transfer vector between the packaging sequence and the U5 region of the 3' LTR.

Any suitable retroviral 5' LTR can be used in the transfer vector including an LTR obtained from any retrovirus species, sub-species or strain. The retroviral 5' LTR comprises signals utilized in gene expression, including enhancer, promoter, transcription initiation (capping), transcription terminator and polyadenylation. They are typically described as having U3, R, and U5 regions. The U3 region of the LTR contains enhancer, promoter and transcriptional regulatory signals, including RBEIII, NF-kB, SpI, AP-I and/or GABP motifs. The TATA box is located about 25 base pairs from the beginning of the R sequence, depending on the species and strain from which the 5' LTR was obtained. A completely intact 5' LTR can be used or a modified copy.

A packaging sequence (psi/Ψ) distal to the 5' LTR can also be present in the transfer vector. This sequence, which is recognized by the nucleocapsid (NC) domain of the Gag, is utilized in cis to facilitate encapsulation of the heterologous sequence of interest into the transducing vector (Lever et al., 1989). The psi packaging sequence (Ψ) is relatively autonomous of neighbouring sequences and its position in the transfer vector can be determined routinely (Mann & Baltimore, 1985).

Furthermore, a primer binding site (PBS) can also be located downstream of the 5' LTR.

The transfer vector can also include a retroviral 3' LTR comprising U3, R and U5 regions. The 3' LTR can be intact and native or it can be modified. Modifications can include those to produce an LTR that retains a minimal amount of functional activity e.g. transcriptional (promoter-enhancer) functional activity as seen with self-inactivating (SIN) vectors (Yu et al., 1986).

The transfer vector may also comprise an internal ribosome entry site (IRES) inserted for example between the packaging signal and the 3'LTR. Preferably the IRES is located between an expressible polynucleotide such as a reporter gene and/or a protein of interest. The use of an IRES element allows translation of multiple coding regions from a single promoter (Adam et al., 1991). When located between open reading frames in an RNA, IRES elements allow efficient translation of the downstream open reading frame by promoting entry of the ribosome at the IRES element followed by downstream initiation of translation. IRES elements from but not limited to poliovirus, encephalomyocarditis virus and swine vesicular disease virus can be used in retroviral vectors of the present invention.

An expressible heterologous polynucleotide sequence can be inserted into the transfer vector, for example, between the packaging sequence and the 3' LTR. The expressible sequence is the sequence which is packaged into the viral transfer vector, and which is expressed by the host cells after transduction with retroviral vector particles. Any heterologous sequence of interest can be inserted into the transfer vector providing the sequence size is less than approximately 8-12 kb. Heterologous sequences that can be inserted include those coding for therapeutic proteins, enzymes, antibodies and fragments thereof, reporter genes, siRNA, anti-sense, microRNAs, aptamers, ribozymes, cell surface receptors, proteins involved in DNA repair, proteins involved in RNA synthesis, any gene inhibitory or silencing sequence and any sequence which is to be delivered to a host cell via a retroviral transducing vector.

The transfer vector may also comprise a selection marker. Selection markers, conferring resistance to antibiotics useful for the selection of mammalian cells, include, but are not limited to, e.g. genes for puromycin, neomycin, hygromcin B, mycophenolic acid, histidinol, bleomycin, zeomycin and phleomycin resistance. For the expression of multimeric proteins, like antibodies, encoded by separate retroviral constructs, it is preferable that expression of different polypeptide chains are linked to different selection markers, thereby allowing separate, sequential or double selection for the stable transduction of corresponding expression constructs.

The 5' LTR can be operably linked to a polynucleotide sequence coding for a reporter or marker gene. Marker genes, allowing monitoring of retroviral transduction into host cells include, but are not limited to genes, conferring fluorescence to transduced cells, like e.g., but not limited to green fluorescent protein (GFP), enhanced green fluorescent protein (EGFP), yellow fluorescent protein (YFP), blue fluorescent protein (BFP) and red fluorescent protein (RFP). Alternatively, cell surface markers could be used such as CD4, CD7 or truncated variants thereof, CD34 or truncated variants thereof, or low affinity nerve growth factor receptor or truncated variants thereof. In a preferred embodiment the expression of these antibiotic selection markers, fluorescence markers or cell surface markers is coupled to the expression of the recombinant binding protein via an IRES, which in vertebrate cells allows the coupled co-expression of two genes from a single promoter element. However, the expression of a selection and/or marker gene from a separate expression cassette contained in the retroviral construct, driven by an additional promoter element is also encompassed by the present invention. For the expression of multimeric proteins, like immunoglobulins, from separate retroviral vectors, it is preferred that different binding protein chains are linked to different selection and/or screening markers, thereby allowing separate monitoring for the stable transduction of the different expression constructs.

In case the expression of the recombinant binding protein is driven by a separate promoter, as outlined above, any selection or screening marker gene can also be cloned downstream of the 5'LTR and downstream of the 5'LTR and ψ packaging signal, such that its expression is driven by the 5'LTR promoter.

To increase the flexibility of the transfer vector and to create a modular vector system, multiple cloning sites (MCS) can further be incorporated into the vector that facilitate the insertion of a heterologous sequences of interest. This MCS facilitates the introduction of, for example, any promoter, a single gene, two genes etc.

Any of the sequences which are present in the retroviral vector components of the present invention can be modified from their native form, e.g. to improve transcription, to improve translation, to reduce or alter secondary RNA structure, and/or to decrease recombination. Modifications include, e.g., nucleotide addition, deletion, substitution, and replacements. For example, coding sequences for gag and pol can be modified by replacing naturally occurring codons with non-naturally-occurring codons, e.g., to improve translation in a host cell by substituting them with codons that are translated more effectively in the host cell. The host cell can be referred to as a compatible cell, e.g. to indicate the sequence modification has its effect when the sequence is expressed in a particular host cell type. In addition, sequences can be modified to remove regulatory elements such as the packaging sequence. Sequences can also be altered to eliminate recombination sites.

The present invention also provides retroviral packaging systems for producing retroviral vector particles. A packaging system can comprise a plurality of constructs that are useful for manufacturing fully enveloped and functional retroviral vector particles. These include, for example, an envelope construct, a packaging construct and a transfer vector as described in detail above. The envelope construct and the packaging construct may be present as different constructs or together on the same construct such that the envelope protein and the gag-pol proteins are on the same construct. Such a construct is also known in the art as a helper construct.

A further embodiment of the present invention is a retroviral vector particle and a method of producing a retroviral vector particle. The retroviral vector components described above can be used transiently in host cells to produce vector particles. Examples of host cells that can be used to produce vector particles include any mammalian or human cell line or primary cell. Non-limiting examples include HEK 293, HT1080, NIH 3T3, Jurkat, and SupTlcells. Other examples include HeLa, VERO, L929, COS-1, COS-7, BHK, MRC-5, BAE-I, HEP-G2, NS0, U937, Namalwa, HL60, WEHI 231, YAC 1, U 266B1, SH-SY5Y and CHO (e.g. CHO-K1).

The present invention provides a method for producing a retroviral vector particle comprising, for example, transfecting a host cell with retroviral vector components (envelope construct, packaging construct and transfer vector) to produce a packaging cell line and culturing said transformed packaging cell under conditions effective to produce a retroviral vector particle. Any suitable transfection methods can be used in the vector particle manufacturing process including electroporation, calcium phosphate transfection, PEI polymer mediated transfection, fecturin or lipid-based transfection methods. A preferred transfection method uses the lipid transfection reagent FuGENE® 6 from Roche (Jacobsen et al., 2004). Cells can be co-transfected (i.e., using both helper and transfer vectors), or they can be transfected in separate steps, where each step involves the introduction of a different vector component. Alternatively, host cells can be stably transfected and selected for the expression of the helper vectors.

The cell line used to manufacture the retroviral vector particle can be modified to enhance vector particle production. For example sequences that code for cellular or viral enhancers can be engineered into cell lines (e.g. using additional plasmid vectors), to enhance the level of virus product, or sequences for cellular transactivator proteins including e.g. NF-κB, UV light responsive factors and T cell activation factors.

Cells are cultured under conditions effective to produce retroviral vector particles such as appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including cell media, substrates, oxygen, carbon dioxide, glucose and other sugar substrates, serum, growth factors, etc.).

The retroviral vector particle is preferably secreted into the cell culture medium where it can be recovered and optionally enriched or purified using centrifugation and/or filtration methods such as flow-through ultracentrifugation, high-speed centrifugation or tangential flow filtration.

The present invention also provides method of manufacturing polypeptides using retroviral vector particles such as those described herein. Generally the method comprises the steps of transducing a host target cell with a retroviral vector particle to form a transduced host cell, wherein the vector particle comprises an expressible heterologous polynucleotide coding for a heterologous polypeptide of interest, culturing the transduced host cell under conditions effective to produce the polypeptide of interest; isolating the polypeptide from the host cell e.g. from the culture medium when a polypeptide is secreted into the culture medium. The heterologous polynucleotide sequence coding for the polypeptide can comprise any further sequences necessary for transcription, translation and/or secretion into the medium (e.g. secretory sequences). Any host cell can be transduced in accordance with the present invention. In general, these host cells are capable of growth and survival when placed in either monolayer culture or in suspension culture in a medium containing the appropriate nutrient and growth factors, as described in more detail below. Typically, the cells are capable of expressing and secreting large quantities of a particular protein of interest into the culture medium. Examples of suitable mammalian host cells include, but are not limited to: CHO, bovine mammary epithelial cells, monkey kidney CV1 line transformed by SV40 (COS-7, ATCC CRL 1651), HEK 293 (Graham et al., 1977), baby hamster kidney cells (BHK, ATCC CCL 10), mouse sertoli cells (TM4; Mather et al., 1980), monkey kidney cells (CV1, ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumour (MMT 060562, ATCC CCL 51), TR1 cells (Mather et al., 1982), MRC 5 cells, FS4 cells, rat fibroblasts (208F cells), a human hepatoma line (Hep G2) and MDBK cells, providing that these host cells express the Rec1 receptor either ectopically or recombinantly. In a preferred embodiment of the present invention, the host cell line is a rodent cell line, preferably CHO (including CHO-S, CHO-K1, CHO-GS, CHO DG44, CHO T-REx™, CHO/-DHFR etc) or the cell line BHK.

In a further embodiment of the present invention, the host cell is engineered to over express the ecotropic MLV receptor Rec1. This can be achieved by transfecting the host cell of choice with a vector particle comprising the gene coding for the Rec1 receptor (GenBank: M26687.1) or a portion of this coding sequence that results in the generation of a functional Rec1 receptor. The nucleic acid and amino acid sequences for Rec1 receptor are shown in the attached sequence listing and have SEQ ID Nos: 31 and 32, respectively. As a result, host cells that are resistant to infection by ecotropic MLV will become permissive to infection by this virus on expression of the Rec1 receptor.

Siess et al (1996) reported that over expression of Rec1 (mCAT-1) in CHO cells and exposure to non-infectious ecotropic MLV particles produced by a packaging cell line, resulted in cell syncytia formation and subsequent cell death. However, this has not been observed for CHO cells recombinantly expressing Rec1 when exposed to retroviral vector particles of the present invention.

In a preferred embodiment of the present invention, the host cells are transfected with a Rec1 receptor expression construct, so that the Rec1 receptor is recombinantly expressed.

Retroviral vector particles according to the present invention can be prepared routinely and as described above. In one embodiment, the envelope protein of the vector particle is selected for its ability to recognise a target host cell expressing the Rec1 receptor. In a preferred embodiment, the envelope protein is from PVC-211 MLV.

As shown in the Examples, an increase in transduction efficiency of over 100 fold can be achieved when transducing a host cell line expressing the Rec1 receptor with a retroviral vector comprising the PVC-211 MLV envelope. The Rec1 receptor may already be expressed by the host cells and/or the cell line can be engineered to express the Rec1 receptor. A method of the present invention utilises a host cell expressing the Red receptor. A host cell engineered to over express the Red receptor i.e. recombinant expression, is also encompassed within the present invention, for use in methods of the invention.

Any suitable or desired heterologous sequence can be expressed using a method of the present invention, including, e.g. but not limited to, vaccines, interferons, erythropoietin, Factor VIII, clotting factors, antibodies and fragments thereof (e.g., including single chain, Fab and humanized), insulin, chemokines, cytokines, growth factors, angiogenesis modulatory factors, apoptosis modulatory factors.

A preferred embodiment of the present application provides methods of producing antibodies. For example, methods are provided to produce monoclonal antibodies (e.g., human, mouse, and other mammalian types) without the need for hybridomas or animal models. In a non-limiting example (e.g. Example 16), two retroviral vector particles are engineered, one expressing the heavy antibody chain and the second expressing the light antibody chain. The constant areas of the genes are derived from the human (or other species if desired) immunoglobulin gene (e.g. IgG, IgH, IgM or other type of Ig), either allowing secreted (e.g. sIgH) or allowing membrane bound antibody expression. The variable areas of the genes can be modified or degenerated to create diversity. The degenerate sequence can be obtained by any suitable techniques that is known in the art and cloned into the retroviral transfer vector particle to create a library of vector particles that express either the heavy or light immunoglobulin molecules. The antibodies can be produced by transducing host cells with both vector particles to produce functional antibodies that contain both heavy and light chains, either simultaneously or sequentially, in any order. Alternatively, the heavy and light chains of an antibody can be cloned into the same retroviral vector particle by utilising a bicistronic vector (see Example 17).

To increase yield or expression levels of the protein of interest in host cells, the retroviral vector particles of the present invention can be used to transduce host cells multiple times. It is demonstrated in Examples 15 and 17 using host cells recombinantly expressing the Red receptor, that transduction of host cells three times can result in a significant increase in protein yield compared to target cells transduced only once. Protein yields of up to 11.8 mg/L have been demonstrated (see Example 17) following three rounds of transduction. Also transduction of host cells either once or three times with retroviral vector particles of the invention results in increased protein yields compared to transfected host cells.

In addition to expressing the protein of interest, the retroviral vector particle can be engineered to facilitate production of the protein of interest, or to increase its yield. Such genes can code for other promoters, enhancers, locus control regions (LCRs), matrix attached region sequences (MARs), the woodchuck hepatitis virus posttranscriptional regulatory element (WRPE; Zufferey et al., 1999), insulators, oncogenes such as ras and myc, anti-apoptotic genes such as Bcl-2 and bcl-x(L), other cytostatic genes such as p21, p27, p53175P and p53 and differentiation factors such as CCAAT/enhancer-binding protein alpha.

Host cell lines can be cultured in a suitable culture media that provides a balance of buffering and osmoregulating substances, trace elements, amino acids, vitamins, lipids and nutrients required for long-term cultivation of mammalian cells in vitro. Traditionally cell culture medium was supplemented with calf or cattle serum; however many culture media are now available that are free of bovine components.

In the cell culture process, the host cells may be grown as either anchorage dependent or in suspension. In vitro systems for anchorage-dependent cells range from T-flasks and roller bottles through to fluidised or fixed bed bioreactors. Culture medium and aeration is provided continuously or at intervals by exchange of medium and gas or perfusion of the bioreactors. Alternatively, a suspension culture can be used which is often the culture process of choice for the production of therapeutic antibodies in large quantities. For low liter quantities, shake flasks or spinner vessel systems can be used and for larger quantities of up to 20,000 L, continuous stirred tank reactors are commonly used.

Standard cell cultivation can be by a batch process where a seed cell suspension and medium are added to the bioreactor at the start of the process and the cells are cultivated for a set period of time under suitable conditions without any further manipulations. Alternatively, a fed-batch process or continuous perfusion fermentation can be used where specific cell culture additives are added during the cultivation period generally leading to enhanced cell growth, higher cell densities, less nutrient limitations and overall higher product yields. This process is commonly used for the manufacture of therapeutic antibodies.

Use of retroviral vector particles of the present invention can result in high levels of heterologous protein expression, e.g., from about 0.01 to 0.1 to 0.3 mg/ml to about 5-10 mg/ml, or more, of recombinant heterologous protein per ml of unprocessed culture media, when such proteins are secreted into the culture media.

To harvest products from mammalian cell cultures, methods such as filtration, centrifugation and adsorption can be used. Filtration separates the products from the host cells, cell debris and large particles and can be either a static or dynamic process. Tangential flow filtration (TFF) can be used to enhance the separation of cells and large particles. Centrifugation and adsorption (e.g. expanded bed adsorption) can be used as an alternative to membrane filtration or filter-based separation, respectively. Further downstream processing steps are required for the purification of the final product and these may include: ultra/diafiltration, affinity chromatography, hydroxyapatite chromatography, gel electrophoreisis, dialysis, virus clearance, hydrophobic interaction chromatography (HIC), ion exchange chromatography (IEC), cation exchange chromatography and/or anion exchange chromatography, depending on the polypeptide or antibody to be recovered.

In the following non-limiting examples, the present invention is explained in more detail.

EXAMPLES

Example 1

Cloning of Expression Vectors

The detailed cloning strategy of expression vectors for viral structural proteins and viral receptors of different designs that can be used in the present invention is described below. Also described are methods for the stable maintenance of these vectors in target cells and producer cells, using antibiotic resistance markers.

1.1 Construction of Parental Expression Vectors

As a starting point for the construction of expression vectors the commercially available vectors pIRESneo and pIRESbleo were used (BD-Clontech, Mountain View, Calif.). These parental vectors contain a neomycin and bleomycin resistance marker gene respectively, flanked by unique restriction sites for XbaI and XmaI. In addition, these vectors contain the CMV IE promoter driving expression of the gene of interest and the resistance gene. 3' of the promoter a simple multiple cloning site (MCS) for insertion of genes of interest to be expressed is followed by a synthetic intron and an internal ribosome entry signal (IRES) located just 5' of the respective resistance gene. The derivates of these vectors described below enable the selection of cells in culture expressing a gene of interest in the presence of respective antibiotics, since the coding regions for the gene of interest and the antibiotic resistance marker are located on one mRNA linked by an IRES. This mechanism is referred to as 'geno-/phenotype-coupling'. The non-limiting example of the construction of the expression vector pIRESpuro is described below.

pIRESneo was digested using the restriction enzymes XbaI and XmaI. After electrophoresis of the plasmid DNA, the resultant XbaI-XmaI-DNA fragment of the vector backbone (pIRES) depleted of the resistance gene was extracted using NucleoSpin Extract II (Macherey-Nagel).

PCR for the puromycin resistance gene (puroR; SEQ ID Nos: 7 & 8) was performed under the following conditions. The reaction mixture consisted of 100 ng template (pM-SCVpuro, Clontech), 5 µl Pfx buffer (10-fold), 1 µl Mg$^2$SO$_4$ (30 mM), 7 µl dNTP (2 mM), 0.7 µl Pfx (Invitrogen) and 1 µl of each primer (10 µM, nucleotide sequences are given below). Water was added to the reaction mixture to result in a total volume of 50 µl. Primers used for amplification of the puromycin resistance gene (puroR; SEQ ID Nos: 7 & 8) were:

```
                        (Puro XmaI forward; SEQ ID No: 5)
5'-ATAACCCGGGATGACCGAGTACAAGCCCACGGTGC-3'
and
                        (Puro XbaI reverse; SEQ ID No: 6)
5'-ATTATCTAGATCAGGCACCGGGCTTGCGGGTC-3'.
```

The temperature conditions for puroR amplification were 95° C. for 3 minutes, followed by 25 cycles of 95° C. for 30 seconds, 58° C. for 30 seconds, 68° C. for 1 minute. The amplification was terminated after an additional 7 minutes at 68° C. After electrophoresis of the PCR products the amplicon was extracted as described and digested with XbaI and XmaI. Finally, the resulting XbaI-XmaI-digested puromycin resistance gene fragment was ligated into the above-mentioned pIRES fragment digested accordingly. The resultant vector pIRESpuro is shown in FIG. 1a, with the sequence depicted in FIG. 1h and SEQ ID No: 42. Further derivates of this vector were generated accordingly, only differing in the reporter gene. Primers used for the amplification of the other reporter genes were as follows: For the hygromycin resistance gene (hygro; SEQ ID Nos: 11 & 12):

```
                        (BSPHI/XMAI HYGRO+; SEQ ID No: 9)
5'-AATTAATCATGACCCGGGACCATGAAAAAGCCTGAACTCACCGCGA

C-3'
and (XBAI/SALI/NOTI HYGRO-; SEQ ID No: 10)
5'-AATTAAGTCGACGCGGCCGCTCTAGACTATTCCTTTGCCCTCGGAC

GAGTG-3'.
```

For the blasticidin resistance gene (bsr; SEQ ID Nos: 15 & 16):

```
                        (BSR XMAI +; SEQ ID No: 13)
5'-AATTAACCCGGGACCATGAAAACATTTAACATTTCTCAACAAGATC

TAG-3'
and
                        (BSR SPEI -; SEQ ID No: 14)
5'-AATTAAACTAGTTTAATTTCGGGTATATTTGAGTGGAATGAG-3'.
```

Upon restriction and purification the resultant amplicons were inserted into the backbone as described above to give the constructs pIREShygro and pIRESbsr, respectively.

As will be appreciated by a person skilled in the art, the present invention can be performed using different expression vector designs containing other antibiotic resistance genes (e.g. hygromycin (SEQ ID Nos: 11 & 12), blasticidin (SEQ ID Nos: 15 & 16), bleomycin (SEQ ID Nos: 17 & 18), neomycin (SEQ ID Nos: 19 & 20), etc), other reporter genes such as fluorescence proteins (e.g. GFP (SEQ ID Nos: 21 & 22), YFP (SEQ ID Nos: 23 & 24), etc) and/or cell surface markers (e.g. truncated NGFR (SEQ ID Nos: 25 & 26), truncated CD7 (SEQ ID Nos: 27 & 28), etc).

1.2 Construction of Vectors for the Expression of the Ecotropic Murine Leukaemia Virus Receptor (Rec1).

Total RNA was isolated from murine 3T3 cells using TRI-COL (Sigma) according to the manufacturers' instructions. 0.5 µg of RNA served as a template for RT-PCR using the OneStep RT-PCR kit (Qiagen) and 10 pmol each of the primers

```
                        (eMLV-R NotI forward; SEQ ID No: 29)
5'-TTTAAGCGGCCGCATGGGCTGCAAAAACCTGCTCGGTC-3'
and (eMLV-R BamHI reverse; SEQ ID No: 30)
5'-TTTAAGGATCCTCATTTGCACTGGTCCAAGTTGCTGTC-5'.
```

The temperature conditions were 50° C. for 30 minutes, 25 cycles of 95° C. for 1 minute, 60° C. for 15 seconds and 72° C. for 2 minutes. Final extension was performed at 72° C. for 5 minutes.

Figure 1B:
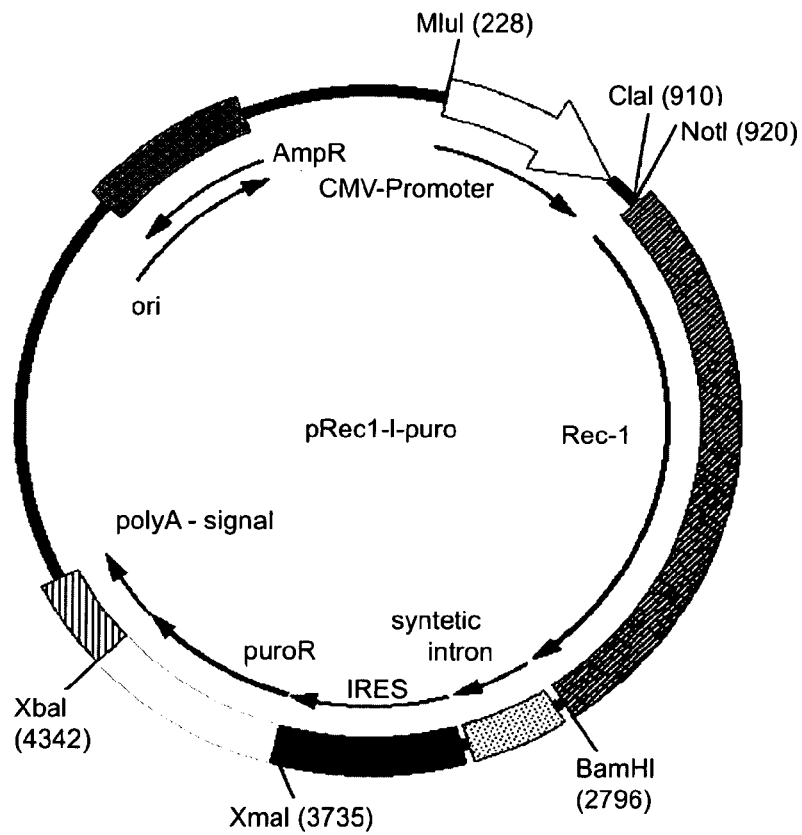
Figure 1C:
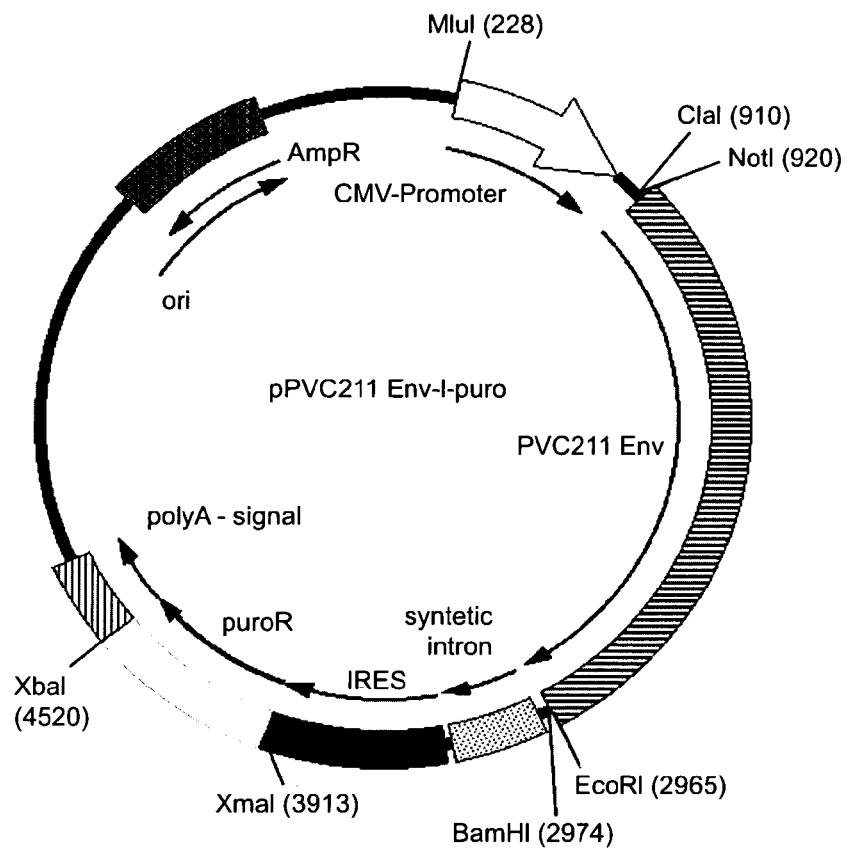
Figure 1D:
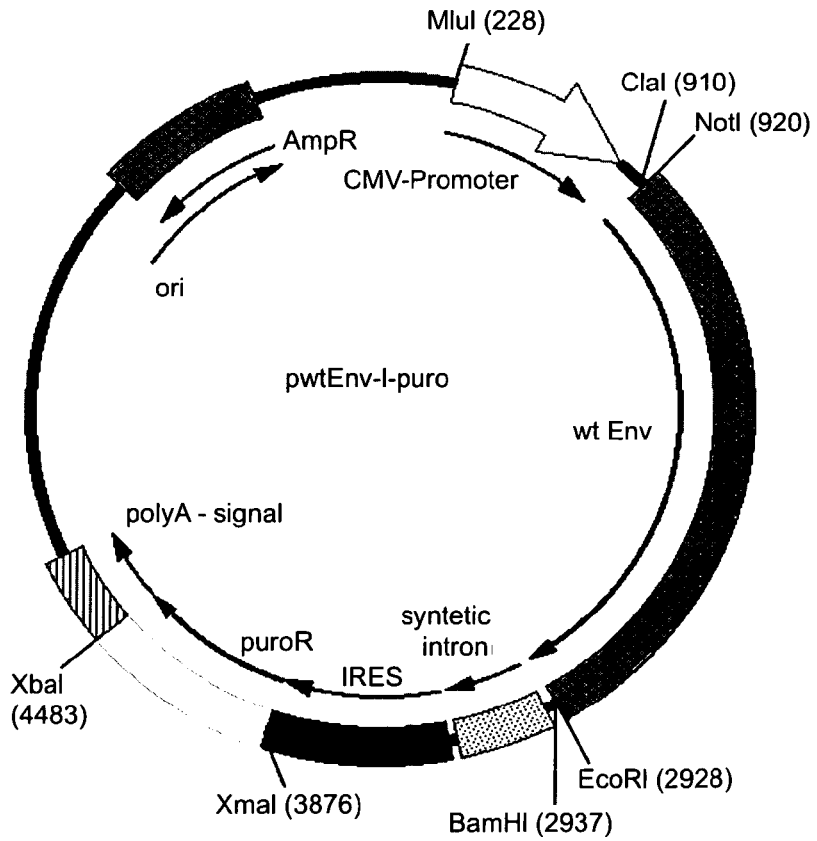

The resulting amplicon and the vectors pIRESbleo and pIRESneo were digested with NotI and BamHI. Ligation of the amplicon into both vectors resulted in the Rec1-expression vectors Rec1-I-neo and pRec1-I-bleo, respectively. Further Rec1-expression vectors containing different reporter genes were constructed by digestion of pRec1-I-neo and -bleo with NotI and BamHI and insertion of the Rec1 cDNA into respective recipient vectors digested accordingly. The genetic organization of pRec1-I-puro is shown in FIG. 1b. The nucleic acid and amino acid sequences for the Rec1 receptor have SEQ ID Nos: 31 & 32 respectively, as shown in the accompanying sequence listing.

1.3 Construction of Vectors Containing the Envelope Coding Region of Ecotropic Murine Leukaemia Virus Molecular Clone Pvc-211.

The envelope coding region of PVC-211 (SEQ ID No: 1; GenBank: M93134.1 "env" gene; Masuda et al., 1992) was synthesised to include a stuffer sequence (5-TTAATTAATT-3'; SEQ ID No: 33), a NotI-restriction motif and a Kozak-sequence 5' of the ATG-initiation codon and a EcoRI-restriction motif and a stuffer sequence (5'-TTAATT-3'), 3' of the TAA-stop codon. Upon digestion with NotI and EcoRI the env gene was inserted into pIRESpuro and digested accordingly.

1.4 Construction of Vectors Containing the Gag/Pol Coding Region of Ecotropic Murine Leukaemia Virus (MLV)

The gag/pol coding region of ecotropic MLV (Mo-MLV; Shinnick et al., 1981; SEQ ID No: 36) was amplified by PCR using the primers:

```
                        (Kozak Gag/Pol, SEQ ID No: 34)
5'-AATAAGCGGCCGCGCCGCCACCATGGGCCAGACTGTTACCACTCCC TTAAG-3'
and (MLVgp RI rev, SEQ ID No: 35)
5'-ATGAATTCTTAGGGGGCCTCGCGGGTTAACC-3'.
```

Figure 1E:
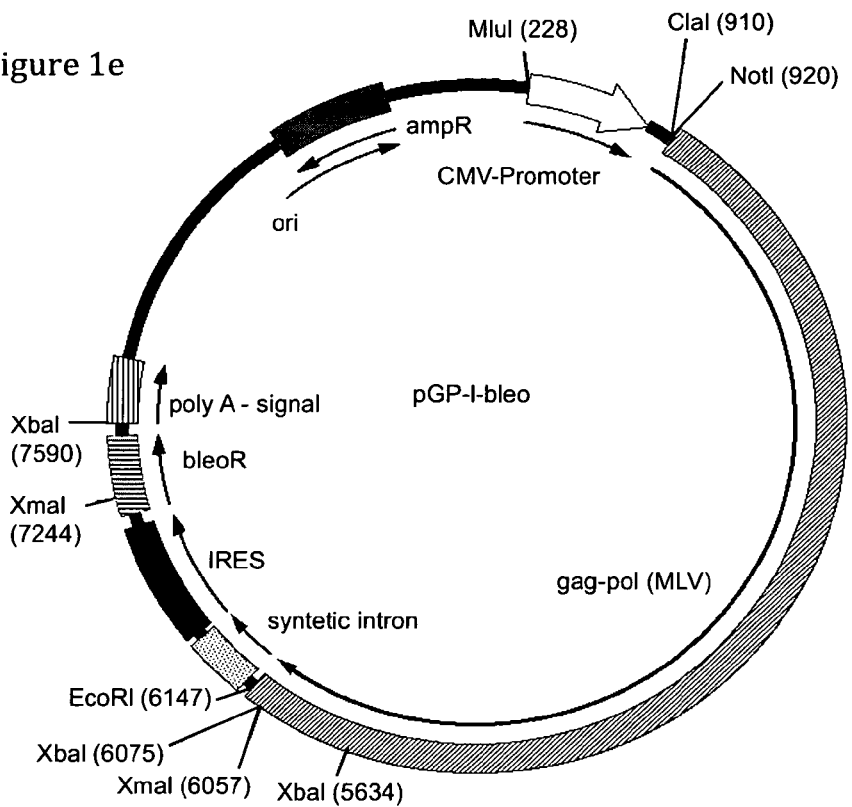

The reaction mix consisted of 50 ng template (Shinnick et al., 1981), 3 µl Pfx buffer (10-fold), 0.6 µl Mg$^2$SO$_4$ (30 mM), 4.5 µl dNTP (2 mM), 0.4 µl Pfx (Invitrogen), and 0.5 µl of each primer (10 µM). Water was added to the reaction mixture to result in a total volume of 30 µl. Temperature conditions were 94° C. for 3 minutes, 25 cycles of 94° C. for 30 seconds, 66° C. for 30 seconds, 68° C. for 6 minutes followed by a final extension at 68° C. for 10 minutes. After electrophoresis and extraction of the PCR products the DNA fragment was inserted into pSC-B (Stratagene). The resultant plasmid SC-Kozakgp was digested with NotI and EcoRI and upon electrophoresis and extraction inserted into pIRESbleo, previously digested according to Example 1.1. A schematic illustration of the genetic structure of this plasmid is shown in FIG. 1e.

1.5 Further Variants of Expression Vectors Utilizing the Murine Promoter of the Housekeeper Gene Phospho Glycerol Kinase (Ppgk)

As shown in FIG. 1a, the pIRES expression vectors harbour the human CMV IE promoter to facilitate gene of interest and reporter gene expression. Alternatively, derivatives were constructed, which utilize the murine promoter of the housekeeper gene phospho glycerol kinase (Ppgk; SEQ ID NO: 40). Murine Ppgk was amplified by PCR using the primers:

```
                        (PGK MluI/NruI+; SEQ ID No: 38)
5'-AATTAAACGCGTTCGCGACAATTCTACCGGGTAGGGGAGGCGC-3'
and (PGK Cla-; SEQ ID No: 39)
5'-AATTAAATCGATGGTGGCGGGATGCAGGTCGAAAG-3'
```

Figure 1F:
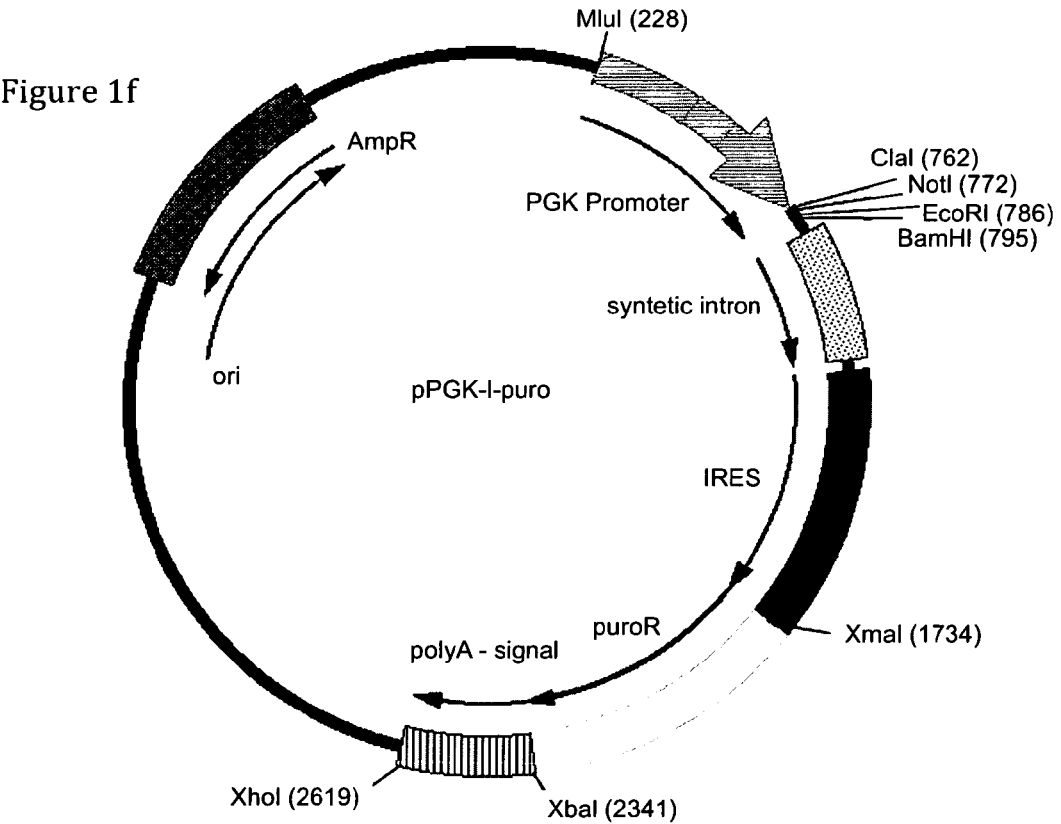
In FIG. 1(f), the promoter originates from the murine phospho-glycerol kinase housekeeper gene (Ppgk; grey dashed box).

The reaction mix contained 1 µl of both primers (10 pM), 4 µl HF-Buffer (5×), 2 µl dNTPs (2 mM), 0.2 µl of PHUSION polymerase (Finnzym) and 100 ng template of a plasmid encompassing the murine Ppgk (MigR1-Ppgk, described below) in a total volume of 20 μl. The PCR product was subjected to electrophoresis and extraction as described above and inserted into pSC-B (Stratagene) giving rise to the construct pSC-MluI/NruI-Ppgk-ClaI. This vector was digested with MluI and ClaI. The MluI-ClaI-DNA fragment was inserted into pIRESpuro containing the reporter puromycin resistance gene (puroR; SEQ ID Nos: 7 & 8). The resultant vector pPpgk-I-puro is shown in FIG. 1f. The nucleic acid sequence of murine Ppgk has SEQ ID No: 40.

1.6 Construction of Mlv-Based Transfer Vectors Containing the Promoters of the Murine Phospho Glycerin Kinase (Ppgk) and Murine V-Kappa Gene Promoter ($Pv_\kappa$)

Figure 1G:
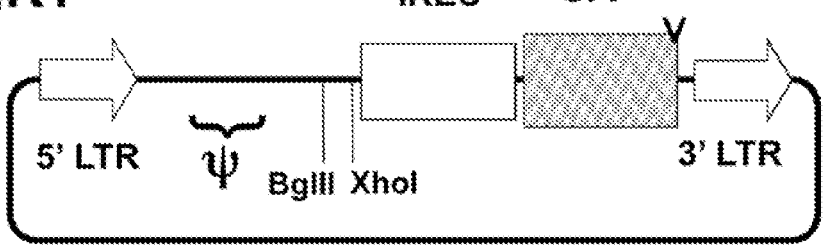
FIG. 1g: Schematic illustration of the retroviral transfer vectors MigR1 and its derivates MigR1Ppgk and MigR1Pv$_\kappa$. The parental vector MigR1 encompasses the flanking long terminal repeats (5' and 3' LTR), the packaging signal (psi/$\Psi$) required for the packaging of mRNA-transcripts of the transfer vector into MLV-derived vector particles, an internal ribosome entry site (IRES) and the reporter gene of green fluorescence protein (GFP). Unique restriction-sites for BglII and XhoI 5' of the IRES are indicated and were used for the insertion of the promoter of the murine phospho glycerol kinase gene (Ppgk) or the human promoter of the variable kappa chain genes (Pv$_\kappa$). A black arrow indicates the position of the stop codon of the reporter gene.
Figure 1G:
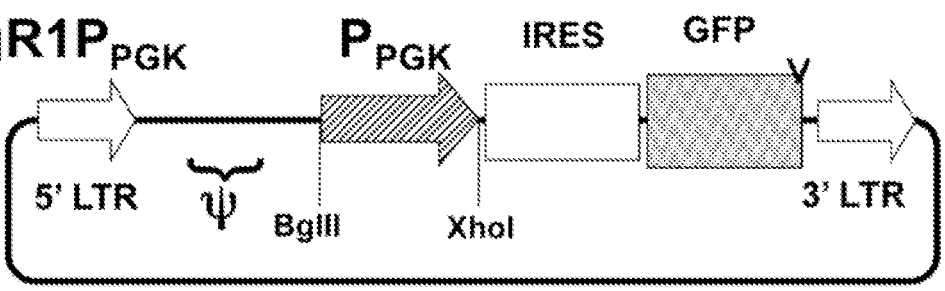
Figure 1G:
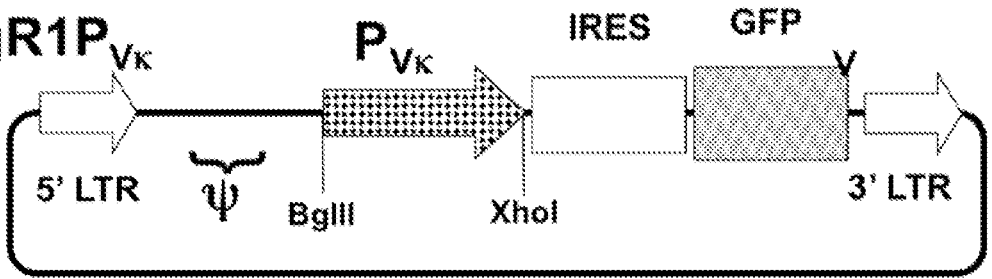

All MLV-based transfer vectors described in the Examples of the present invention were either MigR1 (Pear et al., 1998; http://www.lablife.org/p?a=vdb_view&id=g2.531Ogh0E_Yc2k4vlr3OZM.EUaXE-; FIG. 1i; SEQ ID NO: 43), which drives expression exclusively using the MLV-promoter encompassed in the 5'LTR or were derivates thereof additionally containing the promoters of the murine phospho glycerol kinase (Ppgk) and/or murine V-kappa gene ($Pv_\kappa$; SEQ ID No: 41) optionally with or without the murine kappa intron enhancer element (KiE; SEQ ID No: 48). As illustrated in FIG. 1g, the BglII-XhoI-fragments encompassing these murine promoters were inserted between the unique restriction motifs of XhoI and BglII, located 5' of the internal ribosome entry site (IRES) and therefore driving the expression of the reporter gene GFP.

1.7 Construction of MLV-Based Transfer Vectors Containing the Promoters of the Murine Ppgk, a His-Tagged $Vegf_{121}$ and a Puromycin Resistance Gene cDNA from human peripheral blood lymphocytes was generated using standard RT-PCR techniques (Sambrook et al, 2001). The cDNA served as a template for the amplification of the coding region of human vesicular endothelial growth factor variant 121 ($VEGF_{121}$; SEQ ID No: 46) using PCR employing the proof-reader polymerase Pfx and the oligonucleotides

```
                        VEGF121 Not Koz (SEQ ID No: 44)
5'-aataagcggccgcgccaccatgaactttctgctgtcttgggtgcat tgg-3':
and VEGF121 6xHis R1 rev (SEQ ID No: 45)
5'ataattgaattctcaatgatgatgatgatgatgatctccccgcctcg gcttgtcacattttttcttgtc-3':.
```

The resultant amplicon harbouring recombinant restriction sites for NotI and EcoRI, a Kozak-sequence, and a His-tag was inserted first into the cloning vector pSC-B (Sratagene). The resultant vector was termed pSC-$VEGF_{121}$-6×His. Using DNA sequencing, accuracy of the inserted DNA fragment was shown. Subsequently, pSC-$VEGF_{121}$-6×His was digested using the restriction enzymes NotI and EcoRI and the VEGF variant coding region was inserted into the recipient vector pIRESgfp, previously digested accordingly, resulting in the vector pVEGF-hu$VEGF_{121}$-6×His. From this vector, the region encoding the His-tagged $VEGF_{121}$ variant was obtained by restriction digest employing the enzymes NotI and EcoRI. The plasmid pMigR1Ppgk-$VEGF_{121}$-6×His-I-puro depicted in FIG. 1j and FIG. 14a, was generated upon insertion of the coding region into the retroviral transfer vector pMigR1-Ppgk-I-puro, digested accordingly.

Figure 15A:
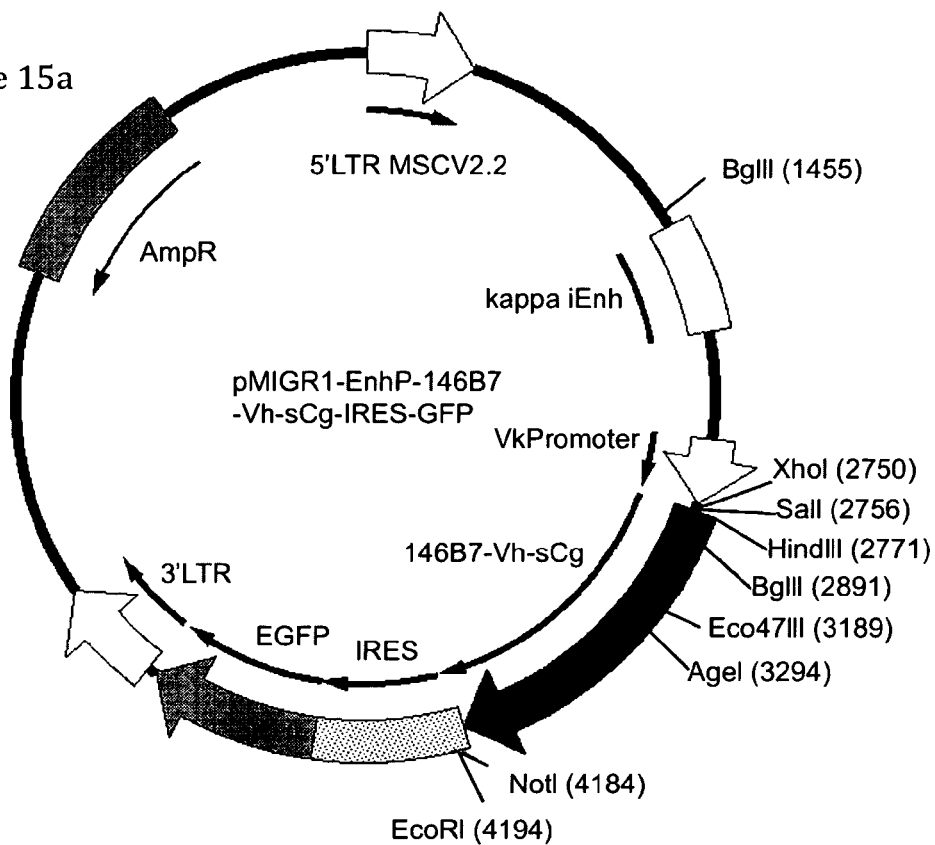
FIG. 15: Shown in FIG. 15*a* is the construct pMigR1-EnhP-146B7-Vh-sCg-IRES-GFP containing the murine kappa intron enhancer element (KiE) and the murine Vkappa promoter (Pv$_K$). This promoter drives the expression of the heavy chain of an anti-IL-15 antibody 146B7 comprising the Vh coding region, flanked by the restriction sites for HindIII and Eco47III, and the IgH constant region (sCg). An IRES located between the 146B7-Vh-sCg and the GFP gene couples their expression from the same mRNA transcript. This transcript is flanked by 5' and 3' LTRs.
FIG. 15*b* shows the construct pMigR1-EnhP-146B7-Vk-Ck-IRES-bcl2 containing the murine kappa intron enhancer element (KiE) and the murine Vkappa promoter (Pv$_K$). This promoter drives the expression of the light chain of an anti-Il-15 antibody 146B7 comprising the Vk coding region, flanked by the restriction sites for HindIII and EcoRI, and the kappa constant region (Ck). An IRES located between the 146B7-Vk-Ck and the bcl2A gene couples their expression from the same mRNA transcript. This transcript is flanked by 5' and 3' LTRs.

1.8 Construction of Mlv-Based Transfer Vectors Containing an Anti IL-15 Antibody Heavy or Light Chain or Both For the generation of the transfer vector pMigR1-EnhP-146B7-Vh-sCg-IRES-GFP (FIG. 15a), the coding sequence for the heavy chain of the anti-IL-15 antibody 146B7 (146B7 Vh, SEQ ID No: 49 and secretable IgH constant region (sCg), SEQ ID No: 51 (derived from joining by 210-503, 892-936, 1055-1384 and 1481-1803 of the human IGHG1 gene, Accession No: J00228)) was cloned into the HindIII and EcoRI sites of the MigR1 vector described in Example 1.6 above, containing the enhancer element KiE (SEQ ID No: 48) and the promoter $Pv_\kappa$ (SEQ ID No: 41).

Figure 15B:
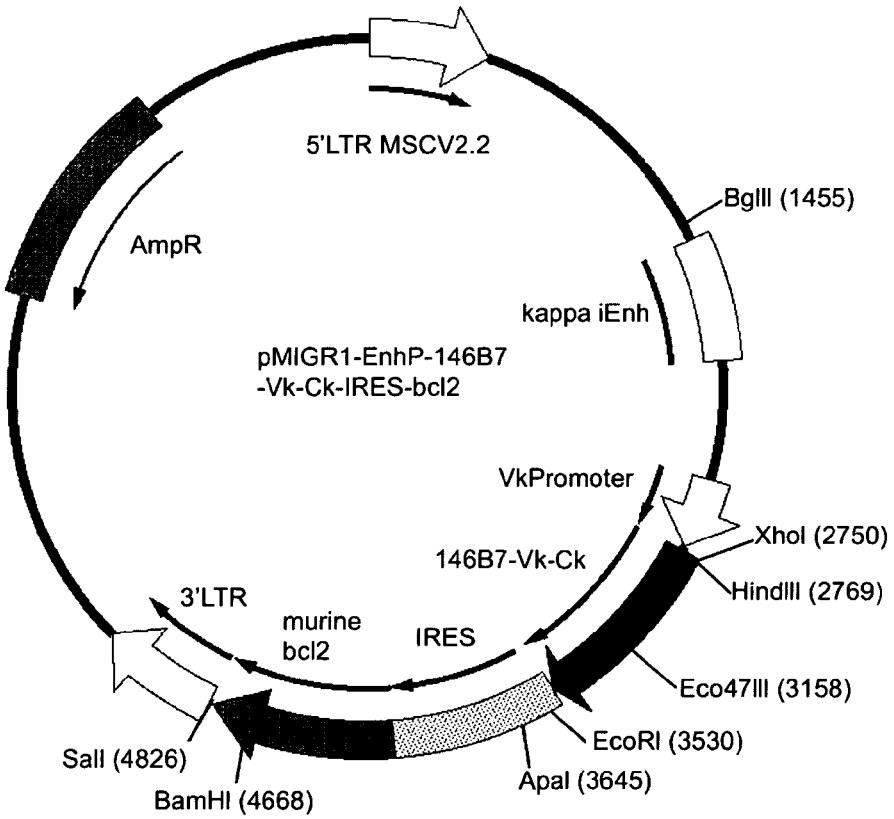

The light chain transfer vector pMigR1-EnhP-146B7-Vk-Ck-IRES-bcl2 (FIG. 15b) was generated by cloning the coding sequence for the light chain (Vk-Ck) of anti-IL-15 antibody 146B7 (146B7 Vk, SEQ ID No: 53 and kappa constant region (Ck), SEQ ID No: 55 (bp 336-656 of the human IGKC gene, Accession No: J00241)) into the HindIII and EcoRI sites of the MigR1 vector, which is described in Example 1.6 above. The vector also contained the enhancer element κiE (SEQ ID No: 48) and the promoter $Pv_\kappa$ (SEQ ID No: 41). The murine bcl2A gene replaced the EGFP ORF in the MigR1 vector. The ORF of murine bcl2A (SEQ ID No: 63) was isolated and amplified from mouse spleen mRNA by RT-PCT using the following primers, designed and based on the published NCBI-Genbank sequences M16506 and L31532 and containing restriction enzyme recognition sites (in uppercase letters) for NheI and MluI:

```
5'-attGCTAGCatggcgcaagccgggagaacagggtatgataac-3'
(SEQ ID No: 61; binds to position 1821-53 of
M16506)
and 5'-cgcACGCGTcacttgtggcccaggtatgcacccagagtg-3'
(SEQ ID No: 62; binds to position 506-535 of
L31532).
```

Figure 17:
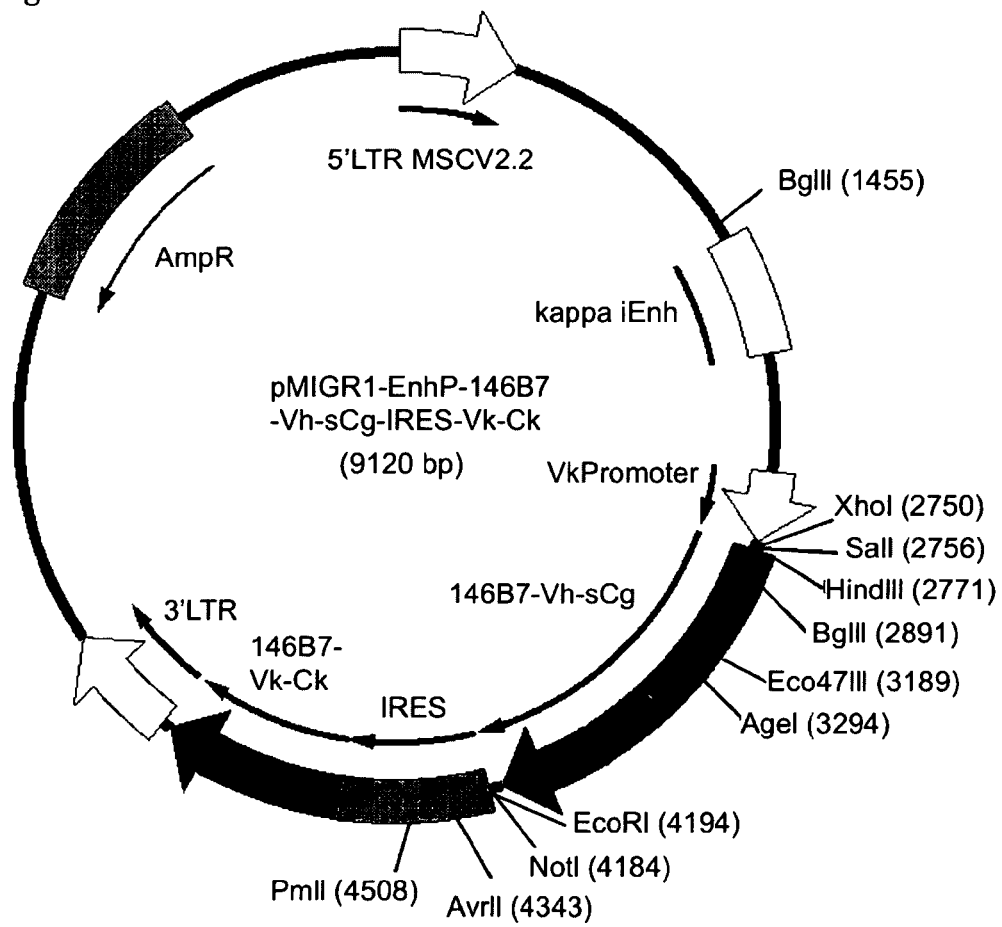
FIG. 17: This figure shows the construct pMigR1-EnhP-146B7-Vh-sCg-IRES-Vk-Ck, a bicistronic vector containing the murine kappa intron enhancer element (κiE) and the murine Vkappa promoter (Pv$_K$). This promoter drives the expression of the heavy and light chain of an anti-1'-15 antibody 146B7. An IRES located between the 146B7-Vh-sCg and the 146B7-Vk-Ck couples their expression from the same mRNA transcript. This transcript is flanked by 5' and 3' LTRs.

For the construction of a bicistronic transfer vector containing an anti IL-15 antibody heavy and light chain, the EGFP ORF of the heavy chain transfer vector pMigR1-EnhP-146B7-Vh-sCg-IRES-GFP was replaced by the coding region for the light chain of 146B7 (Vk-Ck; described above) resulting in vector pMigR1-EnhP-146B7-Vh-sCg-IRES-Vk-Ck as is shown in FIG. 17.

1.9 Construction of MLV-Based Transfer Vectors Containing Heavy or Light Chains of Recombinant Human Anti-IL-1β B Cell Receptors To construct the transfer vector pMigR1-EnhP-SK48E26-Vh-sCg-IRES-GFP, the Vh coding region of the 11-113 antibody SK48E26 (WO 95/01997; Young et al.; SEQ ID No: 57) was cloned into the HindIII and EcoRI site of vector pMigR1-EnhP-146B7-Vh-sCg-IRES-GFP, described in Example 1.8 above, replacing the 146B7-Vh coding region.

Similarly, to construct the transfer vector pMigR1-EnhP-SK48E26-Vk-Ck-IRES-bcl2, the Vk coding region of the IL-1β antibody SK48E26 (WO 95/01997; Young et al.; SEQ ID No: 59) was cloned into the HindIII and EcoRI site of vector pMigR1-EnhP-146B7-Vk-Ck-IRES-bcl2, described in Example 1.8 above, replacing the 146B7-Vk coding region.

1.10 Construction of MLV-Based Transfer Vectors Containing the Coding Regions for the Cytokines IL-6 and TNFα and the Chemokine CCL5

For the generation of the transfer vector pMigR1-EnhP-IL-6-IRES-GFP, the coding sequence for the cytokine IL-6 (SEQ ID No: 64; by 117-755 of human Il-6 Accession No: NM 000600) could be cloned into the HindIII and EcoRI sites of the MigR1 vector, described in Example 1.6 above, which contains the enhancer element KiE (SEQ ID No: 48) and the promoter $Pv_\kappa$ (SEQ ID No: 41).

For the generation of the transfer vector pMigR1-EnhP-INFα-IRES-GFP, the coding sequence for the pro-inflammatory cytokine TNFα (SEQ ID No: 65; by 170-871 of human TNFα Accession No: NM 000594) could be cloned into the HindIII and EcoRI sites of the MigR1 vector, described in Example 1.6 above.

For the generation of the transfer vector pMigR1-EnhP-CCL5-IRES-GFP, the coding sequence for the chemokine (C—C motif) ligand 5 (CCL5) (SEQ ID No: 66; by 68-344 of human CCL5 Accession No: NM 002985) could be cloned into the HindIII and EcoRI sites of the MigR1 vector, described in Example 1.6 above.

Example 2

Cultivation and Establishment of Cell Lines Stably Expressing the Receptor of Ecotropic MLV (Rec1)

All CHO cells (CHO-S (Invitrogen), CHO T-REx™ (Invitrogen), CHO-K1 (DSMZ)) and murine pre-B 1624-5 cells were expanded in IMDM supplemented with 10% FCS and 50 µM beta-mercapthoethanol. Human fibrosarcoma HT1080, HEK and BHK cells were cultured in DMEM supplemented with 10% FCS and L-Glutamine (2 mM). To establish cell lines stably expressing the ecotropic receptor Rec-1, CHO, BHK and HT1080 cells were seeded at a density of $1\times10^5$ cells in 2 ml of respective media in six-well tissue culture dishes (Nunc), 5 to 24 hours prior to transfection. 1 µg to 3 µg of the respective Rec1-encoding pIRES-variants were transfected (see FIG. 1b) using FuGENE®6 (Roche) following the manufacturers' instructions. Two days post transfection, transfected adherent cells were detached using 1 mM EDTA/PBS, suspended and seeded in 15 cm dishes. The following day antibiotic-containing media were applied to the cells. The concentrations of antibiotics used for the constructs is as indicated in the following cell line designations. For the generation of cell lines using pRec1-I-neo 400 µg/ml of G418 (neomycin; Invitrogen) was used for HT1080 cells, 750 µg/ml for CHO T-REx™ cells and 1 mg/ml for CHO-S and CHO-K1 cells. For the generation of cell lines using pRec1-I-puro, puromycin was used at 1 µg/ml for CHO T-REx™ cells, 5 µg/ml for CHO-K1 cells and 10 µg/ml for CHO-S cells and 1 µg/ml for BHK cells. After five to seven days resistant bulk populations were obtained.

Example 3

Generation of Ecotropic MLV Vector Particles and Transduction of Target Cells

For the generation of ecotropic MLV-based vector particles a triple co-transfection approach employing human embryonic kidney (HEK) cells was used. HEK cells were seeded at a density of $3\times10^6$ cells in 30 ml DMEM supplemented with 10% FCS and L-Glutamine (2 mM), in a 15 cm plastic tissue culture dish. Upon re-attachment of the cells to the bottom of the dish, 5 µg each of the transfer vector MigR1, the packaging construct VPack-GP (Stratagene) and the envelope construct wtEnv-I-puro were transfected using 1.5 ml unsupplemented DMEM and 45 µl FuGENE®6 (Roche) according the manufacturers' instructions. Two days post transfection, viral vector particle containing supernatants were harvested into a 50 ml-Falcon tube and subjected to a centrifugation step to obtain cell-free vector particle preparations. Using an Eppendorf centrifuge (model 5810 R), contaminating packaging cells were pelleted at 4° C. and 1,200 rpm for 3 minutes. Cell-free supernatants were used to directly transduce target cells or alternatively, stored at −80° C. for up to two weeks until required.

Figure 2A:
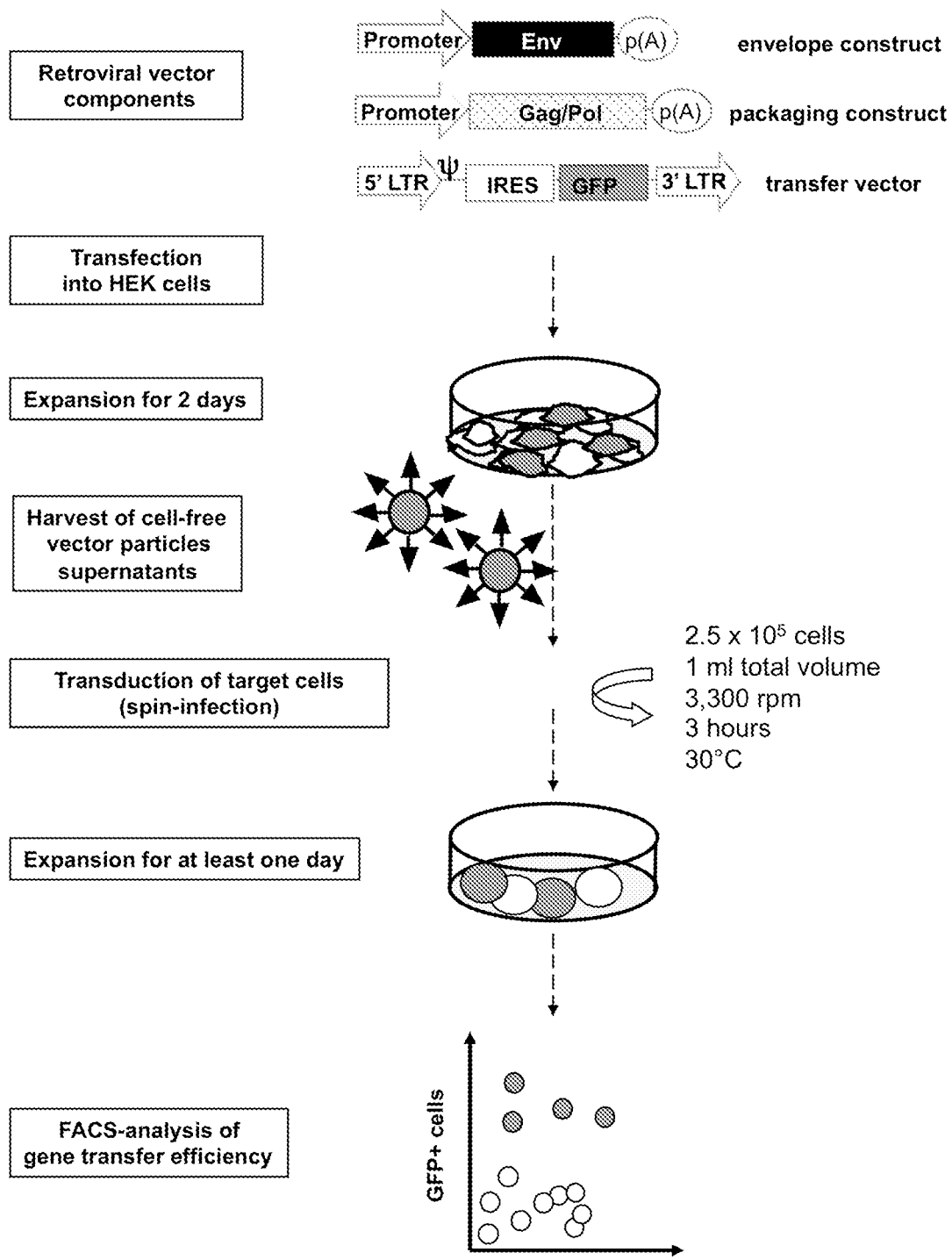
FIG. 2a: Schematic illustration of the standard experimental procedure to test retroviral vector particle-mediated transduction of target cells. The retroviral vector components; envelope construct, packaging construct and transfer vector encoding the reporter gene GFP are transiently transfected into HEK cells. Two days post transfection, cell-free viral vector particle-containing supernatants are harvested and subjected to spin-infection of target cells. Upon continuous culture for at least one additional day, cells are analyzed for the expression of the reporter gene GFP using fluorescence-activated cell sorting (FACS).

Transduction of target cells was performed as follows. Using 2 ml or 1.5 ml cups (Eppendorf), $2.5\times10^5$ target cells were added to each cup in a total volume of 1 ml medium containing the diluted or undiluted vector particles. These samples were centrifuged (Eppendorf, model 5417 R) at 30° C. and 3,300 rpm for 3 hours. Supernatants were discarded and the cell pellets re-suspended in their cultivation media. Two to five days post transduction, target cells were analysed for the expression of the reporter gene GFP using fluorescent activated cell sorting (FACSAria™, BD Biosciences). The generation of retroviral vector particles, transduction and FACS-analysis of gene transfer efficiency is schematically illustrated in FIG. 2a.

Figure 2B:
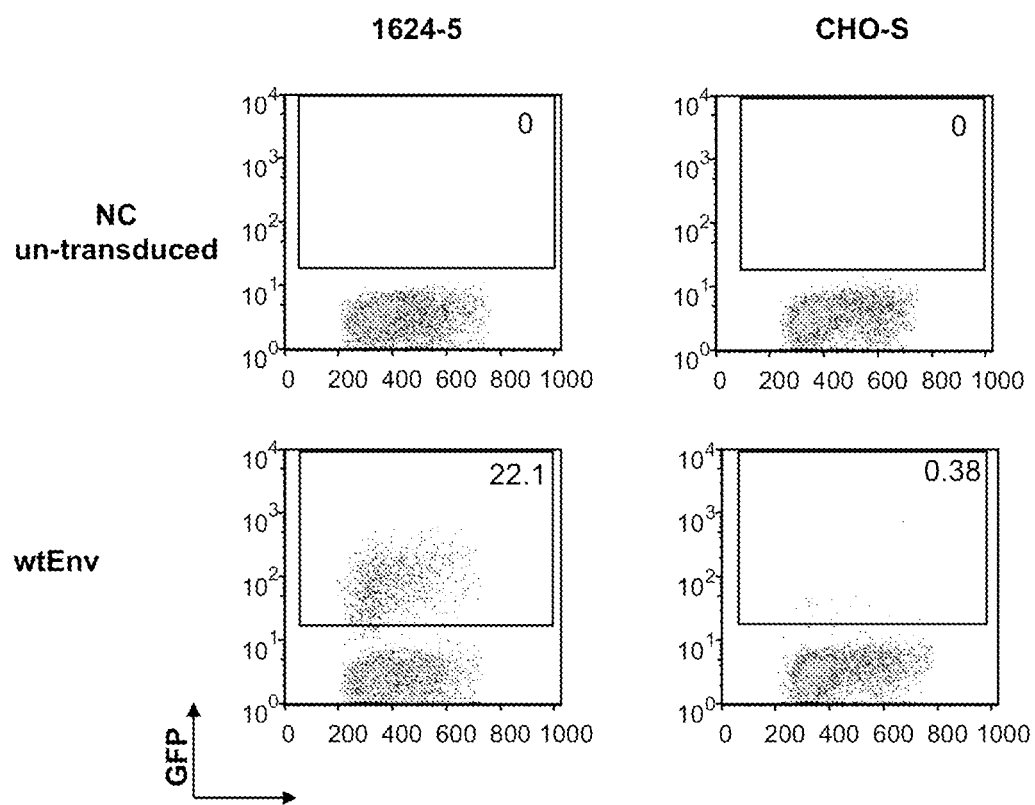
FIG. 2b: FACS-analysis of transduced murine 1624-5 pre-B and Chinese hamster ovary CHO-S cells using MLV-based vector particles displaying the envelope wtEnv of ecotropic MLV (Mo-MLV). Untransduced cells served as negative controls (NC). The expression of the transduced reporter gene GFP is detected.

An example of such a transduction experiment is shown in FIG. 2b. Here frozen vector particle preparations harvested from transfected HEK cells, as described above (MigR1, VPack-GP, wtEnv-I-puro), were thawed after storage at −80° C. and while still undiluted, were used to transduce 1624-5 and CHO-S cells as described above. Two days post transduction, FACS-analysis of target cells was performed. Untransduced target cells served as negative controls. While more than 22% of transduced murine 1624-5 pre B cells revealed expression of the reporter gene GFP, gene transfer efficiency into hamster CHO-S cells was almost undetectable (0.38%). These results show the low susceptibility of CHO cells towards transduction using conventional MLV-based vector particles using the wild type envelope (wtEnv) of ecotropic MLV.

Example 4

Figure 3:
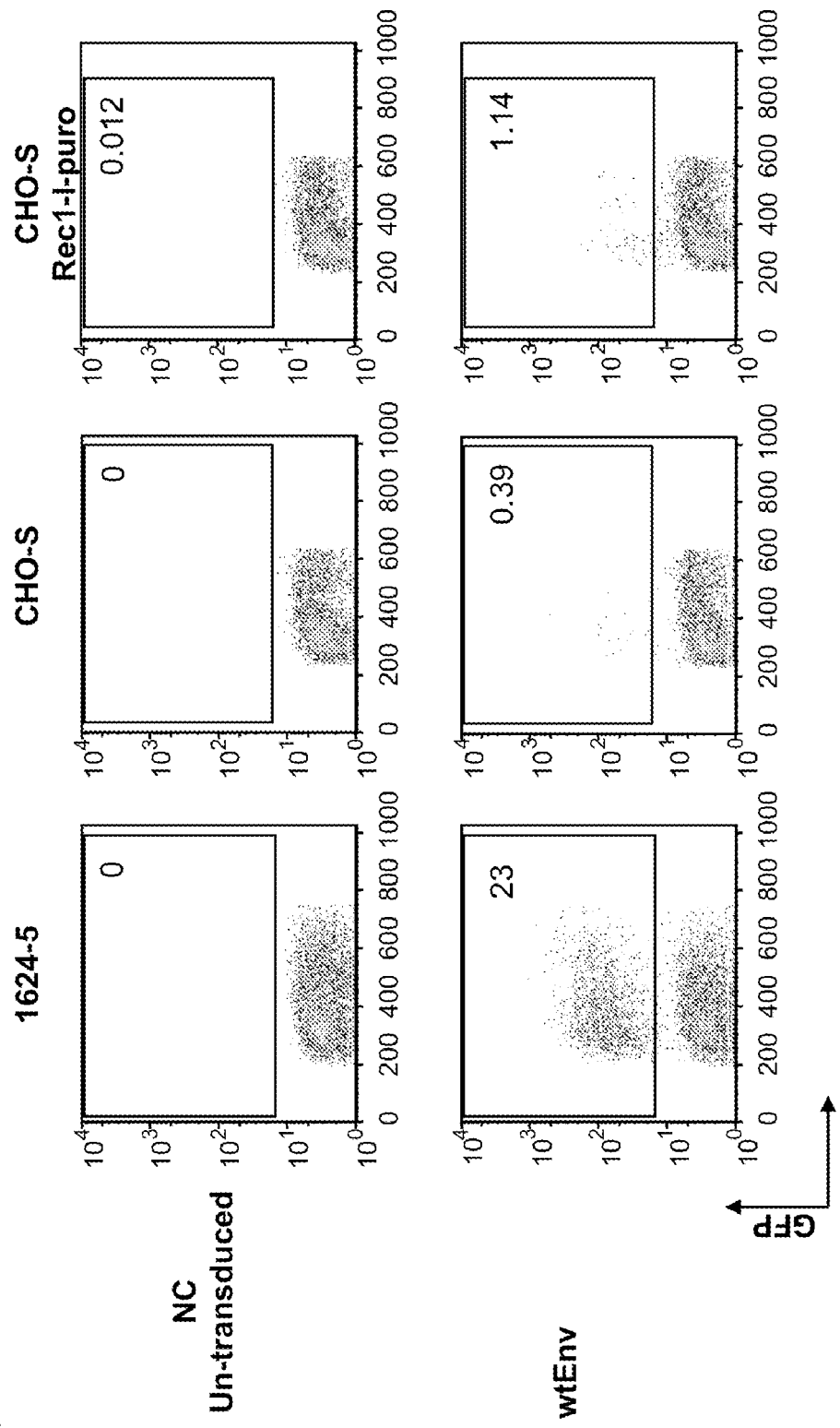

Transduction of Recombinant CHO-S Cells Expressing Rec1 Using wtEnv of Ecotropic MLV To study whether the gene transfer efficiency into CHO-S cells using wild type ecotropic vector particles could be enhanced by recombinant expression of the ecotropic receptor Rec1, the above experiment (Example 3) was repeated but using CHO-S Rec1-I-puro cells in addition to parental CHO-S and 1624-5 cells. As shown in FIG. 3, 1624-5 cells were again transduced with high efficiency (23% GFP positive cells) in contrast to CHO-S cells (0.39% GFP positive cells). Notably, CHO-S Rec1-I-puro cells revealed a 3-fold elevated gene transfer efficiency (1.14% GFP positive cells) when compared to parental CHO-S cells, which demonstrates the conductive effect of Rec1-overexpression on gene transfer efficiency using wtEnv-enveloped MLV-based retroviral vector particles.

Example 5

Transduction of Recombinant CHO-S Cells Expressing Rec1 Using wtEnv of Ecotropic MLV and the Envelope of Molecular Clone PVC-211Mc (PVC-211 Env)

The gene transfer efficiency into CHO-S cells and CHO-S cells recombinantly expressing the receptor Rec1 was compared using wtEnv-enveloped MLV-based retroviral vector particles or retroviral vector particles displaying the envelope of molecular clone PVC-211 of MLV. Vector particles were generated as described in Example 3 with the exception that the transfer vector MigR1 was used and either the envelope construct pwtEnv-I-puro or pPVC-211 Env-I-puro. Cell-free vector particle-containing supernatants were harvested and stored at −80° C. as described above. Thawed, undiluted supernatants were used to transduce 1624-5, CHO-S and CHO-S Rec1-I-puro cells as outlined in Example 3.

Figure 4:
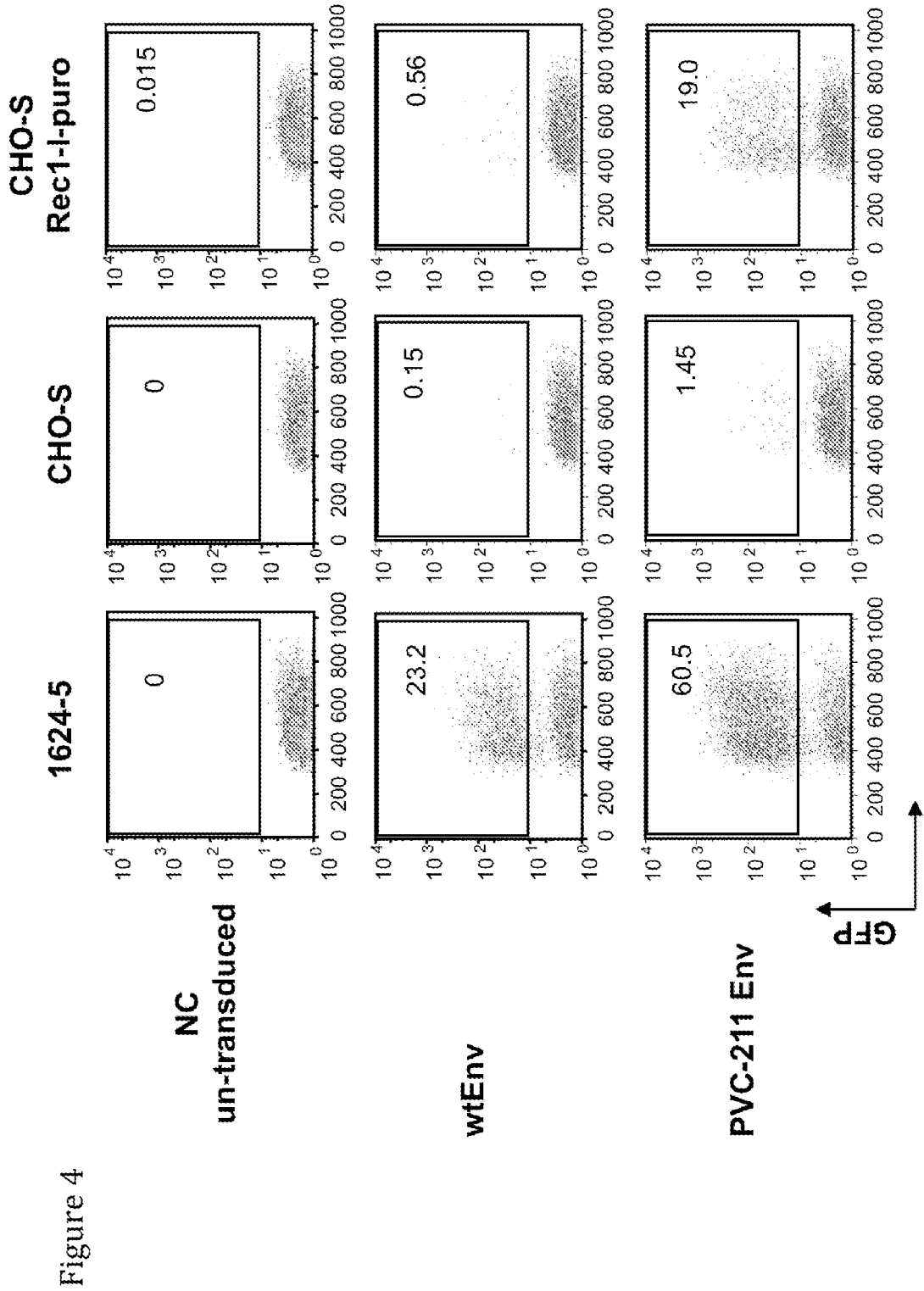
FIG. 4: FACS-analysis of the expression of the reporter gene GFP in transduced murine 1624-5 pre-B cells, CHO-S cells and CHO-S cell transfectants, expressing the recombinant receptor of ecotropic MLV Rec1 (CHO-S Rec1-I-puro). MLV-based vector particles displaying either the envelope wtEnv of ecotropic MLV, or the envelope of the molecular clone PVC-211 were used, as indicated. Untransduced cells served as negative controls (NC).

Three days post transduction FACS-analysis revealed highly efficient transfer of the GFP reporter genes into the murine 1624-5 pre-B cells (as shown in FIG. 4). However, the use of PVC-211 Env-pseudotyped particles resulted in an approximately 3-fold higher gene transfer efficiency (60.5%) when compared to the use of wtEnv-displaying vector particles (23.2%), demonstrating that higher vector titers could be obtained with the use of MLV (PVC-211 Env) vector particles. Enhanced transduction efficiency using PVC-211 Env was also observed when CHO-S cells were used as target cells (1.45%), which exceeded the efficiency of transduction seen with MLV (wtEnv) vector particles (0.15%) by a factor of more than 9-fold.

Even greater transduction efficiency was observed when the target cells CHO-S Rec1-I-puro were transduced. Using MLV (wtEnv) vector particles, gene transfer was improved compared to that observed for CHO-S cells by a factor of 3.7 (0.56%) but was still considerably low. When MLV (PVC-211 Env) vector particles were used for transduction, 19.0% of CHO Rec1-I-puro cells were detected to express GFP. This is a 13-fold improvement compared to the gene transfer efficiency observed for CHO-S target cells and more than a 33-fold increase in transduction efficiency compared to that observed for the transduction of CHO-S Rec1-I-puro cells using MLV (wtEnv) vector particles. The results are summarised in the table below in which transduction efficiency, measured as the percentage of GFP positive cells, is shown for each cell type transduced with different MLV enveloped particles:

| Cell type | Retroviral vector particle | |
|---|---|---|
| | MLV(wtEnv) | MLV(PVC-211Env) |
| 1624-5 cells | 23.2% | 60.5% |
| CHO-S | 0.15% | 1.45% |
| CHO-S Rec1-I-puro | 0.56% | 19.0% |

These findings indicate that the retroviral vector particles MLV (PVC-211 Env) yield higher titers than MLV (wtEnv) particles. In addition, MLV (PVC-211 Env) seems to more efficiently recruit the Rec1 receptor for cell entry as shown by the high transduction efficiencies observed when using CHO-S Rec1-I-puro cells. Strikingly, the comparison of gene transfer efficiencies obtained for MLV (wtEnv) vector particles in CHO-S cells (0.15%) and MLV (PVC-211 Env) vector particles in CHO-S Rec1-I-puro cells (19.0%) reveals a 126-fold increase in transduction efficiency. This is demonstrates the synergistic effect of over-expression of the ecotropic receptor Rec1 in target CHO cells and the utilization of MLV-derived vector particles pseudotyped with the envelope of the molecular clone PVC-211.

Example 6

Transduction of CHO-S Cells with MigR1-Derivatives

To assess whether different promoters for driving reporter gene expression influenced the transduction efficiencies of CHO cells, MLV (wtEnv) and MLV (PVC-211 Env) vector particles were used to transfect derivatives of MigR1 vectors.

HEK cells were seeded at a density of $5\times10^5$ cells in 2 ml medium in a 6-well plastic tissue culture dish (Greiner bio-one). Upon reattachment of the cells to the bottom of the dish 5 hours post seeding, 1 μg each of the packaging construct VPack-GP (Stratagene) the envelope constructs PVC-211 Env-I-puro or VPack-Eco (Stratagene), referred to as 'wtEnv', and the transfer vectors MigR1, MigR1-$P_{Vκ}$, and MigR1-Ppgk respectively, were transfected using 300 μl unsupplemented DMEM and 10 μl FuGENE®6 (Roche) according the manufacturers' instructions. Two days post transfection, cell-free viral vector particle-containing supernatants were harvested and used to transduce CHO-S cells as described above.

Figure 5:
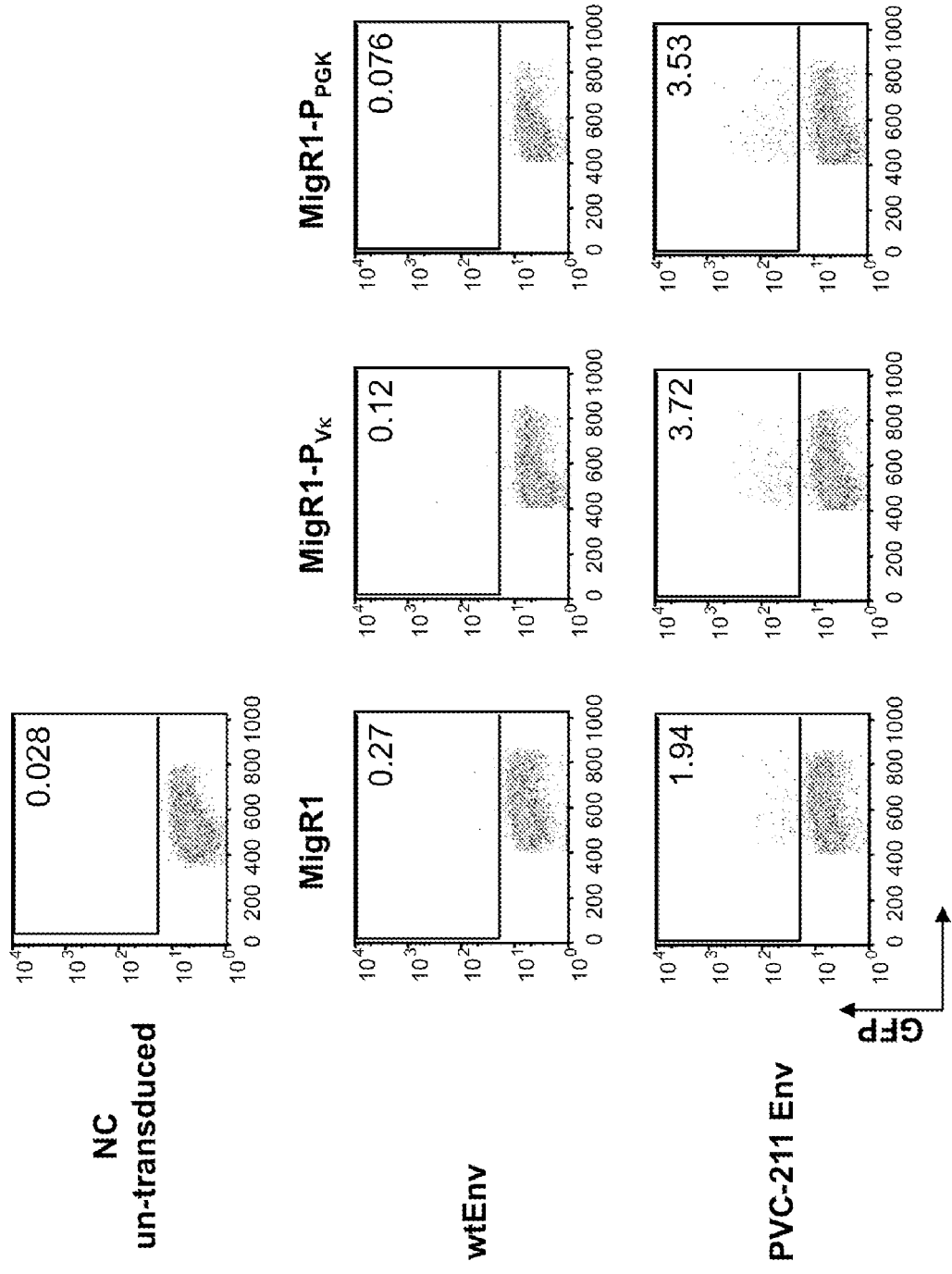
FIG. 5: Comparison of GFP reporter gene expression in transduced CHO-S cells using different MigR1-based retroviral expression vectors. MLV-based vector particles displaying the envelope wtEnv of ecotropic MLV or the envelope of the molecular clone PVC-211 were used. Untransduced cells served as negative controls (NC). The transfer vectors MigR1, MigR1Ppgk and MigR1Pv$_\kappa$ were employed as indicated.

Three days post transduction, transduced cells were analyzed using FACS and the results are as illustrated in FIG. 5. Gene transfer was barely detectable using MLV (wtEnv) vector particles whereas the use of MLV (PVC-211 Env) vector particles resulted in much higher transduction efficiencies, ranging from 1.94% (MigR1) to 3.72% (MigR1-$Pv_κ$). The presence of the promoter for driving reporter GFP gene expression in the transfer vector, had no significant effect on transduction efficiency.

Example 7

Transduction of Human Fibrosarcoma HT1080 Cells in the Presence and Absence of Rec1 Expression To test whether MLV (PVC-211 Env) vector particles when compared to MLV (wtEnv) vector particles would mediate higher gene transfer efficiencies in human cells, these particles were used to transduce HT1080 cells that recombinantly expressed the ecotropic receptor Rec1.

Frozen vector particles, as described in Example 3, were thawed and used to transduce a variety of different target cells: human fibrosarcoma HT1080 cells, HT1080 Rec1-I-neo cells, murine pre-B 1624-5 cells, as well as CHO-S and CHO-S Rec1-I-puro cells according to the methods described in Example 3.

Figure 6:
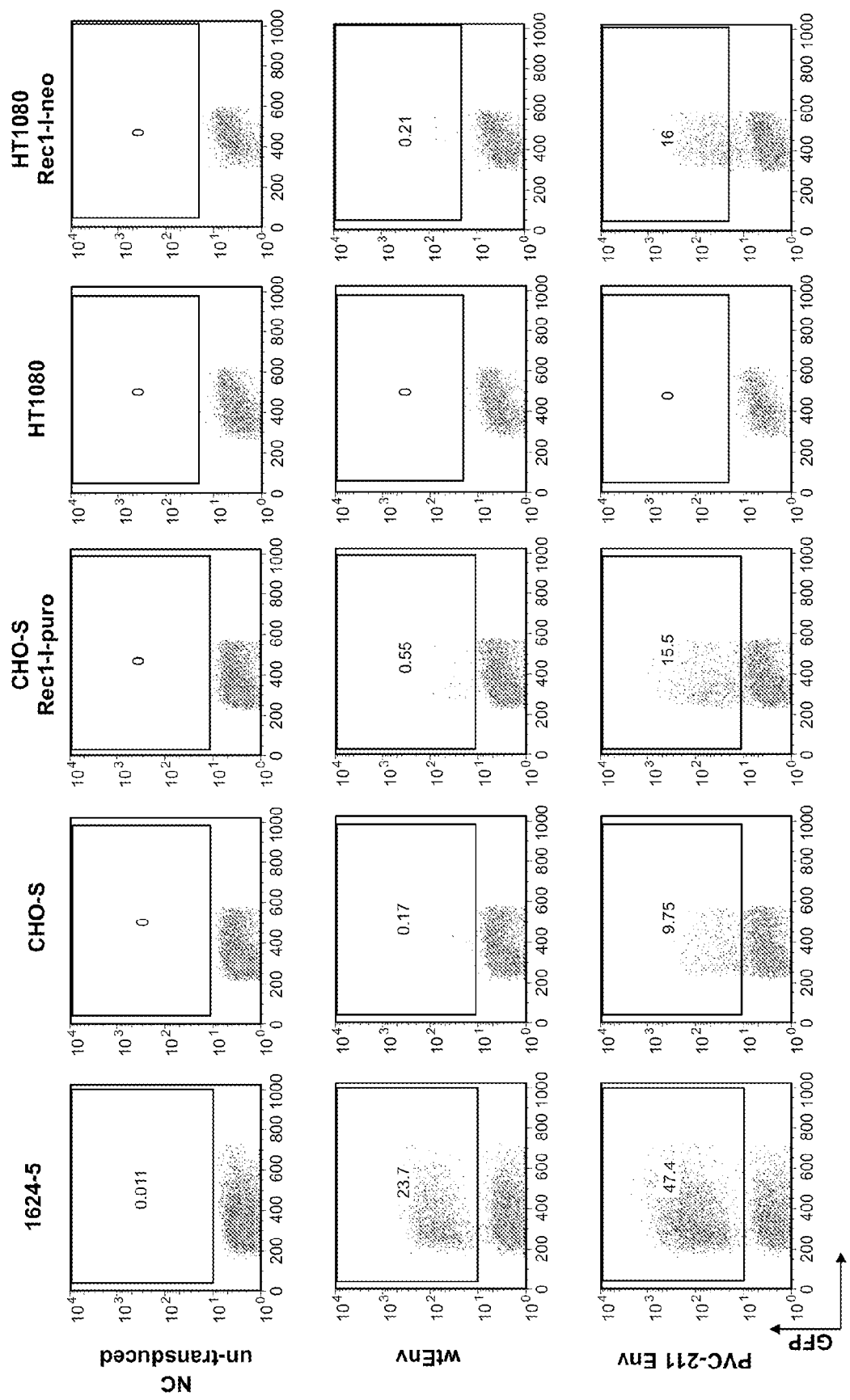
FIG. 6: FACS-analysis of murine preB cell line 1624-5, CHO-S, CHO-S Rec1-I-puro, non-permissive human fibrosarcoma HT1080 and HT1080 Rec1-I-neo cells expressing the recombinant ecotropic receptor of MLV for the expression of the reporter gene GFP. MLV-based vector particles displaying the envelope wtEnv of ecotropic MLV or the envelope of the molecular clone PVC-211 were used as indicated. Untransduced cells served as negative controls (NC).

Three days post transduction, FACS analysis revealed highly efficient gene transfer into 1624-5 cells, see FIG. 6. This was readily detected and independent of the envelope employed (wtEnv, 23.7%; PVC-211 Env, 47.4%). Again, transduction of CHO-S and CHO-S Rec1-I-puro cells using MLV (wtEnv) vector particles was barely detectable (0.17% for CHO-S and 0.55% for CHO-S Rec1-I-puro cells); however, as observed previously, use of MLV (PVC-211 Env) vector particles resulted in much higher transduction efficiencies (9.75% for CHO-S compared to 15.5% for CHO-S Rec1-I-puro cells).

Notably, no transduction was detected of human Rec1-negative HT1080 cells. In contrast, 16.0% of HT1080 Rec1-1-neo cells (Rec1-positive HT1080 cells) showed GFP reporter gene expression following MLV (PVC-211 Env) vector particle-mediated transduction, but only 0.21% of HT1080 Rec1-I-neo cells were GFP-positive when MLV (wtEnv) vector particles were used. These findings clearly indicate that Rec1 is the cognate receptor for PVC-211 Env and wtEnv and therefore that both envelopes mediate the same ecotropic receptor utilization or phenotype tropism. The results are summarised in the table below in which transduction efficiency, measured as the percentage of GFP positive cells, is shown for each cell type transduced with different MLV enveloped vector particles:

| Cell type | Retroviral vector particle | |
|---|---|---|
| | MLV(wtEnv) | MLV(PVC-211Env) |
| 1624-5 cells | 23.7% | 47.4% |
| CHO-S | 0.17% | 9.75% |
| CHO-S Rec1-I-puro | 0.55% | 15.5% |
| HT1080 | undetected | undetected |
| HT1080 Rec1-I-neo | 0.21% | 16.0% |

These data again support the theory that PVC-211 Env recruits the receptor Rec1 for transduction more efficiently than wild type Env and demonstrates the synergistic effect of using retroviral vector particles psuedotyped with PVC-211 envelope to transduce host cells over expressing the Rec1 receptor, as was observed and described previously in Example 5.

Example 8

Transduction of CHO Cell Lines in the Presence or Absence of Recombinant Rec1 Expression The transduction efficiencies of MLV (wtEnv) and MLV (PVC-211 Env) vector particles to transduce other CHO-based cell lines; CHO-S, CHO T-REx™ and CHO-K1, in the presence and absence of recombinant Rec1-expression was tested. As for the generation of ecotropic MLV-based vector particles (Example 3) a triple co-transfection approach employing HEK cells was used.

Figure 7A:
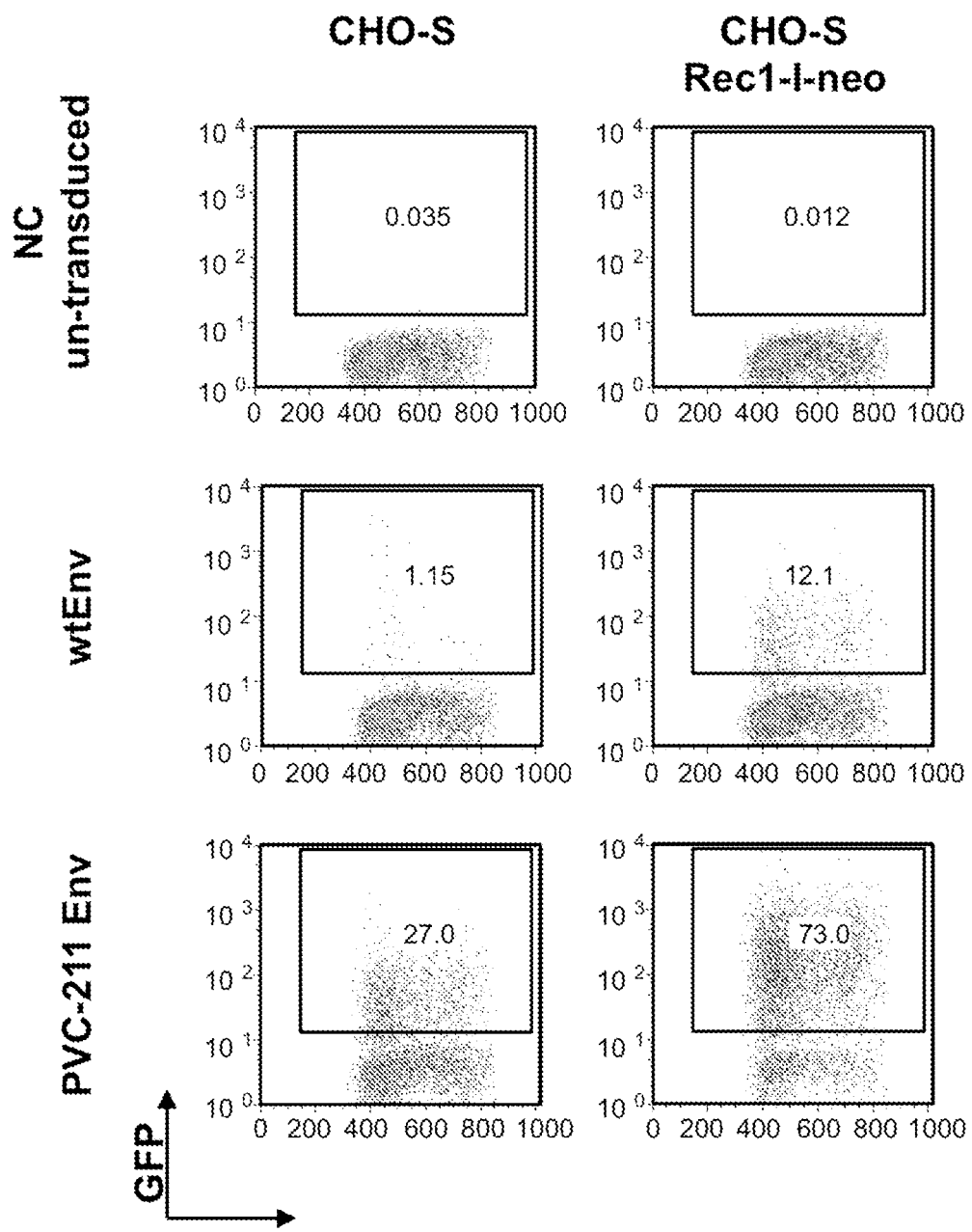
FIG. 7: FACS-analysis of the expression of the reporter gene GFP in different CHO-derived transduced cell lines, (a) CHO-S, (b) CHO-K1, (c) and CHO T-REx™, in the presence or absence of recombinant expression of the ecotropic receptor Rec1 (Rec1-I-neo). MLV-based vector particles displaying either the envelope wtEnv of ecotropic MLV, or the envelope of the molecular clone PVC-211 were used, as indicated. Untransduced cells served as negative controls (NC).
Figure 7B:
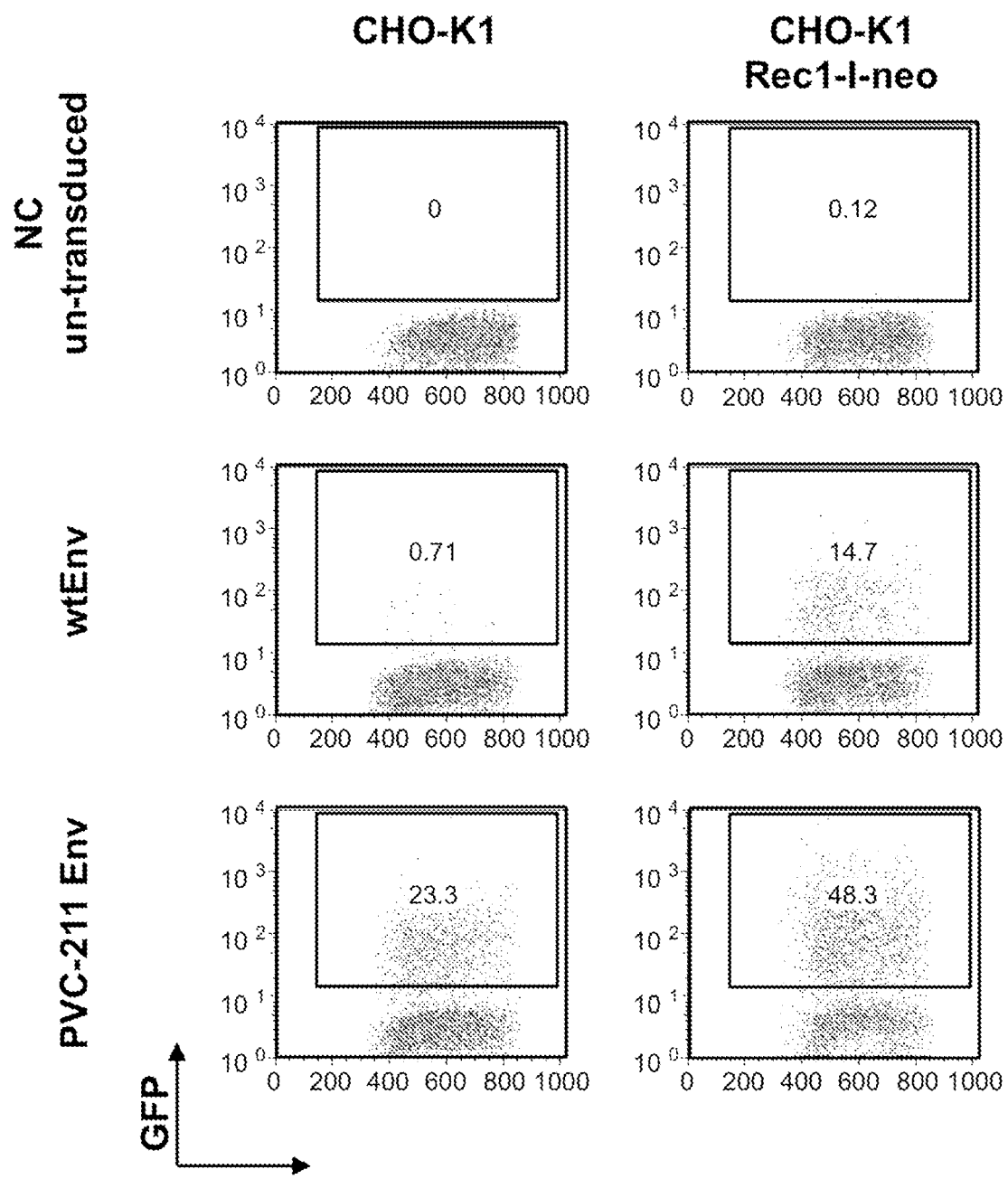
Figure 7C:
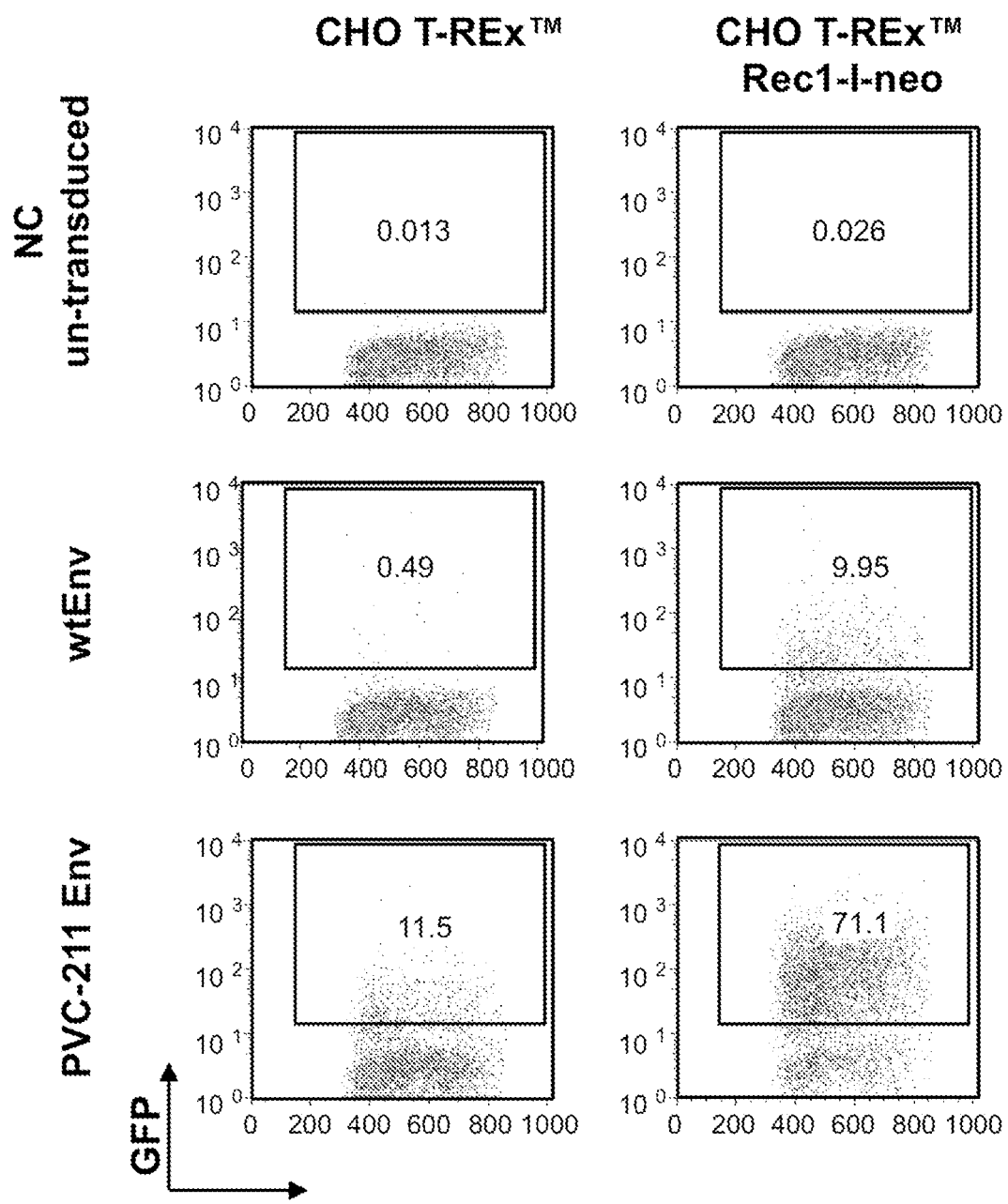

HEK cells were seeded at a density of $3\times10^6$ cells in 30 ml DMEM supplemented with 10% FCS and L-Glutamin (2 mM), in a 15 cm plastic tissue culture dish. Upon re-attachment of the cells to the bottom of the dish 5 hours post seeding, 7 µg of the transfer vector MigR1Ppgk, 4.0 µg of the packaging construct GP-1-bleo and 4.0 µg of the envelope construct wtEnv-I-puro or PVC-211 Env-I-puro were transfected using 1.5 ml DMEM and 45 µl FuGENE6 (Roche) according the manufacturers' instructions. Two days post transfection, cell-free viral vector-containing supernatants were harvested as described in Example 3 and were used to transduce CHO-S (Invitrogen), CHO-K1 (DSMZ) and CHO T-REx™ (Invitrogen) cells, which were either unmodified or ectopically expressing ecotropic receptor Rec1, as described in Example 2. A standard transduction protocol was used as described above and two days post transduction FACS-analysis was performed to detect gene transfer using the reporter gene GFP. As depicted in FIGS. 7a, 7b and 7c the pattern of gene transfer efficiency, as observed previously, was again observed. wtEnv mediated only very low levels of transduction in wild type CHO cells (0.49% to 1.15%) whereas MLV (PVC-211 Env) particles achieved much higher levels of transduction (11.5% to 27%) in the CHO cell lines. Recombinant expression of Rec1 by the CHO cells rendered them more susceptible to wtEnv-mediated transduction (9.95% to 14.7%). Such transduction levels however, were significantly exceeded by the use of PVC-211 Env particles (48.3% to 73.0%). In conclusion, the synergistic effect of enhancing gene transfer efficiency by the use of PVC-211 Env vector particles and Rec1-overexpression in target cells was not only observed in CHO-S cells but also in CHO-K1 and CHO T-REx™ cells. Using these two components in combination, retroviral transduction of CHO T-REx™ cells could be improved up to 145-fold (0.49% transduction with wtEnv and wild type CHO T-REx™ cells compared to 71.1% transduction with PVC-211 Env and CHO T-REx™ Rec1-I-neo cells).

The results are summarised in the table below in which transduction efficiency, measured as the percentage of GFP positive cells, is shown for each CHO cell type transduced with different MLV enveloped vector particles:

| Cell type | Retroviral vector particle | |
|---|---|---|
| | MLV(wtEnv) | MLV(PVC-211Env) |
| CHO-S | 1.15% | 27.0% |
| CHO-S Rec1-I-puro | 12.1% | 73.0% |
| CHO-K1 | 0.71% | 23.3% |
| CHO-K1 Rec1-I-neo | 14.7% | 48.3% |
| CHO T-REx ™ | 0.49% | 11.5% |
| CHO T-REx ™ Rec1-I-neo | 9.95% | 71.1% |

Example 9

Figure 8:
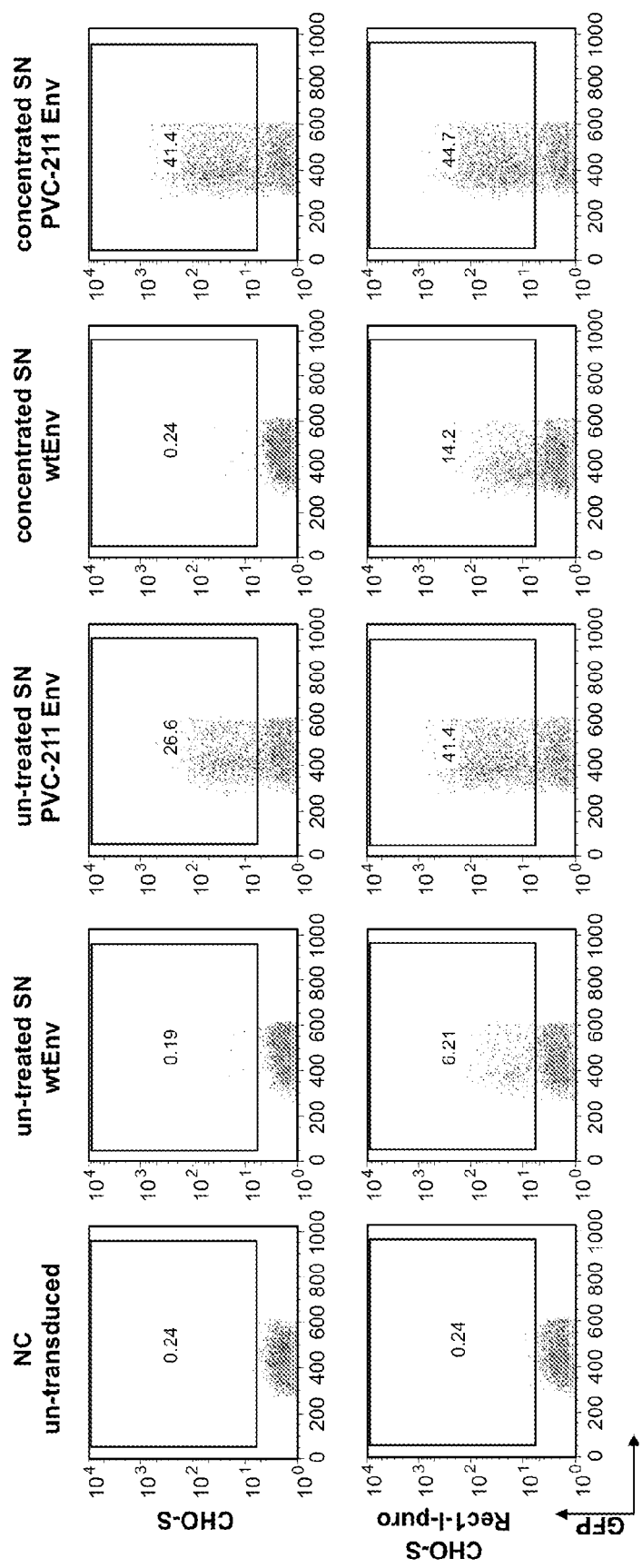
FIG. 8: Comparison of transduction efficiency with untreated or concentrated retroviral vector particle-containing cell culture supernatants, analysed by FACS for the expression of the transduced reporter gene GFP. Particles were concentrated using ultra-filtration. MLV-based vector particles either displaying the envelope wtEnv of ecotropic MLV, or the envelope of the molecular clone PVC-211 were used, as indicated. Untransduced cells served as negative controls (NC).

Concentration of MLV (wtEnv) and MLV (PVC-211 Env) Particles Using Ultra-Filtration and Transduction of CHO-S and CHO-S Rec1-I-puro Cells To further enhance gene transfer efficiencies into CHO cells we next assessed the feasibility of concentrating MLV (wtEnv) and MLV (PVC-211 Env) vector particles prior to transduction. Ecotropic MLV-based vector particles were generated by triple co-transfection employing HEK cells (Example 3) as follows. HEK cells were seeded at a density of $5\times10^6$ cells in 36 ml DMEM supplemented with 10% FCS and L-Glutamine (2 mM), in 15 cm plastic tissue culture dishes. Five hours later and upon reattachment of the cells to the bottom of the dish, 3 µg of the transfer vector MigR1Ppgk, 3.0 µg of the packaging construct VPack-GP (Stratagene) and 3.0 µg the envelope constructs wtEnv-I-puro or PVC-211 Env-I-puro were transfected using FuGENE®6 (Roche) following the manufacturer's instructions. Cell-free supernatants were harvested as described (Example 3) and stored at −80° C. for one month. Thawed supernatants were subjected to concentration by ultra-filtration using Amicon Ultra-15 centrifugal filter devices with a cut-off rate of 30 kDa (Millipore). Supernatant volume was decreased from 30 ml to approximately 1 ml by four 15 minute centrifugation steps at 2,500 rpm and 4° C. (Centrifuge 5810R, Eppendorf). 1 ml of these concentrated and untreated supernatants was used to transduce CHO-S and CHO-S Rec1-I-puro cells using the protocol described in Example 3. FACS-analysis of the transduced cells was performed two days after transduction. As shown in FIG. 8, wtEnv- and PVC-211 Env-mediated transduction of CHO-S and CHO-S Rec1-I-puro cells was enhanced by using concentrated supernatants as opposed to unconcentrated supernatants, but only by a factor of approximately two. The only exception to these results was the transduction of CHO-S Rec1-I-puro target cells using MLV (PVC-211 Env) vector particles. In this instance, no significant elevation of gene transfer using concentrated supernatants was observed (41.4% with unconcentrated supernatants compared to 44.7% with concentrated supernatants). This is likely to be due to the saturation of susceptible target cells with vector particles. MLV-based vectors are only able to transduce cells that are going through the S-phase of the cell cycle wherein cells will be transduced during or briefly after exposure to vector particles. Therefore, it is probable that in this example the maximum susceptible frequency of cells accessible for MLV-derived vector particle-mediated gene transfer is approximately 40% to 50% and no higher efficiencies can be achieved. This notion is further supported by the observation of elevated transduction levels following the use of MLV (PVC-211 Env) vector particles with CHO-S target cells (26.6% with unconcentrated and 41.4% with concentrated supernatants). These findings clearly show that transduction efficiencies into CHO cells can be further improved using concentrated retroviral vector particles employing both envelope variants.

Example 10

Comparison of Transduction Efficiency of MLV wtEnv- and PVC-211 Env-Mediated Gene Transfer into CHO-S and CHO-S Rec1-I-puro Cells Using Similar Multiplicities of Infection The previous examples have demonstrated that MLV (PVC-211 Env) retroviral vector particles mediate gene transfer into CHO-derived and murine pre-B 1624-5 cell lines more efficiently than MLV (wtEnv) vector particles i.e. irrespective of the target cell line. To determine whether this effect was due to the higher vector titers obtained with transient packaging cells employing PVC-211 Env, similar multiplicities of infection (MOI; ratio of infectious particles to target cell count) of MLV (wtEnv) and MLV (PVC-211 Env) particles were utilized in the following experiment.

Figure 9A:
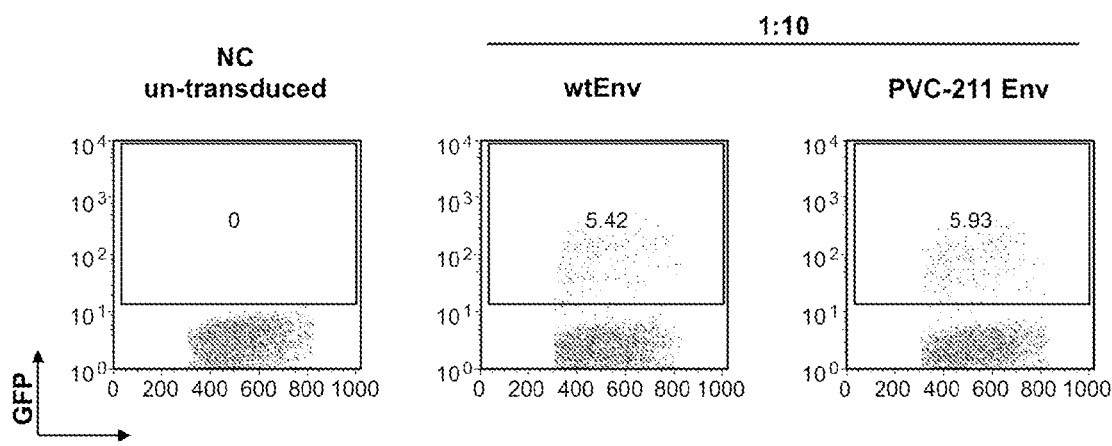
FIG. 9: FACS-analysis for the expression of the transduced reporter gene GFP using titrated vector containing supernatants in (a) 1624-5 cells, (b) CHO-S cells and (c) CHO-S Rec1-I-puro. Cells were exposed to vector preparations with similar multiplicity of infection (MOI) using different dilutions (undiluted, 1/10 and 1/100) and different envelopes. MLV-based vector particles displaying the envelope wtEnv of ecotropic MLV or the envelope of the molecular clone PVC-211 were used. Untransduced cells served as negative controls (NC).
Figure 9B:
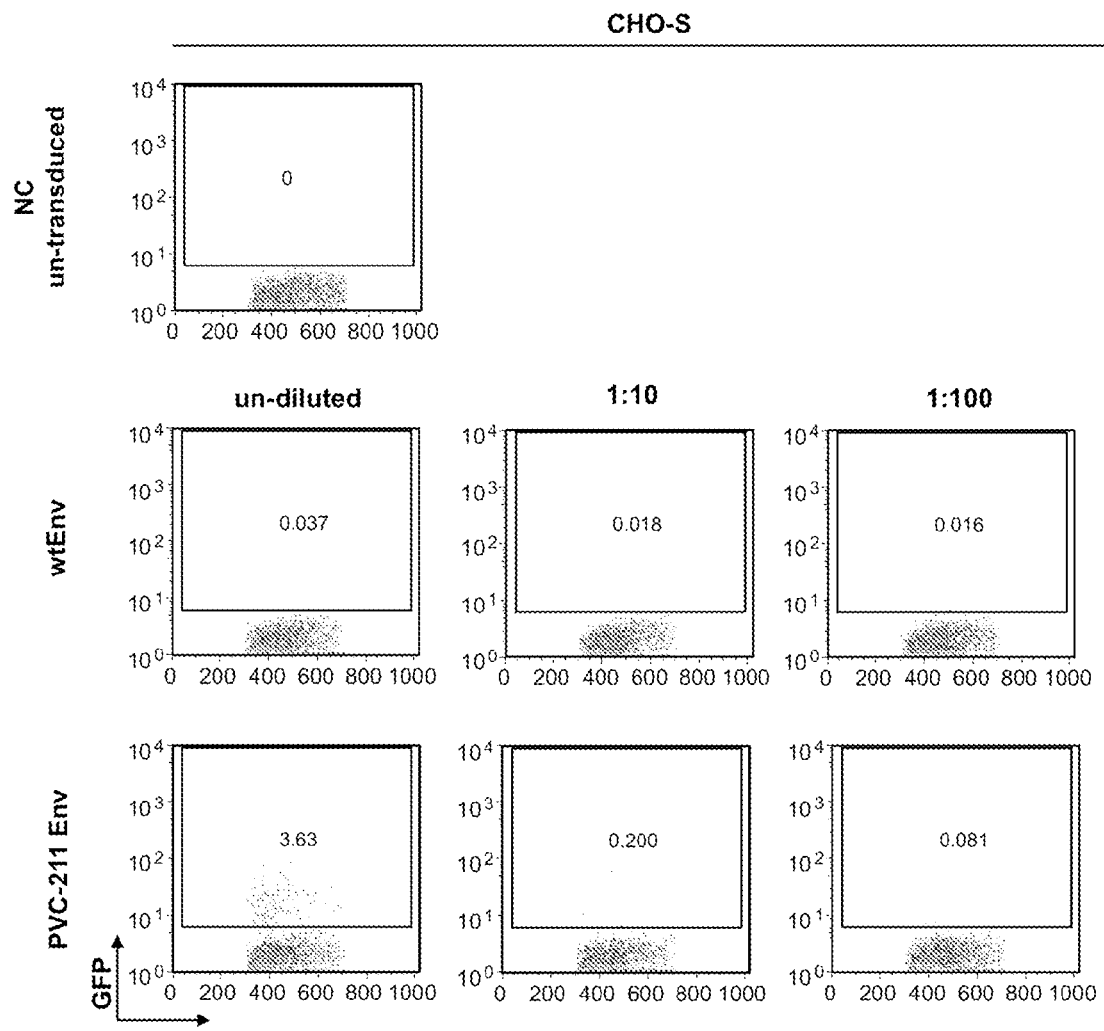

Experimentally, $3 \times 10^6$ HEK cells were seeded in 30 ml DMEM supplemented with 10% FCS and L-Glutamine (2 mM), into 15 cm tissue culture plates. 5 hours post seeding, adherent cells were co-transfected with 3.5 µg VPack-GP (Stratagene), 3.5 µg PVC-211 Env-I-puro or wtEnv-I-puro and 8 µg MigPpgk using 1.5 ml serum-free DMEM and 45 µl FuGENE6 (Roche) following the manufacturer's instructions. Two days post transfection, cell-free supernatants were harvested as described above and stored at −80° C. with one aliquot saved for vector titer titration. The following day these aliquots of supernatants were thawed diluted to $1/10$ and $1/100$ and subjected to the standard transduction procedure using murine pre-B 1624-5 cells. Two days post transduction 1624-5 target cells were analyzed for transfer efficiency by determining GFP-reporter gene expression using FACS. As shown in FIG. 9a, $1/10$ dilutions of both vector particle-containing supernatants yielded similar transduction rates on 1624-5 cells (5.42% using wtEnv and 5.93% employing PVC-211 Env). The parental vector particle preparations were then thawed and used for the transduction of CHO-S and CHO-S Rec1-I-puro cells either undiluted or at dilutions of $1/10$ and $1/100$. Two days post retroviral vector-mediated gene transfer, transduced cells were analyzed for GFP-expression using FACS. As depicted in FIG. 9b, CHO-S cells transduced with undiluted MLV (wtEnv) vector particles (MOI=0.05) showed barely detectable GFP-expression (0.037%). In contrast, CHO-S cells transduced with similar MOI of MLV (PVC-211 Env) showed gene transfer efficiencies of 3.63%, which was more than 5% of the transduction rate achieved using highly susceptible 1624-5 target cells.

Figure 9C:
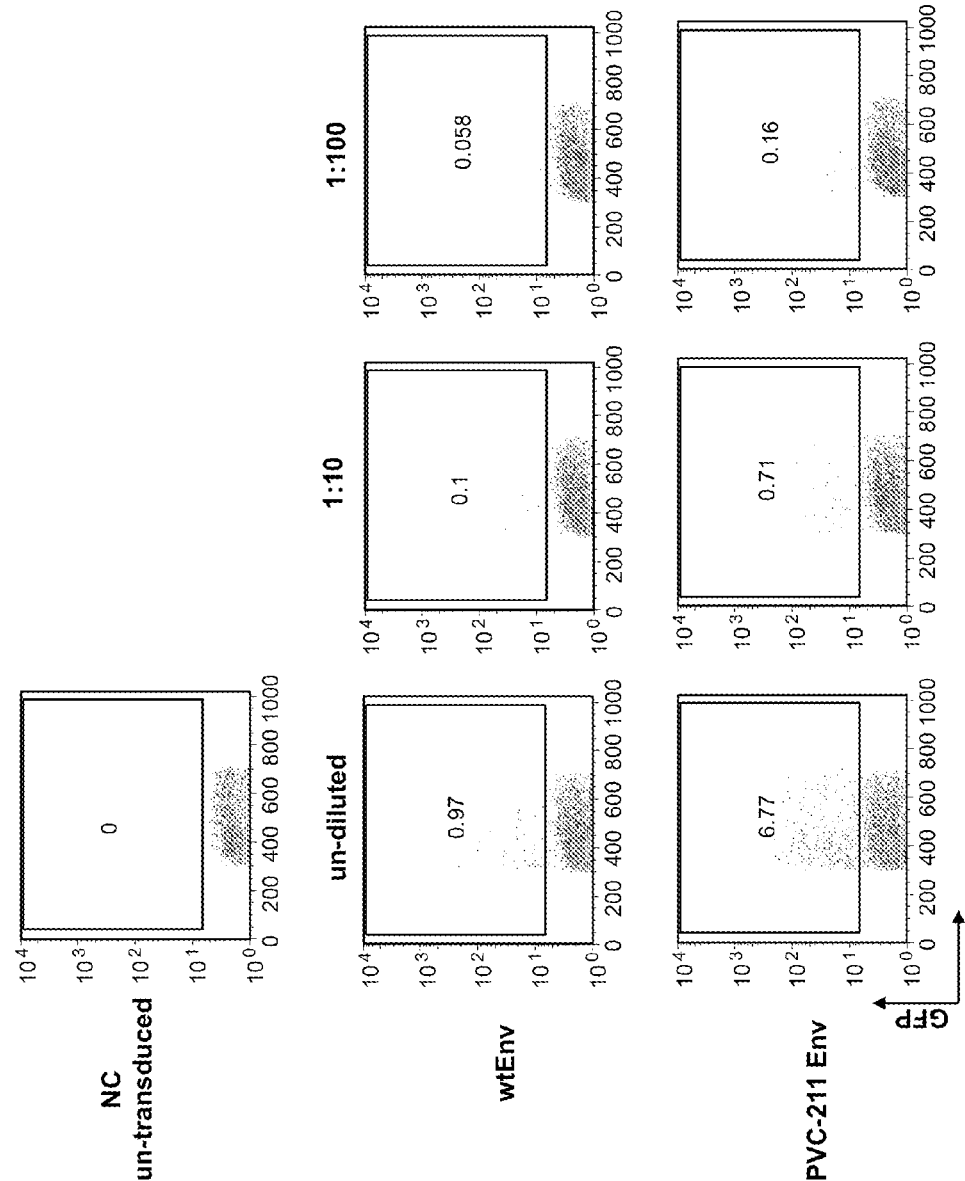

Using CHO-S Rec1-I-puro cells (FIG. 9c) wtEnv-mediated gene transfer reached slightly higher but still very low values (0.97% using undiluted vector preparations). In contrast, MLV (PVC-211 Env) vector particles showed an improved gene transfer efficiency of 2-fold and therefore achieved more than 10% of the transduction rate achieved when using highly permissive 1624-5 target cells.

In conclusion, these observations indicate that MLV (PVC-211 Env) vector particles are much more efficient for the transduction CHO-S cells when compared to MLV (wtEnv) vector particles. This confirms that the higher gene transfer efficiencies demonstrated in the previous examples are not solely attributable to the higher infectious vector titers yielded by the utilization of PVC-211 Env but that this envelope exerts a distinct phenotype mediating CHO-tropism.

Example 11

Figure 10:
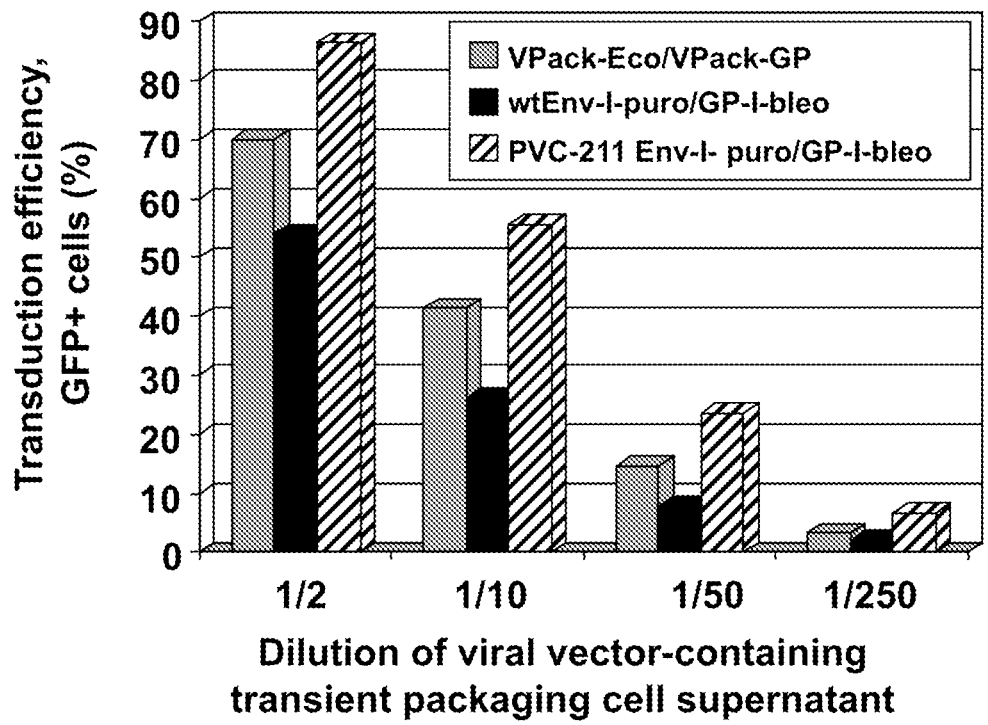
FIG. 10: Transduction efficiencies (% GFP positive cells) using serial dilutions of retroviral vector particle containing cell culture supernatant in 1624-5 target cells using different vector component expression constructs for transient HEK-based packaging cell and vector particle generation as indicated. MigR1Ppgk served as a transfer vector in all three cases.

Comparison of Vector Titers Yielded with Components MigR1Ppgk, GP-1-bleo and wtEnv-I-puro and PVC-211 Env-I-puro The efficiency of transient vector particle generation using the vector system components described below was determined as follows. $5 \times 10^5$ HEK cells were seeded in 2 ml of DMEM supplemented with 10% FCS and L-Glutamine (2 mM), in a six-well tissue culture dish. Five hours later and upon re-attachment of the cells to the bottom of the dish, cells in one well were transfected with 1 µg of the transfer vector MigR1Ppgk, 1 µg of the packaging construct VPack-GP (Stratagene) and 1 µg the envelope construct VPack-Eco (Stratagene). Cells in two other wells were transfected with 1 µg of the transfer vector MigR1Ppgk, 1 µg of the packaging construct GP-1-bleo and 1 µg of the envelope construct wtEnv-I-puro or PVC-211 Env-I-puro. All transfections were performed using FuGENE®6 (Roche) following the manufacturer's instructions. Cell-free supernatants were harvested as described (Example 3) and were used for the transduction of 1624-5 cells using dilutions of the vector particle-containing supernatants of ½, $1/10$, $1/50$ and $1/250$ as described above (Example 10). FACS-analysis for expression of the GFP reporter gene was performed 3 days post transduction. As shown in FIG. 10, all three vector systems facilitated highly efficient gene transfer. The vector titre was calculated as follows: For example, utilization of the $1/250$-diluted supernatant from transient packaging cells using PVC-211 Env-I-puro and GP-1-bleo transduced 6.7% of the $2.5 \times 10^5$ target cells. 6.7% (transduced cells)×250 (dilution)×2,500 (1% of initial target cell count)=$4,1875 \times 10^6$ i.u./ml (infectious vector particle units per ml). Using this equation, wtEnv-I-puro/GP-1-bleo (1.9% of cells transduced at $1/250$ dilution) yielded a vector titre of $1,1875 \times 10^6$ i.u./ml, while use of VPack-Eco/VPack-GP (3.3% of cells transduced at $1/250$ dilution) yielded a titre of $2,0625 \times 10^6$ i.u./ml. These findings therefore indicate the similarity of the described vector components in achieving comparable vector titres upon triple co-transfection of HEK cells. It is useful to note that the utilization of the novel PVC-211 Env-I-puro expression construct together with the packaging construct GP-1-bleo exceeded the vector titers obtained with the commercially available VPack-system.

Example 12

Establishment of Stable HEK-Derived Packaging Cell Lines Using the Constructs GP-I-puro and PVC-211 Env-I-bsr To test whether the disclosed vector components could establish efficient stable packaging cell lines, the following experiment was performed. $5 \times 10^5$ HEK cells were seeded in 2 ml of DMEM supplemented with 10% FCS and L-Glutamine (2 mM) (culture medium), in one well of a six-well tissue culture dish. Five hours later, the cells were transfected with 1 µg of the packaging construct GP-I-puro. The transfection was performed using FuGENE®6 (Roche) following the manufacturer's instructions. Two days post transfection, transfected cells were expanded in culture medium supplemented with puromycin at a concentration of 1 μg/ml. After nine days of selection, surviving cells were expanded in parallel in the presence of 5, 10, 20, 30, 40 and 50 μg/ml puromycin. After further selection for two weeks 5×10⁵ of the surviving cells were expanded in the presence of the highest puromycin concentrations (40 and 50 μg/ml). The cells were then seeded in six-well tissue culture dishes and transfected with 1 μg of the envelope construct PVC-211 Env-1-bsr containing the blasticidin resistance gene using FuGENE®6 (Roche) as described above. Two days post transfection, double-resistance selection with puromycin and blasticidin was initiated. Cells were expanded in the presence of 50 μg/ml puromycin and 30 μg/ml blasticidin or with 40 μg/ml puromycin and 20 μg/ml blasticidin. The resultant packaging cell lines obtained after two weeks of selection were termed PVC-VPC 50/30 and PVC-VPC 40/20 indicating the concentration of puromycin and blasticidin respectively, that was used for their selection.

Figure 11:
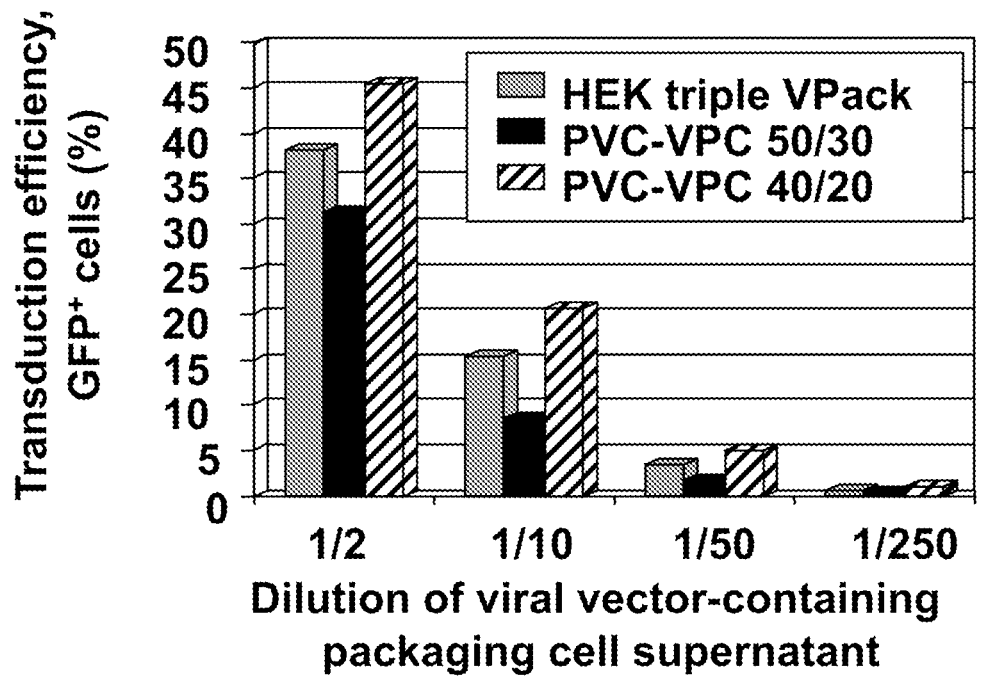
FIG. 11: Transduction efficiencies (% GFP positive cells) using serial dilutions of retroviral vector particle containing cell culture supernatant in 1624-5 target cells using VPack-vector component system (grey) for transient HEK-based packaging cell and vector particle generation or the stable packaging cell lines PVC-VPC 50/30 (black) and PVC-VPC 40/20 (dashed) as indicated. MigR1 served as a transfer vector in all three cases.

To study the capacity of the novel packaging cells for high vector titre production, the cells were seeded at a density of 5×10⁵ in 2 ml of culture medium in the absence of puromycin and blasticidin in a six-well tissue culture dish. In parallel, HEK cells were seeded under identical conditions. Five hours post seeding, packaging cells were transfected with 2 μg of the transfer vector MigR1 and 2 μg of the prokaryotic expression vector pUC18. The HEK cells were also transfected with 2 μg of the transfer vector MigR1 and also with 1 μg of the packaging vector VPack-GP (Stratagene) and the envelope construct VPack-Eco (Stratagene) used previously in Example 11 as a positive control. Two days post transfection cell-free vector particle-containing supernatants were harvested as described in Example 3 and were used for the transduction of 1624-5 cells as outlined in Example 11, using dilutions of ½, ⅒, ⅕₀ and ⅟₂₅₀. The following day, FACS-analysis of transduced cells was performed to detect gene transfer efficiency. As shown in FIG. 11 all transient and stable packaging cell lines yielded high vector titres facilitating gene transfer into murine pre-B 1624-5 target cells at comparable efficiencies. Using the equation described in Example 11, the following vector titres were calculated from transduction efficiencies obtained with the ⅕₀ dilution of vector particle-containing supernatants:
4.25×10⁵ i.u./ml using triple-co-transfection of HEK cells using the VPack-system (3.4% GFP-positive cells),
2.125×10⁵ i.u./ml using the stable packaging cell line PVC-VPC 50/30 (1.7% GFP-positive cells), and
6.25×10⁵ i.u./ml using the stable packaging cell line PVC-VPC 40/20 (5% GFP-positive cells).

In conclusion, all three approaches resulted in comparable vector titres. Notably, PVC-VPC 40/20 yielded the highest vector titres and exceeded the gene transfer efficiency obtained using transient transfection of HEK cells with the commercially available VPack-vector system.

Example 13

Figure 12:
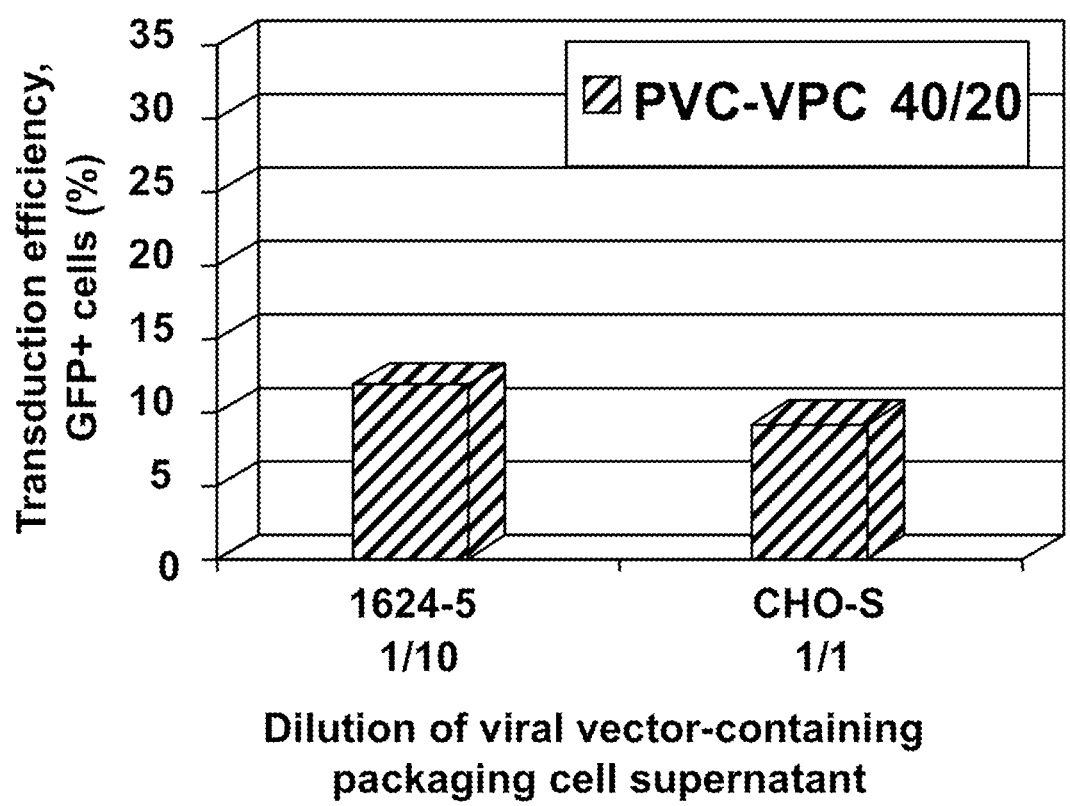
FIG. 12: Transduction efficiencies (% GFP positive cells) using different dilutions of retroviral vector particle containing cell culture supernatant in 1624-5 and CHO-S target cells from the stable packaging cell line PVC-VPC 40/20 as indicated. Vector particle-containing supernatants were employed for transduction either undiluted (1/1) or diluted 1/10 as indicated. MigR1Zeo served as a transfer vector.

Stable HEK-Derived Packaging Cell Line
(PVC-VPC 40/20) Efficiently Transduces CHO-S
Cells To investigate the productivity of the stable packaging cell line PVC-VPC 40/20 (described in Example 12) for the productivity of high-titer vector particles capable of transducing CHO-S cells, the following study was performed. The cell line was seeded in a small tissue culture flask (T25) at a density of 5×10⁵ cells. Five hours post seeding, cells were transfected with 2 μg of the transfer vector pMigR1Zeo using FuGENE®6 (Roche) according to the manufactures' instructions. MigR1Zeo is derived from MigR1 (SEQ ID No: 43) but harbours an additional Zeocin™-resistance gene immediately 5' of the IRES which is flanked on the 3'-side by the reporter gene GFP. Two days post transfection, cell-free vector particle-containing supernatants were harvested as described above and used to transduce 1624-5 murine pre-B and hamster CHO-S cells as described in Example 3. For the transduction of 1624-5 cells a ⅒ dilution of the packaging cell supernatants was used. CHO-S cells were transduced using undiluted (1/1) supernatants. Two days post transduction, GFP-gene transfer efficiency into target cells was analysed using FACS. As depicted in FIG. 12, the stable packaging cell line yielded high vector titers. 11.8% (PVC-VPC 40/20) of transduced 1624-5 cells were readily detected to express the reporter gene GFP. In addition, 9.2% of the CHO-S cells which were transduced with vector particles produced by the novel stable packaging cell line PVC-VPC 40/20 were shown to express GFP.

Example 14

Transduction of BHK Cells

Figure 13:
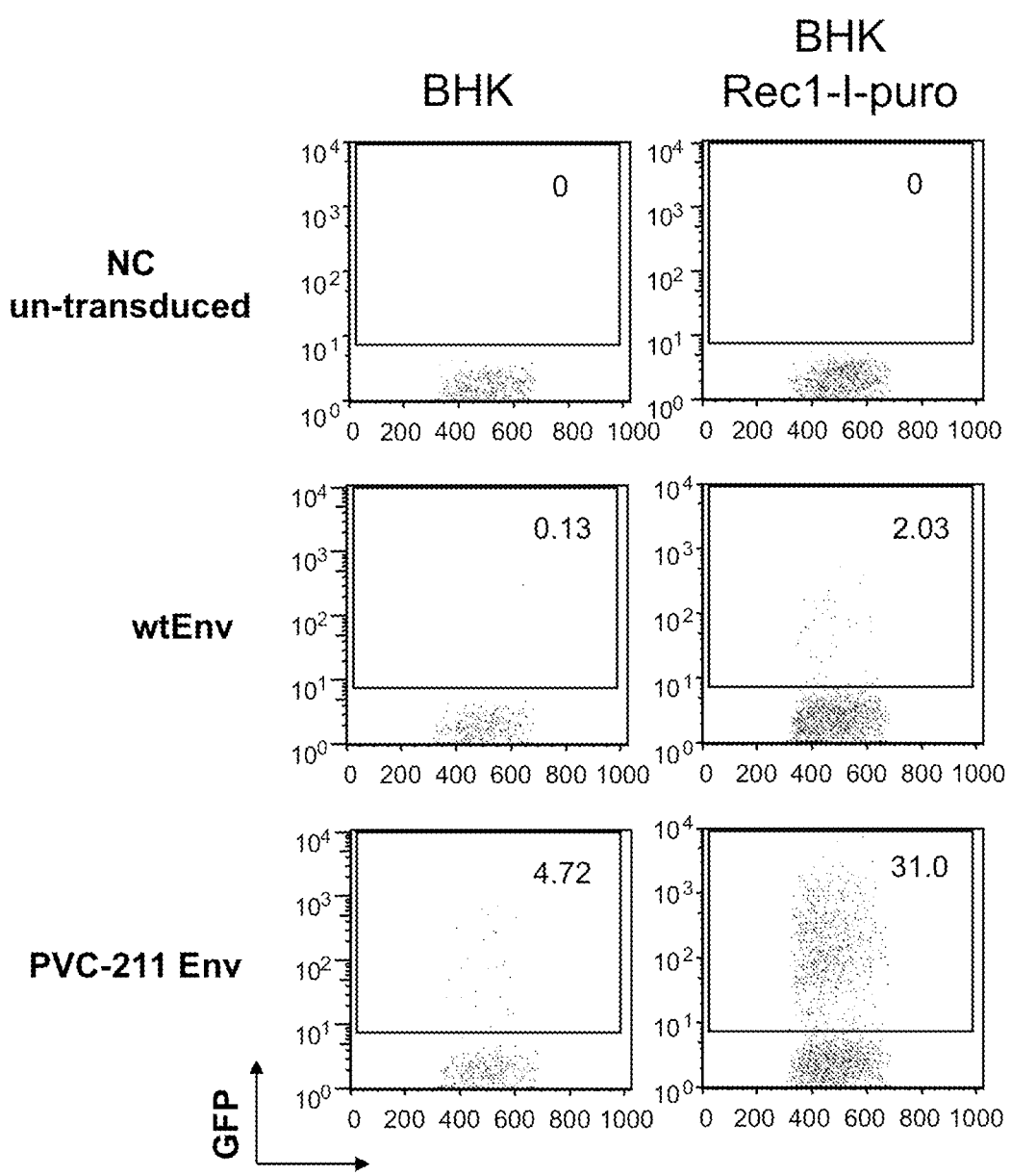
FIG. 13: Comparison of transduction efficiencies of MLV-based vector particles either displaying the envelope wtEnv of ecotropic MLV or the envelope of the molecular clone PVC-211 on BHK cells and BHK cells expressing the recombinant receptor of ecotropic MLV Rec1 (BHK Rec1-I-puro), as indicated. Transduction efficiencies were analyzed by FACS for the GFP reporter gene. Untransduced cells served as negative controls (NC).

To study whether the PVC-211 Env could also enhance transduction efficiency into a target cell line other than CHO cells, the transduction of baby hamster kidney (BHK) cells was investigated. 2 ml of HEK cells were seeded at a density of 5×10⁵ into the wells of a six-well dish and transfected 5 hours later using FuGENE®6 (Roche), according to the manufacturer's instruction, with 1 μg pGP-I-puro, 1 μg pMigR1Ppgk and the envelope constructs wtEnv-I-puro or PVC-211 Env-I-puro, as described in Example 3. Two days post transfection, cell-free supernatants were harvested and stored at −80° C. Two days later, retroviral vector-containing supernatants were thawed and subsequently used to transduce naïve BHK cells and BHK cells expressing the construct Rec1-I-puro as described above. 1 ml of undiluted supernatants were used per transduction. Three days post transduction FACS-analysis of transduced cells and un-transduced cells serving as negative controls revealed barely detectable GFP reporter gene transfer into BHK cells using wtEnv-displaying particles (0.13% GFP positive cells) as shown in FIG. 13. In contrast, particles utilizing PVC-211 Env yielded 2.03% GFP positive cells. BHK cells expressing the receptor Rec1 were more susceptible to transduction and were shown to be transduced with an efficiency of 4.72% using wtEnv and 31.0% employing the PVC-211 envelope. The results are summarised in the table below in which transduction efficiency, measured as the percentage of GFP positive cells, is shown for each BHK cell type transduced with different MLV enveloped vector particles:

| Cell type | Retroviral vector particle | |
|---|---|---|
| | MLV(wtEnv) | MLV(PVC-211Env) |
| BHK | 0.13% | 2.03% |
| BHK Rec1-I-puro | 4.72% | 31.00% |

In summary, and as previously observed with CHO-derived target cells, BHK cells were more efficiently transduced using the retroviral vector particles utilising the envelope of PVC-211 compared to utilisation of wild-type envelope (wtEnv). Upon recombinant expression of the receptor Rec1, gene transfer efficiencies were further improved, as previously observed with CHO-derived target cells.

This example clearly demonstrates that the increase in transduction efficiency observed when using retroviral vector particles enveloped with PVC-211 is not dependent on the target cell type. Furthermore, an increase in transduction efficiency observed when using target cells expressing the Rec1 receptor is not restricted to CHO cells, but is also observed with another target cell type that express the Rec1 receptor.

Example 15

Generation of CHO-S and CHO-S Rec1-I-neo-Based Cell Lines for the Production of his Tagged $VEGF_{121}$ Utilizing Transduction of MLV Vector Particles Using the Envelope of PVC-211

Figure 1J:
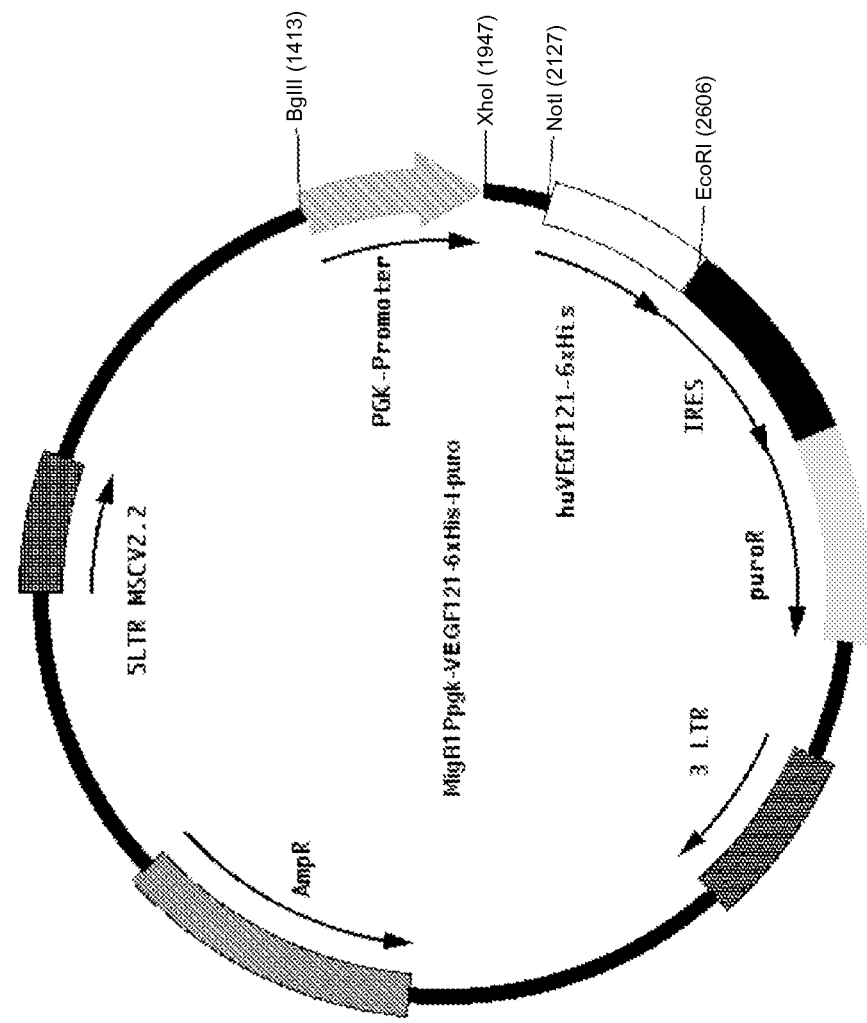
FIG. 1j: The construct MigR1Ppgk-VEGF$_{121}$-6×HIS-I-puro contains the murine Ppgk promoter flanked by the restriction sites for BglII and XhoI. This promoter drives the expression of the human variant of VEGF$_{121}$, flanked by the restriction sites NotI and EcoRI, which harbours a His-tag consisting of six histidine residues at the C-terminus, and the puromycin resistance gene. An IRES located between both genes couples their expression from the same mRNA transcript. This transcript is flanked by 5' and 3' LTRs.
Figure 14A:
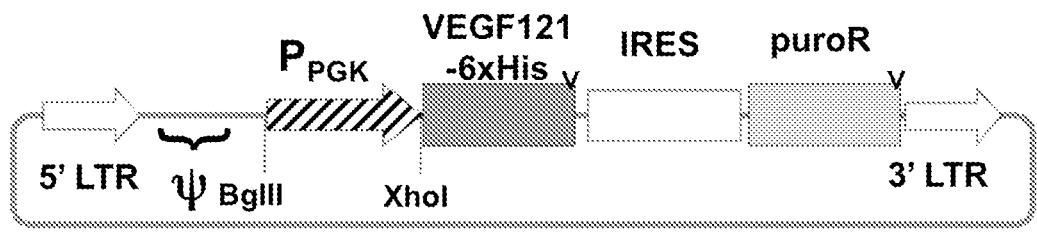
FIG. 14: Utilization of MLV vector particles displaying the PVC-211 envelope for the generation of highly efficient protein producer cell lines. (a) Schematic illustration of the retroviral transfer vector pMigR1Ppgk-VEGF$_{121}$-6×His-I-puro. The promoter of the murine Ppgk (dashed arrow, flanked by restriction sites of BglII and XhoI) drives the expression of the human variant of VEGF$_{121}$, which harbours a His-tag consisting of six histidine residues at the C-terminus (VEGF$_{121}$-6×His; dark grey box) and the puromycin-resistance gene (puroR; light grey box). An IRES (white box) located between both genes couples their expression from the same mRNA transcript. This transcript is flanked by LTRs (white arrows) at the 5'- and 3'-ends. The packaging signal (psi/0 facilitates the packaging of the mRNA into MLV-based particles. (b) Western Blot-analysis of supernatants of puromycin-resistant VEGF$_{121}$-6×His producer cell lines. The apparent molecular weight of 19.4 kD and the signal of detected VEGF$^{121}$-6×His proteins (arrow) are indicated.

To compare the efficiency of generating CHO-based protein producer cell lines, we constructed the retroviral transfer vector pMigR1Ppgk-$VEGF_{121}$-6×His-I-puro as described in Example 1 and illustrated schematically in FIGS. 1*j* and 14*a*.

CHO-S and CHO-S Rec1-I-neo cells were seeded in a six-well dish at a density of $2.5 \times 10^5$ cells per well. Five hours later, the cells were transfected with 1 µg of the plasmid DNA of pMigR1Ppgk-$VEGF_{121}$-6×His-I-puro using FuGENE6® according to the manufacturer's instructions. In parallel, CHO-S and CHO-S Rec1-I-neo cells were transduced with vector particles generated by triple co-transfection of HEK cells with the plasmids pMigR1Ppgk-$VEGF_{121}$-6×His-I-puro, GP-I-puro, and PVC-211-Env-I-puro as described in Example 2. This transduction was performed once or once daily on three consecutive days. All cell populations were expanded in six-well dishes. Five days post transfection, following the one-time transduction and two days following the last repeated transduction, the confluent cell populations were resuspended and seeded into 10 cm dishes using 10 ml cultivation medium. Untreated naïve CHO-S and CHO-S Rec1-I-neo cells serving as negative controls were seeded in parallel. Upon attachment of these cell populations five hours later, 10 µg/ml puromycin (Invitrogen) was added. Four days after initiation of the selection, naïve cells were no longer attached, indicating cell death of the entire negative control (NC) population. In contrast, transfected and transduced cell populations showed puromycin-resistant cell clones visible as colonies using light microscopy. Using a magnification of 50-fold, resistant cell colonies on all other populations were counted in ten randomly selected fields. The results are shown in the table below:

| Cell type | NC Naïve | Transfected | 1x Transduced | 3x Tranduced |
|---|---|---|---|---|
| CHO-S | 0 | 12 | 4 | 12 |
| CHO-S Rec-1-neo | 0 | 11 | 41 | 230 |

As expected, both parental cell lines CHO-S and CHO-S Rec1-I-neo revealed similar numbers of cell colonies, namely 12 and 11, respectively upon transfection. In contrast and upon single transduction, only four colonies were observed for CHO-S cells but 10-fold more (41 colonies) for CHO-S Rec1-I-neo cells. This difference was even greater after three transductions, where 12 colonies were observed for CHO-S and almost 20-fold more (230 colonies) were observed for CHO-S Rec1-I-neo cells. Therefore, and as observed previously when using transfer vectors to transduce the reporter gene gfp, CHO-S Rec1-I-neo cells were demonstrated to be more susceptible to MLV vector particle-mediated gene transfer using the envelope of molecular clone PVC-211.

Figure 14B:
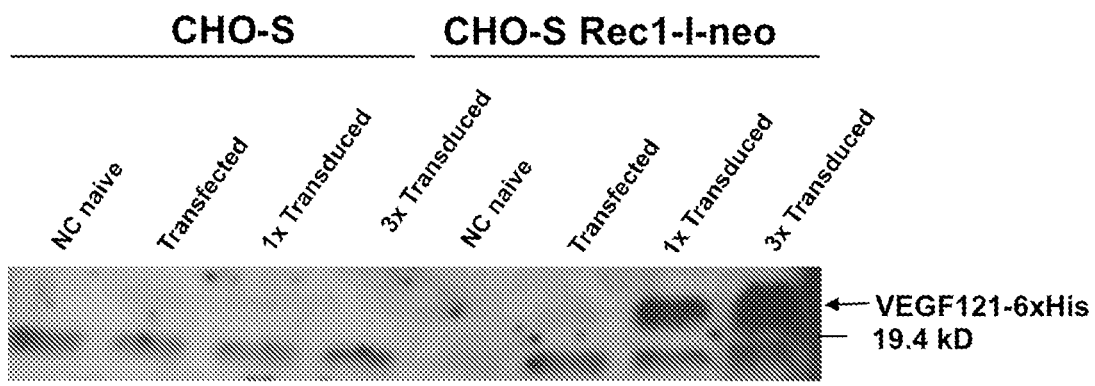

The puromycin-resistant cells of all populations were seeded separately into six-well dishes in 3 ml of culture medium supplemented with 10 µg/ml puromycin per well at a density of $1 \times 10^5$. Naïve CHO-S and CHO-S Rec1-I-neo cells were seeded in parallel in the absence of puromycin and served as negative controls. Four days later, cell-free supernatants were harvested into 15 ml falcon tubes and stored overnight at −80° C. The next day, supernatants were thawed and sample 15 µl of NiNTA Superflow (Qiagen) were added per sample of 2.5 ml supernatant. All samples were kept at 4° C. on a test-tube-rotator to enable the binding of the NiNTA-beads to the His-tag of the $VEGF_{121}$ variant protein secreted by puromycin-resistant producer cell populations. Upon pelleting using a bench-top eppifuge and two washing steps according to the manufacturer's instructions, the beads were resuspended in 70 µl of standard Western Blot loading buffer and heated for 15 min at 95° C. Subsequently, 50 µl of each sample and a molecular weight marker (BenchMark™ Prestained Protein Ladder; Invitrogen) were loaded on a 15% poly-acryl electrophoresis gel (PAGE) and subjected to electrophoresis. Resultant protein fractions were blotted onto a PVDF-membrane (Sigma) and unspecific protein binding was blocked using PBS supplemented with 2% BSA for one hour at room temperature. VEGF protein was detected by employing a polyclonal rabbit anti-serum (Santa Cruz) at a dilution of 1/1000 in PBS supplemented with 0.05% Tween 20 (PBST) and 2% BSA over night at 4° C. followed by repeated washing with PBST and subsequent exposure to an goat anti-rabbit IgG anti-serum coupled to horse-radish peroxidase (HRP; Abcam) at a dilution of 1/10000 for one hour at room temperature. Upon repeated washing, the membrane was exposed to ECL (Sigma) to detect $VEGF_{121}$-6×His using chemiluminescence and exposure to photo-film (Kodak). As shown in FIG. 14*b*, no human VEGF protein was detectable in the supernatants of naïve CHO-S and CHO-S Rec1-I-neo cells serving as negative controls. In addition, only a small amount of VEGF protein was detectable in samples from CHO-S cells transfected and transduced with MigR1Ppgk-$VEGF_{121}$-6×His-I-puro, although these cells had been selected for the expression of the protein by puromycin selection since the expression of the puromycin resistance gene and the VEGF variant are genetically coupled by an IRES. This finding was also observed in supernatants originating from transfected and puromycin-resistant CHO-S Rec1-I-neo cells. In contrast, human His-tagged $VEGF_{121}$ protein was readily detected in CHO-S Rec1 cells transduced only once and greater quantities of the protein were detected in CHO-S Red cells transduced three-times with MLV (PVC-211-Env) vector particles. This finding indicates that multiple retroviral vector particles successfully transduced CHO-S Rec1-I-neo target cells resulting in multiple copies of transfer vectors, which inserted into the host cell genome. These multiple insertions resulted in higher $VEGF_{121}$-6×His protein yields compared to transfection of the plasmid DNA of pMigR1Ppgk-$VEGF_{121}$-6×His-I-puro or the less efficient transduction of CHO-S cells. As demonstrated, the copy number of inserted transfer vectors per CHO-S Rec1-I-cell could be further enhanced upon repeated transduction with MLV (PVC-211-Env) vector particles.

Therefore, this technique of using MLV (PVC-211-Env) retroviral vector particles for the transduction of CHO cells or CHO cells expressing the recombinant receptor Rec1 to yield highly efficient protein producer cells, can be utilised to express many other proteins of interest and is not limited to the expression of cytokines such as VEGF. For example, multimeric proteins such as homo- and hetero-multimeric receptors or immunoglobulins can be produced using the techniques as described in the Examples above and this is shown in the following Examples.

Example 16

Retroviral Expression of Anti IL-15 Antibody 146B7 with CHO-S Rec1 Neo Cells

This example describes the expression of the antibody 146B7, which recognises IL-15, in CHO-S Rec1-neo cells.

HEK cells (HEK 293T; DSMZ) were seeded in a six-well dish at a density of $3 \times 10^5$ cells per well in 2 ml of DMEM supplemented with 10% FCS and 2 mM L-Glutamine. Twenty-four hours later, cells were triple co-transfected with 1 µg of the packaging construct pVPack-GP (Stratagene), 1 µg of the envelope construct pPVC211-env-I-puro and 2 µg of transfer vector in 400 µl of non-supplemented DMEM using FuGENE6® (Roche) according to the manufacturer's instructions. For the generation of retroviral particles coding for the antibody heavy chain, transfer vector pMigR1-EnhP-146B7Vh-sCg-IRES-GFP as described in Example 1.8 (FIG. 15a) was used. For generation of retroviral particles coding for the antibody light chain, transfer vector pMigR1-EnhP-146B7-Vk-Ck-IRES-bcl2 as described in Example 1.8 (FIG. 15b) was used.

Figure 16:
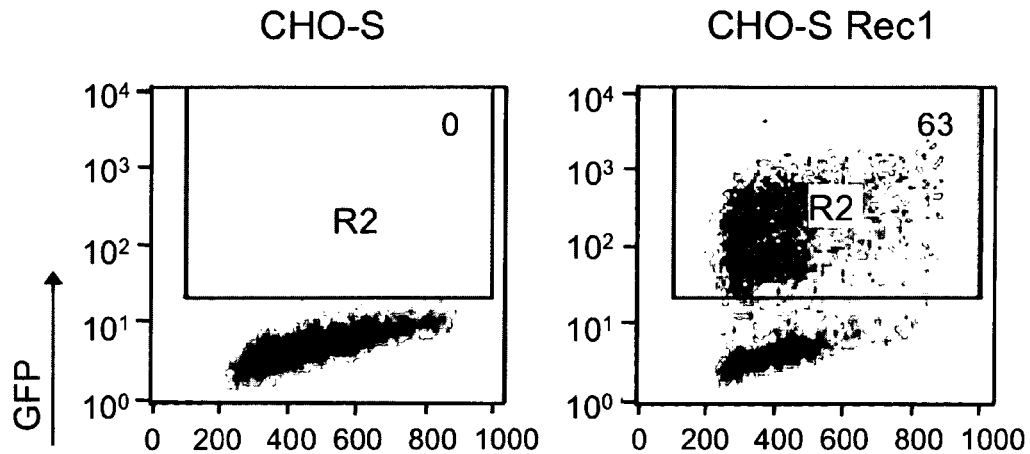
FIG. 16: Comparison of transduction efficiencies 72 h after transduction of MLV-based vector particles displaying the envelope of the molecular clone PVC-211 on CHO-S cells (negative control) and CHO-S cells expressing the recombinant receptor of ecotropic MLV Rec1 (CHO-S Rec1-neo), as indicated. Transduction efficiencies of retroviral particles coding for recombinant antibody heavy chain were analyzed by FACS for GFP reporter gene expression. 63% of the target cells were transduced.

Two days post transfection, cell-free retroviral supernatants were harvested in a 2 ml Eppendorf tube by centrifugation for 5 min at 4° C. with 7,000 rpm in an Eppendorf 5417R centrifuge. The retroviral supernatants were either frozen at −80° C. or were used directly for the transduction of target cells. For the expression of recombinant antibody by co-transduction, 500 µl of retroviral particles coding for the antibody heavy chain and 500 µl of retroviral particles coding for the antibody light chain were added to $2.5 \times 10^5$ CHO-S Rec1-neo cells (see Example 2) in a 2 ml Eppendorf tube. Cells were spun in an Eppendorf 5417R centrifuge for 3 h at 30° C. with 3,300 rpm. Supernatants were discarded and cells were cultivated in SF-IMDM medium supplemented with 2% FCS containing low bovine IgG. After three days, cells were analysed for expression of EGFP to determine efficiency of transduction with retroviral particles (FIG. 16). Concentrations of recombinant human antibody secreted into the culture supernatant were determined by Luminex® assay to be 0.4 µg/ml.

Example 17

Retroviral Expression of Anti-IL-15 Antibody 146B7 Using a Bicistronic Vector in CHO-S Rec1-neo Cells Retroviral particles containing a bicistronic RNA coding for heavy and light chains of recombinant human antibody 146B7 were generated by triple co-transfection of HEK cells with pVPack-GP, pPVC211-env-I-puro, and transfer vector pMigRi-EnhP-146B7-Vh-sCg-IRES-Vk-Ck (Example 1.8; FIG. 17) as described in Example 16. Two days post transfection, cell-free retroviral supernatants were harvested and CHO-S Rec1-neo target cells were transduced with 1 ml of these supernatants according to Example 16.

Three days after transduction and subsequent cultivation, the levels of secreted recombinant human antibody in the culture supernatant were determined by Luminex® assay. Following two further transductions of the CHO-S Rec1-neo target cells, the levels of recombinant human IgG increased over 10 fold to approximately 12 µg/ml, as shown in the table below:

| Transduction No. | IgG (µg/ml) |
|---|---|
| 1 | 1.13 |
| 2 | 2.00 |
| 3 | 11.8 |

Example 18

Retroviral Expression of Anti IL-1β B Cell Receptors on the Surface of Cho-S Rec1-Hygro Cells Retroviral particles coding for heavy or light chains of recombinant human B cell receptors (BCR) were generated by co-transfection of HEK cells with pVPack-GP, pPVC211-env-1-puro, and the transfer vectors pMigR1-EnhP-SK48E26-Vh-sCg-IRES-GFP and pMigR1-EnhP-SK48E26-Vk-Ck-IRES-bcl2 respectively (see Example 1.9), as described in Example 16. Two days post transfection, cell-free retroviral supernatants were harvested and CHO-S Rec1-hygro target cells (See Examples 1.2 and 2) were co-transduced according to Example 16.

Figure 18:
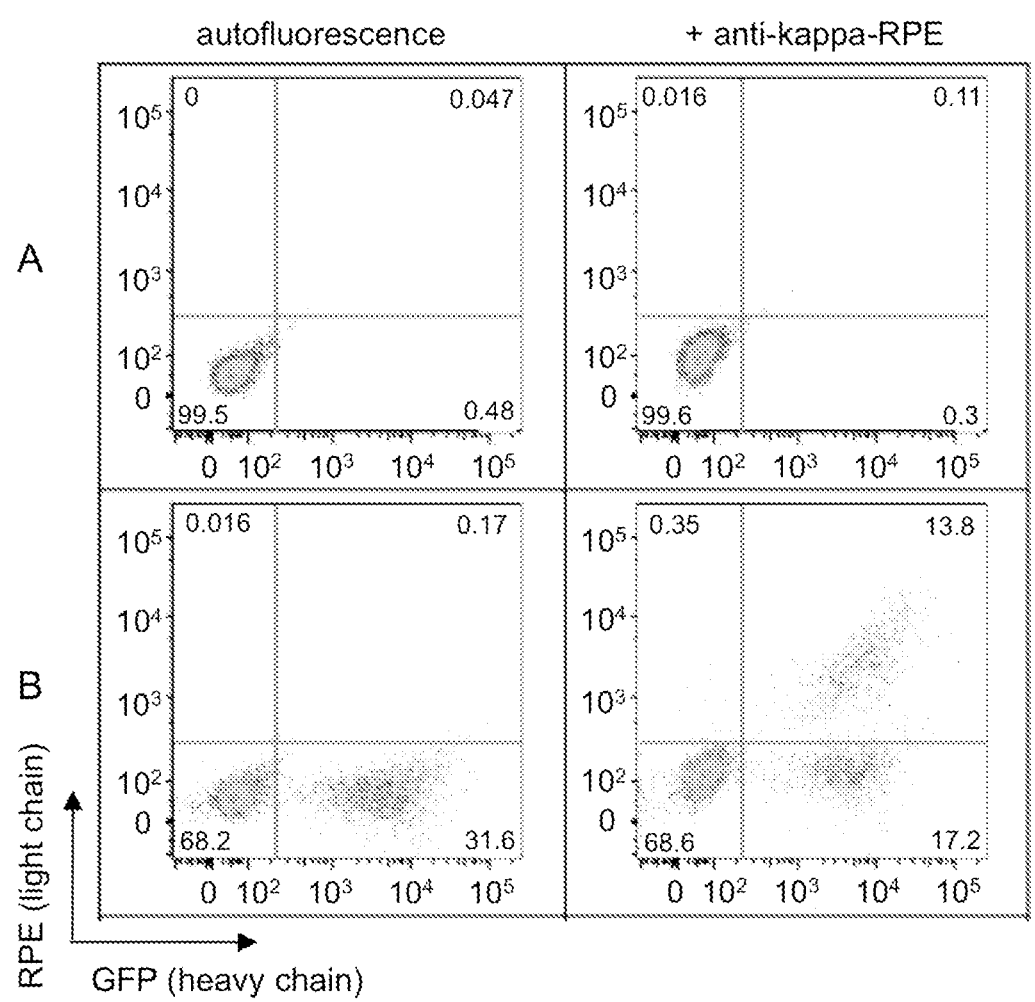
FIG. 18: This figure confirms the expression of anti IL-1β B cell receptor (BCR) on the cell surface of CHO-S Rec1-hygro target cells. After co-transduction with retroviral vectors 14% (Row B, right hand column) of the co-transduced CHO-S Rec1-hygro target cells expressed BCRs on their surface as indicated by GFP and RPE double positive cells. Row A shows the negative control of untransduced CHO-S Rec1-hygro cells. Row B shows CHO-S Rec1-hygro cells co-transduced with the transfer vectors pMigR1-EnhP-SK48E26-Vh-sCg-IRES-GFP and pMigR1-EnhP-SK48E26-Vk-Ck-IRES-bcl2.

Four days after transduction and subsequent cultivation, cells were analysed for expression of GFP using a FACSCalibur™ (Beckton Dickinson) to monitor retroviral expression of BCR heavy chain (FIG. 18). In addition, unpermebealized cells were stained for expression of kappa light chain to confirm cell surface expression of BCR light chain (FIG. 18). The amount of GFP and kappa double positive cells revealed expression of BCR on the surface of 14% of CHO-S Rec1-hygro target cells.

Examples 16, 17 and 18 therefore demonstrate the successful expression of antibody protein in CHO-S Red target cells and the successful expression of B cell receptor protein on CHO-S Rec1 target cells that have been transduced with a retroviral vector psuedotyped with the envelope of molecular clone PVC-211.

Example 19

Retroviral Expression of the Cytokine IL-6 in CHO-S Rec1-neo Cells

This example describes the procedure for expressing the cytokine IL-6 in the host cells CHO-S Rec1-neo.

HEK cells (HEK 293T; DSMZ) are seeded in a six-well dish at a density of $3 \times 10^5$ cells per well in 2 ml of DMEM supplemented with 10% FCS and 2 mM L-Glutamine. Twenty-five hours later, cells are triple co-transfected with 1 µg of the packaging construct pVPack-GP (Stratagene), 1 µg of the envelope construct pPVC211-env-I-puro and 2 µg of transfer vector pMigR1-EnhP-IL-6-IRES-GFP (described in Example 1.10) in 400 µl of non-supplemented DMEM using FuGENE6® (Roche) according to the manufacturer's instructions.

Two days post transfection, cell-free retroviral supernatants are harvested in a 2 ml Eppendorf tube by centrifugation for 5 min at 4° C. with 7,000 rpm in an Eppendorf 5417R centrifuge. The retroviral supernatants are either frozen at −80° C. or are used directly for the transduction of target cells. For the expression of cytokine protein by transduction, 500 µl of retroviral particles coding for IL-6 are added to 2.5×10⁵ CHO-S Rec1-neo cells (see Example 2) in a 2 ml Eppendorf tube. Cells are spun in an Eppendorf 5417R centrifuge for 3 h at 30° C. with 3,300 rpm. Supernatants are discarded and the cells are cultivated in SF-IMDM medium supplemented with 2% FCS containing low bovine IgG. After three days, cells can be analysed for expression of EGFP to determine efficiency of transduction with retroviral particles. Concentrations of IL-6 protein secreted into the culture supernatant can be determined by an appropriate assay such as a Luminex® assay.

Example 20

Retroviral Expression of the Pro-Inflammatory Cytokine TNFα in CHO-S Rec1 Host Cells Retroviral particles coding for the pro-inflammatory cytokine TNFα are generated by triple co-transfection of HEK cells with pVPack-GP, pPVC211-env-I-puro and the transfer vector pMigR1-EnhP-TNFα-IRES-GFP (see Example 1.10), as described in Example 19. Two days post transfection, cell-free retroviral supernatants are harvested and CHO-S Rec1-neo target cells are co-transduced according to Example 19. Three days after transduction and subsequent cultivation, the levels of secreted TNFα protein in the culture supernatant can be determined by Luminex® assay.

Example 21

Retroviral Expression of the Chemokine CCL5 in CHO-S Rec1 Host Cells

Retroviral particles coding for the chemokine CCL5 are generated by triple co-transfection of HEK cells with pVPack-GP, pPVC211-env-I-puro and the transfer vector pMigR1-EnhP-CCL5-IRES-GFP (see Example 1.10), as described in Example 19. Two days post transfection, cell-free retroviral supernatants are harvested and CHO-S Rec1-neo target cells are co-transduced according to Example 19. Three days after transduction and subsequent cultivation, the levels of secreted CCL5 protein in the culture supernatant can be determined by Luminex® assay.

Examples 19, 20 and 21 detail how a number of different proteins of interest can be expressed in CHO-S Rec1 target cells that can be transduced with a retroviral vector psuedotyped with the envelope of molecular clone PVC-211.

LIST OF SEQUENCES

The sequences for the following nucleic acids or amino acids are shown in the appended sequence listing, in which SEQ ID NOS correspond as follows:
1: PVC-211 env molecular clone nucleic acid
2: PVC-211 env molecular clone amino acid
3: MLV envelope (wt-env) nucleic acid
4: MLV envelope (wt-env) amino acid
5: Forward primer—amplification of puroR
6: Reverse primer—amplification of puroR
7: Puromycin resistance gene nucleic acid
8: Puromycin resistance gene amino acid
9: Forward primer—amplification of hygroR
10: Reverse primer—amplification of hygroR
11: Hygromycin resistance gene nucleic acid
12: Hygromycin resistance gene amino acid
13: Forward primer—amplification of bsr
14: Reverse primer—amplification of bsr
15: Blasticidin resistance gene nucleic acid
16: Blasticidin resistance gene amino acid
17: Bleomycin resistance gene nucleic acid
18: Bleomycin resistance gene amino acid
19: Neomycin resistance gene nucleic acid
20: Neomycin resistance gene amino acid
21: Green fluorescent protein nucleic acid
22: Green fluorescent protein amino acid
23: Yellow fluorescent protein nucleic acid
24: Yellow fluorescent protein amino acid
25: Truncated NGFR nucleic acid
26: Truncated NGFR amino acid
27: Truncated CD7 nucleic acid
28: Truncated CD7 amino acid
29: Forward primer—eMLV-R
30: Reverse primer—eMLV-R
31: Rec1 receptor nucleic acid
32: Rec1 receptor amino acid
33: Stuffer sequence
34: Forward primer—Kozak Gag/Pol
35: Reverse primer—MLVgp R1
36: MLV gag/pol nucleic acid
37: MLV gag/pol amino acid
38: Forward primer—Murine Ppgk
39: Reverse primer—Murine Ppgk
40: Murine Ppgk nucleic acid
41: Vkappa promoter ($Pv_\kappa$) nucleic acid
42: pIRES-puro nucleic acid
43: MigR1 vector nucleic acid
44: Forward primer—amplification of $VEGF_{121}$
45: Reverse primer—amplification of $VEGF_{121}$
46: $VEGF_{121}$-6×His nucleic acid
47: $VEGF_{121}$-6×His amino acid
48: murine kappa intron enhancer (KiE) nucleic acid
49: 146B7 Vh nucleic acid
50: 146B7 Vh amino acid
51: sIgH constant region (sCg) nucleic acid
52: sIgH constant region (sCg) amino acid
53: 146B7 Vk nucleic acid
54: 146B7 Vk amino acid
55: kappa constant region (Ck) nucleic acid
56: kappa constant region (Ck) amino acid
57: SK48E26 Vh nucleic acid
58: SK48E26 Vh amino acid
59: SK48E26 Vk nucleic acid
60: SK48E26 Vk amino acid
61: Forward primer murine bcl2A
62: Reverse primer murine bcl2A
63: murine bcl2A nucleic acid
64: IL-6 nucleic acid
65: TNFα nucleic acid
66: CCL5 nucleic acid

REFERENCES

Adam M A, Ramesh N, Miller A D, Osborne W R. (1991) J. Virol. 65(9): 4985-90.
Albritton L M, Tseng L, Scadden D, Cunningham J M. (1989) Cell 57(4): 659-66.
Albritton L M, Kim J W, Tseng L, Cunningham J M. (1993) J. Virol. 67(4): 2091-6.
Bergemann K, Eckermann C, Garidel P, Grammatikos S, Jacobi A. et al. (2007) In Handbook of Therapeutic Antibodies, Chapter 9. Ed Dubel S. Wiley-VCH Verlag GmbH & Co. ISBN 978-3-527-31453-9.
Bleck G T. (2005) Bioprocessing Journal September/October: 1-7.

Coffin J M, Hughes, S H, Varmus, H E. (1997) Eds Retroviruses, Cold Spring Harbor Laboratory Press.
Elder J H, McGee J S, Alexander S. (1986) J. Virol. 57(1): 340-2.
Fischer R, Stoger E, Schillberg S, Christon P, Twyman R M. (2004) Curr. Op. Plant Biol. 7: 152-8.
Gazdar A F, Oie H, Lalley P, Moss W W, Minna J D. (1977) Cell 11(4): 949-56.
Gossen M, Bujard H. (1992) Proc. Natl. Acad. Sci. USA. 89: 5547-51.
Graham F L, Smiley J, Russell W C, Nairn R. (1977) J. Gen. Virol. 36(1): 59-74.
Gray K D, Roth M J. (1993) J. Virol. 67: 3489-96.
Heard J M, Danos O. (1991) J. Virol. 65(8): 4026-32.
Hoffman P M, Cimino E F, Robbins D S, Broadwell R D, Powers J M, Ruscetti S K. (1992) Lab Invest. 67(3): 314-21.
Jacobsen L B, Calvin S A, Colvin, K E, Wright M. (2004) Transfection of Mammalian Cells—Methods 33: 104-12.
Kai K & Furuta T. (1984) J. Virol. 50: 970-3.
Koch W, Hunsmann G, Friedrich R. (1983) J. Virol. 45(1): 1-9.
Lever A, Gottlinger H, Haseltine W, Sodroski J. (1989) J. Virol. 63(9): 4085-7.
Masuda M, Remington M P, Hoffman P M, Ruscetti S K. (1992) J. Virol. 66(5): 2798-806.
Mann R, Baltimore D. (1985) J. Virol. 54(2): 401-7.
Masuda M, Hoffman P M, Ruscetti S K. (1993) J. Virol. 67(8): 4580-7.
Masuda M, Hanson C A, Alvord W G, Hoffman P M, Ruscetti S K, Masuda M. (1996a Virology 215(2): 142-51.
Masuda M, Masuda M, Hanson C A, Hoffman P M, Ruscetti S K. (1996b) J. Virol. 70(12): 8534-9.
Mather J P. (1980) Biol. Reprod. 23(1): 243-52.
Mather J P, Zhuang L Z, Perez-Infante V, Phillips D M. (1982) Ann. NY Acad. Sci. 383: 44-68.
Miller D G, Miller A D. (1992) J. Virol. 66(1): 78-84.
Oie H K, Gazdar A F, Lalley P A, Russell E K, Minna J D et al. (1978) Nature 274: 60-62.
Ott D, Friedrich R, Rein A. (1990) J. Virol. 64(2): 757-66.
Pear W S, Miller J P, Xu L, Pui J C, Soffer B et al. (1998) Blood 92(10): 3780-92.
Remington M P, Hoffman P M, Ruscetti S K, Masuda M. (1992) Nuc. Acids Res. 20(12): 3249.
Richmond J Y & McKinney R W. (1993) Biosafety in Microbiological and Biomedical Laboratories. US Department of Health and Human Services, CDC/NIH, 3rd Edition. US Government Printing Office, Washington, D.C.
Ruddle N H, Conta B S, Leinwand L, Kozak C, Ruddle F et al. (1978) J. Exp. Med. 148 (2): 451-65.
Shinnick T M, Lerner R A, Sutcliffe J G. (1981) Nature 293: 543-8.
Siess D C, Kozak S L, Kabat D. (1996) J. Virol. 70(6): 3432-9.
Wilson C A, Eiden M V. (1991) J. Virol. 65(11): 5975-82.
Wildt S, Gerngross T U. (2005) Nat. Rev. Microbiol. 3: 119-28.
Yee J K, Miyanohara A, LaPorte P, Bouic K, Burns J C, Friedmann T. (1994) Proc. Natl. Acad. Sci. USA. 91(20): 9564-8.
Yu S F, von Ruden T, Kantoff P W, Garber C, Seiberg M et al. (1986) Proc. Natl. Acad. Sci. USA. 83(10): 3194-8.
Zufferey R, Donello J E, Trono D, Hope T J. (1999) J. Virol. 73(4): 2886-92.
WO 86/005807 A1: Kenton J H & Boss M A.
WO 87/004462 A1: Wilson R H & Bebbington C R.
WO 89/010404 A1: Bebbington C R & Yarranton G T.
WO 91/006657 A1: Bebbington C R & Yarranton G T.
WO 95/001997 A1; Young P R, Gross M S & Jonak Z L.

The invention claimed is:

1. A method for transducing a host cell, said method comprising transducing the host cell with a retroviral vector particle comprising an envelope of Friend murine leukaemia virus, wherein the envelope of Friend murine leukaemia virus is encoded by molecular clone PVC-211 (SEQ ID NO: 1) and wherein the host cell recombinantly expresses a Rec1 receptor.

2. The method of claim 1, wherein susceptibility of the host cell to transduction is increased.

3. The method according to claim 1, wherein the retroviral vector particle further comprises an expressible heterologous nucleotide sequence encoding a protein of interest.

4. The method according to claim 3, further comprising the step of culturing the host cell under conditions to produce the protein of interest.

5. The method according to claim 4, wherein said culturing step produces the protein of interest at a concentration of at least 1 mg/L.

6. The method according to claim 1, wherein the host cell is a hamster cell.

7. The method according to claim 1, wherein the host cell is a Chinese hamster ovary (CHO) cell.

8. The method according to claim 3, wherein the protein of interest is selected from the group consisting of: interferons, erythropoietin, Factor VIII, clotting factors, antibodies, insulin, chemokines, cytokines, growth factors, angiogenesis modulatory factors, apoptosis modulatory factors and vaccines.

9. The method according to claim 3, wherein the retroviral vector particle comprises at least two heterologous nucleotide sequences coding for at least two different proteins of interest.

10. The method according to claim 9, wherein the at least two proteins of interest are an immunoglobulin heavy chain and an immunoglobulin light chain.

11. The method according to claim 1, wherein the retroviral vector particle is produced by a retroviral packaging system comprising:

a) an envelope construct comprising a promoter operably linked to an envelope coding sequence of a Friend murine leukaemia virus, wherein the envelope of Friend murine leukaemia virus is encoded by molecular clone PVC-211 (SEQ ID NO: 1);

b) a packaging construct comprising a promoter operably linked to a nucleotide sequence encoding a retroviral gag and pol; and c) a retroviral transfer vector.

12. The method of claim 11, wherein the retroviral packaging system is expressed in a host cell under conditions effective to produce a retroviral vector particle.

13. A host cell line transduced with a retroviral vector particle comprising an envelope of Friend murine leukaemia virus encoded by the molecular clone PVC-211 (SEQ ID NO: 1), wherein the host cell line recombinantly expresses a Rec1 receptor.

14. The host cell line according to claim 13, wherein the host cell line produces a protein of interest encoded by the retroviral vector.

15. The host cell line according to claim 14, wherein the protein of interest is produced by the cell line at a concentration of at least 1 mg/L.

16. A system for transducing a host cell, comprising:

a) a retroviral vector particle comprising an envelope of Friend murine leukaemia virus encoded by the molecular clone PVC-211 (SEQ ID NO: 1); and b) a target host cell which recombinantly expresses a Rec1 receptor.

17. The host cell line of claim 13, wherein the cell is a hamster cell.

18. The host cell line of claim 17, wherein the hamster cell is a Chinese hamster ovary (CHO) cell.

19. The method of claim 1, wherein the Rec1 receptor has the sequence of SEQ ID NO: 32.

20. The system of claim 16, wherein the Rec1 receptor has the sequence of SEQ ID NO: 32.

* * * * *

SEQUENCE LISTING

```
<160> NUMBER OF SEQ ID NOS: 66

<210> SEQ ID NO 1
<211> LENGTH: 2031
<212> TYPE: DNA
<213> ORGANISM: Friend murine leukemia virus
<220> FEATURE:
<223> OTHER INFORMATION: PVC-211 env nucleic acid

<400> SEQUENCE: 1
atggcgtgtt caacgctctc aaaatcccct aaagataaga ttgaccgcg  ggacctccta      60 atccccttaa ttctcttcct gtctctcaaa ggggccagat ccgcagcacc cggctctagc     120
cctcaccagg tctacaatat tacctgggaa gtgaccaatg gggatcggga gacagtatgg     180
gcaatatcag gcaaccaccc tctgtggact tggtggccag acctcacccc agatttgtgt     240
atgttagctc tcagtgggcc gccccactgg gggctagagt atcgggcccc ctattcctcg     300 ccccgggc cccttgttg ctcagggagc agcgggaaca gggcaggctg cgccagagac        360
tgcgacgagc ccttgacctc cctcacccct cggtgcaaca ctgcctggaa cagacttaag     420
ctggaccagg taactcataa atcgagtggg ggattttatg tctgcccgg gtcacatcgc      480 ccccggaaag ccaagtcctg tggggtcca gactccttct actgtgcctc ttggggctgc      540
gagacaaccg gtagagcata ctggaagccc tcctcatctt gggactacat cacagtagac     600
aacaatctca ccactaacca ggctgctcag gtatgcaaag acaataagtg gtgcaatccc     660
ttggctatcc agtttacaaa cgccgggaaa caggtcacct catggacaat tggacactat     720
```

```
tggggtctac gtctttatgt ctctgggcag gacccggggc ttactttcgg gatccgactc      780
aaatatcaaa atctaggacc tcgggtccca ataggaccga accccgtcct ggcagaccaa      840
ctttcgttcc cgctacctaa tcccctaccc aaacctgcca agtctccctc cgcctctaat      900
tcgactccta cattgatttc cccgtcccca gctcccactc agccccgcc agcaggaacg      960 ggagacaggt tactaaatct agtacaggga gcttaccagg cactcaacct taccaaccct     1020
gataaaactc aagagtgctg ttatgcctaa gtgtctgcac ccccctatta cgagggggtt     1080
gcggtcctag gtacttattc caaccatacc tctgccccag ctaactgctc cgcgggctcc     1140
caacacaagc tgaccctgtc cgaagtgact ggacagggac tctgcatagg aacagtccca     1200
aaaactcacc aggccctgtg caacactacc cttaagacag gcaaagggtc ttactatcta     1260
gttgcccccg caggaactat gtgggcatgt aacaccggac tcactccatg cctatccgcc     1320
accgtgctta atcgcaccac tgactactgc gttctcgtag aattatggcc cagggtcacc     1380
taccatcctc ccagttacgt ctatagccag tttgaaaaat cctatagaca taaaagagaa     1440
ccagtgtcct taaccttggc cttattatta ggtgggctaa ctatgggtgg catcgccgcg     1500
ggagtaggga caggaactac cgccctggtc gccacccagc agtttcagca gctccatgct     1560
gccgtacaag atgatctcaa agaagttgaa aagtcaatta ctaacctaga aaagtctctt     1620
acttcattgt ctgaggttgt actgcagaat cgacgaggcc tagacctgtt gttcctaaaa     1680
gaaggaggac tgtgtgctgc cctaaaagaa gaatgttgtt tctatgctga ccatactggc     1740
ctagtaagag atagtatggc caaattaaga gagagactca ctcagagaca aaaactattt     1800
gagtcgagcc aaggatggtt cgaaggattg tttaacagat cccctggtt taccacgttg     1860 atatccacca tcatggggcc tctcattata ctcctactaa ttctgctttt tggaccctgc     1920
attcttaatc gattagttca atttgttaaa gacaggatct cagtagtcca ggctttagtc     1980
ctgactcaac aataccacca gctaaaacca ctagaatacg agccacaata a              2031
```

<210> SEQ ID NO 2
<211> LENGTH: 676
<212> TYPE: PRT
<213> ORGANISM: Friend murine leukemia virus
<220> FEATURE:
<223> OTHER INFORMATION: PVC-211 env amino acid

<400> SEQUENCE: 2

Met Ala Cys Ser Thr Leu Ser Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His Gln Val Tyr Asn Ile Thr
        35                  40                  45

Trp Glu Val Thr Asn Gly Asp Arg Glu Thr Val Trp Ala Ile Ser Gly
    50                  55                  60

Asn His Pro Leu Trp Thr Trp Pro Asp Leu Thr Pro Asp Leu Cys
65                  70                  75                  80

Met Leu Ala Leu Ser Gly Pro Pro His Trp Gly Leu Glu Tyr Arg Ala
                85                  90                  95

Pro Tyr Ser Ser Pro Pro Gly Pro Cys Cys Ser Gly Ser Ser Gly
            100                 105                 110

Asn Arg Ala Gly Cys Ala Arg Asp Cys Asp Glu Pro Leu Thr Ser Leu
        115                 120                 125

Thr Pro Arg Cys Asn Thr Ala Trp Asn Arg Leu Lys Leu Asp Gln Val

-continued

```
                130                 135                 140
Thr His Lys Ser Ser Gly Gly Phe Tyr Val Cys Pro Gly Ser His Arg
145                 150                 155                 160
Pro Arg Lys Ala Lys Ser Cys Gly Gly Pro Asp Ser Phe Tyr Cys Ala
                165                 170                 175
Ser Trp Gly Cys Glu Thr Thr Gly Arg Ala Tyr Trp Lys Pro Ser Ser
                180                 185                 190
Ser Trp Asp Tyr Ile Thr Val Asp Asn Asn Leu Thr Thr Asn Gln Ala
                195                 200                 205
Ala Gln Val Cys Lys Asp Asn Lys Trp Cys Asn Pro Leu Ala Ile Gln
                210                 215                 220
Phe Thr Asn Ala Gly Lys Gln Val Thr Ser Trp Thr Ile Gly His Tyr
225                 230                 235                 240
Trp Gly Leu Arg Leu Tyr Val Ser Gly Gln Asp Pro Gly Leu Thr Phe
                245                 250                 255
Gly Ile Arg Leu Lys Tyr Gln Asn Leu Gly Pro Arg Val Pro Ile Gly
                260                 265                 270
Pro Asn Pro Val Leu Ala Asp Gln Leu Ser Phe Pro Leu Pro Asn Pro
                275                 280                 285
Leu Pro Lys Pro Ala Lys Ser Pro Ser Ala Ser Asn Ser Thr Pro Thr
290                 295                 300
Leu Ile Ser Pro Ser Pro Ala Pro Thr Gln Pro Pro Ala Gly Thr
305                 310                 315                 320
Gly Asp Arg Leu Leu Asn Leu Val Gln Gly Ala Tyr Gln Ala Leu Asn
                325                 330                 335
Leu Thr Asn Pro Asp Lys Thr Gln Glu Cys Trp Leu Cys Leu Val Ser
                340                 345                 350
Ala Pro Pro Tyr Tyr Glu Gly Val Ala Val Leu Gly Thr Tyr Ser Asn
                355                 360                 365
His Thr Ser Ala Pro Ala Asn Cys Ser Ala Gly Ser Gln His Lys Leu
                370                 375                 380
Thr Leu Ser Glu Val Thr Gly Gln Gly Leu Cys Ile Gly Thr Val Pro
385                 390                 395                 400
Lys Thr His Gln Ala Leu Cys Asn Thr Thr Leu Lys Thr Gly Lys Gly
                405                 410                 415
Ser Tyr Tyr Leu Val Ala Pro Ala Gly Thr Met Trp Ala Cys Asn Thr
                420                 425                 430
Gly Leu Thr Pro Cys Leu Ser Ala Thr Val Leu Asn Arg Thr Thr Asp
                435                 440                 445
Tyr Cys Val Leu Val Glu Leu Trp Pro Arg Val Thr Tyr His Pro Pro
450                 455                 460
Ser Tyr Val Tyr Ser Gln Phe Glu Lys Ser Tyr Arg His Lys Arg Glu
465                 470                 475                 480
Pro Val Ser Leu Thr Leu Ala Leu Leu Leu Gly Gly Leu Thr Met Gly
                485                 490                 495
Gly Ile Ala Ala Gly Val Gly Thr Gly Thr Thr Ala Leu Val Ala Thr
                500                 505                 510
Gln Gln Phe Gln Gln Leu His Ala Ala Val Gln Asp Asp Leu Lys Glu
                515                 520                 525
Val Glu Lys Ser Ile Thr Asn Leu Glu Lys Ser Leu Thr Ser Leu Ser
                530                 535                 540
Glu Val Val Leu Gln Asn Arg Arg Gly Leu Asp Leu Leu Phe Leu Lys
545                 550                 555                 560
```

```
Glu Gly Gly Leu Cys Ala Ala Leu Lys Glu Glu Cys Cys Phe Tyr Ala
            565                 570                 575

Asp His Thr Gly Leu Val Arg Asp Ser Met Ala Lys Leu Arg Glu Arg
            580                 585                 590

Leu Thr Gln Arg Gln Lys Leu Phe Glu Ser Ser Gln Gly Trp Phe Glu
            595                 600                 605

Gly Leu Phe Asn Arg Ser Pro Trp Phe Thr Thr Leu Ile Ser Thr Ile
            610                 615                 620

Met Gly Pro Leu Ile Ile Leu Leu Leu Ile Leu Leu Phe Gly Pro Cys
625                 630                 635                 640

Ile Leu Asn Arg Leu Val Gln Phe Val Lys Asp Arg Ile Ser Val Val
            645                 650                 655

Gln Ala Leu Val Leu Thr Gln Gln Tyr His Gln Leu Lys Pro Leu Glu
            660                 665                 670

Tyr Glu Pro Gln
        675

<210> SEQ ID NO 3
<211> LENGTH: 1998
<212> TYPE: DNA
<213> ORGANISM: Murine leukemia virus
<220> FEATURE:
<223> OTHER INFORMATION: MLV env nucleic acid

<400> SEQUENCE: 3
atggcgcgtt caacgctctc aaaccccctt aaaaataagg ttaacccgcg aggccccta      60 atccccttaa ttcttctgat gctcagaggg gtcagtactg cttcgcccgg ctccagtcct    120
catcaagtct ataatatcac ctgggaggta accaatggag atcggagac ggtatgggca     180 acttctggca accaccctct gtggacctgg tggcctgacc ttccccaga tttatgtatg     240 ttagcccacc atggaccatc ttattggggg ctagaatatc aatcccctt ttcttctccc     300 ccggggcccc cttgttgctc aggggcagc agcccaggct gttccagaga ctgcgaagaa     360
cctttaacct ccctcacccc tcggtgcaac actgcctgga acagactcaa gctagaccag    420
acaactcata aatcaaatga gggattttat gtttgccccg ggccccaccg ccccgagaa     480 tccaagtcat gtgggggtcc agactccttc tactgtgcct attggggctg tgagacaacc    540
ggtagagctt actggaagcc ctcctcatca tgggatttca tcacagtaaa caacaatctc    600
acctctgacc aggctgtcca ggtatgcaaa gataataagt ggtgcaaccc cttagttatt    660
cggtttacag acgccgggag acgggttact tcctggacca caggacatta ctggggctta    720
cgtttgtatg tctccggaca agatccaggg cttacatttg gatccgact cagataccaa    780 aatctaggac cccgcgtccc aataggggcca accccgttc tggcagacca acagccactc    840
tccaagccca aacctgttaa gtcgccttca gtcaccaaac acccagtgg gactcctctc    900 tcccctaccc aacttccacc ggcgggaacg gaaaataggc tgctaaactt agtagacgga    960
gcctaccaag ccctcaacct caccagtcct gacaaaaccc aagagtgctg gttgtgtcta   1020
gtagcgggac cccctacta cgaagggtt gccgtcctgg gtacctactc caaccatacc     1080
tctgctccag ccaactgctc cgtggcctcc caacacaagt tgaccctgtc cgaagtgacc    1140 ggacaggac tctgcatagg agcagttccc aaaacacatc aggccctatg taataccacc    1200
cagacaagca gtcgagggtc ctattatcta gttgccccta caggtaccat gtgggcttgt    1260 agtaccggc ttactccatg catctccacc accatactga accttaccac tgattattgt   1320
gttcttgtcg aactctggcc aagagtcacc tatcattccc ccagctatgt ttacggcctg    1380
```

-continued

```
tttgagagat ccaaccgaca caaaagagaa ccggtgtcgt taaccctggc cctattattg    1440
ggtggactaa ccatgggggg aattgccgct ggaataggaa cagggactac tgctctaatg    1500
gccactcagc aattccagca gctccaagcc gcagtacagg atgatctcag ggaggttgaa    1560
aaatcaatct ctaacctaga aaagtctctc acttccctgt ctgaagttgt cctacagaat    1620
cgaaggggcc tagacttgtt atttctaaaa gaaggagggc tgtgtgctgc tctaaaagaa    1680
gaatgttgct tctatgcgga ccacacagga ctagtgagag acagcatggc caaattgaga    1740
gagaggctta atcagagaca gaaactgttt gagtcaactc aaggatggtt tgagggactg    1800
tttaacagat ccccttggtt taccaccttg atatctacca ttatgggacc ctcattgtaa    1860
ctcctaatga ttttgctctt cggaccctgc attcttaatc gattagtcca atttgttaaa    1920
gacaggatat cagtggtcca ggctctagtt ttgactcaac aatatcacca gctgaagcct    1980
atagagtacg agccatag                                                   1998
```

<210> SEQ ID NO 4
<211> LENGTH: 665
<212> TYPE: PRT
<213> ORGANISM: Murine leukemia virus
<220> FEATURE:
<223> OTHER INFORMATION: MLV env amino acid

<400> SEQUENCE: 4

```
Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
                20                  25                  30

Thr Ala Ser Pro Gly Ser Ser Pro His Gln Val Tyr Asn Ile Thr Trp
            35                  40                  45

Glu Val Thr Asn Gly Asp Arg Glu Thr Val Trp Ala Thr Ser Gly Asn
        50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Gly Ser Ser Pro
                100                 105                 110

Gly Cys Ser Arg Asp Cys Glu Glu Pro Leu Thr Ser Leu Thr Pro Arg
            115                 120                 125

Cys Asn Thr Ala Trp Asn Arg Leu Lys Leu Asp Gln Thr Thr His Lys
130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
        195                 200                 205

Cys Lys Asp Asn Lys Trp Cys Asn Pro Leu Val Ile Arg Phe Thr Asp
    210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255
```

-continued

Leu Arg Tyr Gln Asn Leu Gly Pro Arg Val Pro Ile Gly Pro Asn Pro
            260                 265                 270

Val Leu Ala Asp Gln Gln Pro Leu Ser Lys Pro Lys Pro Val Lys Ser
            275                 280                 285

Pro Ser Val Thr Lys Pro Pro Ser Gly Thr Pro Leu Ser Pro Thr Gln
            290                 295                 300

Leu Pro Pro Ala Gly Thr Glu Asn Arg Leu Leu Asn Leu Val Asp Gly
305                 310                 315                 320

Ala Tyr Gln Ala Leu Asn Leu Thr Ser Pro Asp Lys Thr Gln Glu Cys
            325                 330                 335

Trp Leu Cys Leu Val Ala Gly Pro Pro Tyr Tyr Glu Gly Val Ala Val
            340                 345                 350

Leu Gly Thr Tyr Ser Asn His Thr Ser Ala Pro Ala Asn Cys Ser Val
            355                 360                 365

Ala Ser Gln His Lys Leu Thr Leu Ser Glu Val Thr Gly Gln Gly Leu
            370                 375                 380

Cys Ile Gly Ala Val Pro Lys Thr His Gln Ala Leu Cys Asn Thr Thr
385                 390                 395                 400

Gln Thr Ser Ser Arg Gly Ser Tyr Tyr Leu Val Ala Pro Thr Gly Thr
            405                 410                 415

Met Trp Ala Cys Ser Thr Gly Leu Thr Pro Cys Ile Ser Thr Thr Ile
            420                 425                 430

Leu Asn Leu Thr Thr Asp Tyr Cys Val Leu Val Glu Leu Trp Pro Arg
            435                 440                 445

Val Thr Tyr His Ser Pro Ser Tyr Val Tyr Gly Leu Phe Glu Arg Ser
            450                 455                 460

Asn Arg His Lys Arg Glu Pro Val Ser Leu Thr Leu Ala Leu Leu Leu
465                 470                 475                 480

Gly Gly Leu Thr Met Gly Gly Ile Ala Ala Gly Ile Gly Thr Gly Thr
            485                 490                 495

Thr Ala Leu Met Ala Thr Gln Gln Phe Gln Gln Leu Gln Ala Ala Val
            500                 505                 510

Gln Asp Asp Leu Arg Glu Val Glu Lys Ser Ile Ser Asn Leu Glu Lys
            515                 520                 525

Ser Leu Thr Ser Leu Ser Glu Val Val Leu Gln Asn Arg Arg Gly Leu
            530                 535                 540

Asp Leu Leu Phe Leu Lys Glu Gly Gly Leu Cys Ala Ala Leu Lys Glu
545                 550                 555                 560

Glu Cys Cys Phe Tyr Ala Asp His Thr Gly Leu Val Arg Asp Ser Met
            565                 570                 575

Ala Lys Leu Arg Glu Arg Leu Asn Gln Arg Gln Lys Leu Phe Glu Ser
            580                 585                 590

Thr Gln Gly Trp Phe Glu Gly Leu Phe Asn Arg Ser Pro Trp Phe Thr
            595                 600                 605

Thr Leu Ile Ser Thr Ile Met Gly Pro Leu Ile Val Leu Leu Met Ile
            610                 615                 620

Leu Leu Phe Gly Pro Cys Ile Leu Asn Arg Leu Val Gln Phe Val Lys
625                 630                 635                 640

Asp Arg Ile Ser Val Val Gln Ala Leu Val Leu Thr Gln Gln Tyr His
            645                 650                 655

Gln Leu Lys Pro Ile Glu Tyr Glu Pro
            660                 665

<210> SEQ ID NO 5

```
<211> LENGTH: 35
<212> TYPE: DNA
<213> ORGANISM: Artificial Sequence
<220> FEATURE:
<223> OTHER INFORMATION: Forward Primer puroR

<400> SEQUENCE: 5
ataacccggg atgaccgagt acaagcccac ggtgc                              35

<210> SEQ ID NO 6
<211> LENGTH: 32
<212> TYPE: DNA
<213> ORGANISM: Artificial Sequence
<220> FEATURE:
<223> OTHER INFORMATION: Reverse Primer puroR

<400> SEQUENCE: 6
attatctaga tcaggcaccg ggcttgcggg tc                                 32

<210> SEQ ID NO 7
<211> LENGTH: 600
<212> TYPE: DNA
<213> ORGANISM: Streptomyces alboniger
<220> FEATURE:
<223> OTHER INFORMATION: Puromycin resistance gene

<400> SEQUENCE: 7
atgaccgagt acaagcccac ggtgcgcctc gccacccgcg acgacgtccc cagggccgta   60
cgcaccctcg ccgccgcgtt cgccgactac cccgccacgc gccacaccgt cgatccggac  120
cgccacatcg agcgggtcac cgagctgcaa gaactcttcc tcacgcgcgt cgggctcgac  180
atcggcaagg tgtgggtcgc ggacgacggc gccgcggtgg cggtctggac cacgccggag  240
agcgtcgaag cgggggcggt gttcgccgag atcggcccgc gcatggccga gttgagcggt  300
tcccggctgg ccgcgcagca acagatggaa ggcctcctgg cgccgcaccg gcccaaggag  360
cccgcgtggt tcctggccac cgtcggcgtc tcgcccgacc accagggcaa gggtctgggc  420
agcgccgtcg tgctccccgg agtggaggcg gccgagcgcg ccggggtgcc cgccttcctg  480
gagacctccg cgccccgcaa cctccccttc tacgagcggc tcggcttcac cgtcaccgcc  540
gacgtcgagg tgcccgaagg accgcgcacc tggtgcatga cccgcaagcc cggtgcctga  600

<210> SEQ ID NO 8
<211> LENGTH: 199
<212> TYPE: PRT
<213> ORGANISM: Streptomyces alboniger
<220> FEATURE:
<223> OTHER INFORMATION: Puromycin resistance gene

<400> SEQUENCE: 8

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95
```

```
Glu Leu Ser Gly Ser Arg Leu Ala Ala Gln Gln Gln Met Glu Gly Leu
                100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
130                 135                 140

Leu Pro Gly Val Glu Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
            195

<210> SEQ ID NO 9
<211> LENGTH: 47
<212> TYPE: DNA
<213> ORGANISM: Artificial Sequence
<220> FEATURE:
<223> OTHER INFORMATION: Forward Primer hygroR

<400> SEQUENCE: 9
aattaatcat gacccgggac catgaaaaag cctgaactca ccgcgac                    47

<210> SEQ ID NO 10
<211> LENGTH: 51
<212> TYPE: DNA
<213> ORGANISM: Artificial Sequence
<220> FEATURE:
<223> OTHER INFORMATION: Reverse Primer hygroR

<400> SEQUENCE: 10
aattaagtcg acgcggccgc tctagactat tcctttgccc tcggacgagt g              51

<210> SEQ ID NO 11
<211> LENGTH: 1026
<212> TYPE: DNA
<213> ORGANISM: Streptomyces hygroscopicus
<220> FEATURE:
<223> OTHER INFORMATION: Hygromycin resistance gene

<400> SEQUENCE: 11
atgaaaaagc ctgaactcac cgcgacgtct gtcgagaagt ttctgatcga aaagttcgac     60
agcgtctccg acctgatgca gctctcggag ggcgaagaat ctcgtgcttt cagcttcgat    120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
```

-continued

```
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026

<210> SEQ ID NO 12
<211> LENGTH: 341
<212> TYPE: PRT
<213> ORGANISM: Streptomyces hygroscopicus
<220> FEATURE:
<223> OTHER INFORMATION: Hygromycin resistance gene

<400> SEQUENCE: 12

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
                20                  25                  30

Glu Ser Arg Ala Phe Ser Phe Asp Val Gly Gly Arg Gly Tyr Val Leu
            35                  40                  45

Arg Val Asn Ser Cys Ala Asp Gly Phe Tyr Lys Asp Arg Tyr Val Tyr
        50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320
```

```
Cys Val Glu Val Leu Ala Asp Ser Gly Asn Arg Arg Pro Ser Thr Arg
            325                 330                 335

Pro Arg Ala Lys Glu
            340

<210> SEQ ID NO 13
<211> LENGTH: 49
<212> TYPE: DNA
<213> ORGANISM: Artificial Sequence
<220> FEATURE:
<223> OTHER INFORMATION: Forward Primer bsr

<400> SEQUENCE: 13
aattaacccg ggaccatgaa aacatttaac atttctcaac aagatctag              49

<210> SEQ ID NO 14
<211> LENGTH: 42
<212> TYPE: DNA
<213> ORGANISM: Artificial Sequence
<220> FEATURE:
<223> OTHER INFORMATION: Reverse Primer bsr

<400> SEQUENCE: 14
aattaaacta gtttaatttc gggtatattt gagtggaatg ag                     42

<210> SEQ ID NO 15
<211> LENGTH: 423
<212> TYPE: DNA
<213> ORGANISM: Bacillus cereus
<220> FEATURE:
<223> OTHER INFORMATION: Blasticidin resistance gene

<400> SEQUENCE: 15
atgaaaacat ttaacatttc tcaacaagat ctagaattag tagaagtagc gacagagaag   60
attacaatgc tttatgagga taataaacat catgtgggag cggcaattcg tacgaaaaca  120
ggagaaatca tttcggcagt acatattgaa gcgtatatag acgagtaac tgtttgtgca   180 gaagccattg cgattggtag tgcagtttcg aatggacaaa aggattttga cacgattgta  240
gctgttagac acccttattc tgacgaagta gatagaagta ttcgagtggt aagtccttgt  300
ggtatgtgta gggagttgat ttcagactat gcaccagatt gttttgtgtt aatagaaatg  360
aatggcaagt tagtcaaaac tacgattgaa gaactcattc cactcaaata cccgaaat    420 taa                                                               423

<210> SEQ ID NO 16
<211> LENGTH: 140
<212> TYPE: PRT
<213> ORGANISM: Bacillus cereus
<220> FEATURE:
<223> OTHER INFORMATION: Blasticidin resistance gene

<400> SEQUENCE: 16

Met Lys Thr Phe Asn Ile Ser Gln Gln Asp Leu Glu Leu Val Glu Val
1               5                   10                  15

Ala Thr Glu Lys Ile Thr Met Leu Tyr Glu Asp Asn Lys His His Val
                20                  25                  30

Gly Ala Ala Ile Arg Thr Lys Thr Gly Glu Ile Ile Ser Ala Val His
            35                  40                  45

Ile Glu Ala Tyr Ile Gly Arg Val Thr Val Cys Ala Glu Ala Ile Ala
        50                  55                  60

Ile Gly Ser Ala Val Ser Asn Gly Gln Lys Asp Phe Asp Thr Ile Val
```

```
                    65                  70                  75                  80
Ala Val Arg His Pro Tyr Ser Asp Glu Val Asp Arg Ser Ile Arg Val
                85                  90                  95

Val Ser Pro Cys Gly Met Cys Arg Glu Leu Ile Ser Asp Tyr Ala Pro
            100                 105                 110

Asp Cys Phe Val Leu Ile Glu Met Asn Gly Lys Leu Val Lys Thr Thr
        115                 120                 125

Ile Glu Glu Leu Ile Pro Leu Lys Tyr Thr Arg Asn
    130                 135                 140

<210> SEQ ID NO 17
<211> LENGTH: 375
<212> TYPE: DNA
<213> ORGANISM: Staphylococcus aureus
<220> FEATURE:
<223> OTHER INFORMATION: Bleomycin resistance gene

<400> SEQUENCE: 17
atggccaagt tgaccagtgc cgttccggtg ctcaccgcgc gcgacgtcgc cggagcggtc        60
gagttctgga ccgaccggct cgggttctcc cggacttcg tggaggacga cttcgccggt       120
gtggtccggg acgacgtgac cctgttcatc agcgcggtcc aggaccaggt ggtgccggac       180
aacaccctgg cctgggtgtg ggtgcgcggc ctggacgagc tgtacgccga gtggtcggag       240
gtcgtgtcca cgaacttccg ggacgcctcc gggccggcca tgaccgagat cggcgagcag       300
ccgtgggggc gggagttcgc cctgcgcgac ccggccggca actgcgtgca cttcgtggcc       360
gaggagcagg actga                                                       375

<210> SEQ ID NO 18
<211> LENGTH: 124
<212> TYPE: PRT
<213> ORGANISM: Staphylococcus aureus
<220> FEATURE:
<223> OTHER INFORMATION: Bleomycin resistance gene

<400> SEQUENCE: 18

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 19
<211> LENGTH: 804
<212> TYPE: DNA
<213> ORGANISM: Escherichia coli
<220> FEATURE:
<223> OTHER INFORMATION: Neomycin resistance gene
```

-continued

```
<400> SEQUENCE: 19
atgggatcgg ccattgaaca agatggattg cacgcaggtt ctccggccgc ttgggtggag      60
aggctattcg gctatgactg ggcacaacag acaatcggct gctctgatgc cgccgtgttc     120
cggctgtcag cgcaggggcg cccggttctt tttgtcaaga ccgacctgtc cggtgccctg     180
aatgaactgc aggacgaggc agcgcggcta tcgtggctgg ccacgacggg cgttccttgc     240
gcagctgtgc tcgacgttgt cactgaagcg ggaagggact ggctgctatt gggcgaagtg     300
ccggggcagg atctcctgtc atctcacctt gctcctgccg agaaagtatc catcatggct     360
gatgcaatgc ggcggctgca tacgcttgat ccggctacct gcccattcga ccaccaagcg     420
aaacatcgca tcgagcgagc acgtactcgg atggaagccg gtcttgtcga tcaggatgat     480
ctggacgaag agcatcaggg gctcgcgcca gccgaactgt tcgccaggct caaggcgcgc     540
atgcccgacg gcgatgatct cgtcgtgacc catggcgatg cctgcttgcc gaatatcatg     600
gtggaaaatg gccgcttttc tggattcatc gactgtggcc ggctgggtgt ggcggaccgc     660
tatcaggaca tagcgttggc tacccgtgat attgctgaag agcttggcgg cgaatgggct     720
gaccgcttcc tcgtgcttta cggtatcgcc gctcccgatt cgcagcgcat cgccttctat     780
cgccttcttg acgagttctt ctga                                            804

<210> SEQ ID NO 20
<211> LENGTH: 267
<212> TYPE: PRT
<213> ORGANISM: Escherichia coli
<220> FEATURE:
<223> OTHER INFORMATION: Neomycin resistance gene

<400> SEQUENCE: 20

Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Met Ala Asp Ala Met Arg Arg Leu His Thr
        115                 120                 125

Leu Asp Pro Ala Thr Cys Pro Phe Asp His Gln Ala Lys His Arg Ile
    130                 135                 140

Glu Arg Ala Arg Thr Arg Met Glu Ala Gly Leu Val Asp Gln Asp Asp
145                 150                 155                 160

Leu Asp Glu Glu His Gln Gly Leu Ala Pro Ala Glu Leu Phe Ala Arg
                165                 170                 175

Leu Lys Ala Arg Met Pro Asp Gly Asp Asp Leu Val Val Thr His Gly
            180                 185                 190

Asp Ala Cys Leu Pro Asn Ile Met Val Glu Asn Gly Arg Phe Ser Gly
        195                 200                 205

Phe Ile Asp Cys Gly Arg Leu Gly Val Ala Asp Arg Tyr Gln Asp Ile
```

```
        210                 215                 220
Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
                260                 265

<210> SEQ ID NO 21
<211> LENGTH: 720
<212> TYPE: DNA
<213> ORGANISM: Aequorea victoria
<220> FEATURE:
<223> OTHER INFORMATION: Green fluorescent protein

<400> SEQUENCE: 21
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga cccctgaagtt catctgcacc accggcaagc tgcccgtgcc ctggcccacc    180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 22
<211> LENGTH: 239
<212> TYPE: PRT
<213> ORGANISM: Aequorea victoria
<220> FEATURE:
<223> OTHER INFORMATION: Green fluorescent protein

<400> SEQUENCE: 22

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
```

```
                130                 135                 140
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
                210                 215                 220

Val Thr Ala Ala Gly Ile Thr Leu Gly Met Asp Glu Leu Tyr Lys
225                 230                 235

<210> SEQ ID NO 23
<211> LENGTH: 720
<212> TYPE: DNA
<213> ORGANISM: Aequorea victoria
<220> FEATURE:
<223> OTHER INFORMATION: Yellow fluorescent protein

<400> SEQUENCE: 23
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaagtag   720

<210> SEQ ID NO 24
<211> LENGTH: 239
<212> TYPE: PRT
<213> ORGANISM: Aequorea victoria
<220> FEATURE:
<223> OTHER INFORMATION: Yellow fluorescent protein

<400> SEQUENCE: 24

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
                35                  40                  45

Cys Thr Thr Gly Lys Leu Pro Val Pro Trp Pro Thr Leu Val Thr Thr
                50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
```

```
                        85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
        130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Tyr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys
225                 230                 235

<210> SEQ ID NO 25
<211> LENGTH: 948
<212> TYPE: DNA
<213> ORGANISM: Homo sapiens
<220> FEATURE:
<223> OTHER INFORMATION: Truncated NGFR

<400> SEQUENCE: 25 atggggggcag gtgccaccgg ccgcgccatg gacgggccgc gcctgctgct gttgctgctt    60
ctgggggtgt cccttggagg tgccaaggag gcatgcccca caggcctgta cacacatggc   120
ggcgagtgct gcaaagcctg caacctgggc gaaggtgtgg cccagccttg tggagccaac   180
cagaccgtgt gtgagccctg cctggacagt gtgacgttct ccgacgtggt gagcgcgacg   240
gagccgtgca agccgtgcac tgagtgcgtg gggcttcaga gcatgtcggc gccgtgcgtg   300
gaggccgacg acgccgtgtg ccgctgtgcc tacggctact accaggacga gacgaccggg   360
cgctgcgagg cgtgccgcgt gtgcgaggcg ggctcgggcc tcgtattctc gtgccaggac   420
aagcagaaca ccgtgtgcga ggagtgcccc gacggcacgt attcagatga ggccaaccat   480
gtggacccgt gcctgccctg caccgtgtgc gaggacaccg agcgccagct gcgcgagtgc   540
acacgctggg ccgacgccga gtgcgaggag atccctggcc gttggattac aaggtccaca   600
ccccccgaag ctctgacag cacagccacc agcacccagg agcctgaggc acctccagaa   660
caagacctca tagccagcac ggtggcagat gtggtgacca cagtgatggg cagctcccag   720
cccgtggtaa cccgaggcac caccgacaac ctcatccccg tctattgctc catcctggct   780
gctgtggtgg tgggccttgt ggcctacata gccttcaaga ggtggaacag ctgcaagcag   840
aacaagcaag gagccaacag ccggccagtg aaccagacgc cccaccagag gggagaaaaa   900
ctccatagtg acagtggcat ctccgtggac agccagagcc tgcaatag              948

<210> SEQ ID NO 26
<211> LENGTH: 315
<212> TYPE: PRT
<213> ORGANISM: Homo sapiens
<220> FEATURE:
<223> OTHER INFORMATION: Truncated NGFR

<400> SEQUENCE: 26
```

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Gly Gly Glu Cys Cys Lys Ala Cys Asn
        35                  40                  45

Leu Gly Glu Gly Val Ala Gln Pro Cys Gly Ala Asn Gln Thr Val Cys
50                  55                  60

Glu Pro Cys Leu Asp Ser Val Thr Phe Ser Asp Val Val Ser Ala Thr
65              70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Thr Ser Thr Gln Glu Pro Glu Ala Pro Pro Glu Gln Asp Leu Ile
210                 215                 220

Ala Ser Thr Val Ala Asp Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Pro Glu Gly Glu Lys Leu His Ser Asp
290                 295                 300

Ser Gly Ile Ser Val Asp Ser Gln Ser Leu Gln
305                 310                 315

<210> SEQ ID NO 27
<211> LENGTH: 627
<212> TYPE: DNA
<213> ORGANISM: Homo sapiens
<220> FEATURE:
<223> OTHER INFORMATION: Truncated CD7

<400> SEQUENCE: 27
atggccgggc ctccgaggct cctgctgctg cccctgcttc tggcgctggc tcgcggcctg    60
cctggggccc tggctgccca agaggtgcag cagtctcccc actgcacgac tgtcccgtg   120 ggagcctccg tcaacatcac ctgctccacc agcgggggcc tgcgtgggat ctacctgagg   180
cagctcgggc acagcccca agacatcatt tactacgagg acgggtggt gcccactacg   240 gacagacggt tccggggccg catcgacttc tcagggtccc aggacaacct gactatcacc   300
```

```
atgcaccgcc tgcagctgtc ggacactggc acctacacct gccaggccat cacggaggtc    360
aatgtctacg gctccggcac cctggtcctg gtgacagagg aacagtccca aggatggcac    420
agatgctcgg acgccccacc aagggcctct gccctcctg ccccaccgac aggctccgcc     480
ctccctgacc cgcagacagc ctctgccctc cctgaccgc cagcagcctc tgccctccct     540
gcggccctgg cggtgatctc cttcctcctc gggctgggcc tgggggtggc gtgtgtgctg    600
gcgaggacac agataaagaa actgtga                                         627
```

<210> SEQ ID NO 28
<211> LENGTH: 208
<212> TYPE: PRT
<213> ORGANISM: Homo sapiens
<220> FEATURE:
<223> OTHER INFORMATION: Truncated CD7

<400> SEQUENCE: 28

```
Met Ala Gly Pro Pro Arg Leu Leu Leu Pro Leu Leu Leu Ala Leu
 1               5                  10                  15

Ala Arg Gly Leu Pro Gly Ala Leu Ala Ala Gln Glu Val Gln Gln Ser
            20                  25                  30

Pro His Cys Thr Thr Val Pro Val Gly Ala Ser Val Asn Ile Thr Cys
        35                  40                  45

Ser Thr Ser Gly Gly Leu Arg Gly Ile Tyr Leu Arg Gln Leu Gly Pro
    50                  55                  60

Gln Pro Gln Asp Ile Ile Tyr Tyr Glu Asp Gly Val Val Pro Thr Thr
65                  70                  75                  80

Asp Arg Arg Phe Arg Gly Arg Ile Asp Phe Ser Gly Ser Gln Asp Asn
                85                  90                  95

Leu Thr Ile Thr Met His Arg Leu Gln Leu Ser Asp Thr Gly Thr Tyr
            100                 105                 110

Thr Cys Gln Ala Ile Thr Glu Val Asn Val Tyr Gly Ser Gly Thr Leu
        115                 120                 125

Val Leu Val Thr Glu Glu Gln Ser Gln Gly Trp His Arg Cys Ser Asp
    130                 135                 140

Ala Pro Pro Arg Ala Ser Ala Leu Pro Ala Pro Pro Thr Gly Ser Ala
145                 150                 155                 160

Leu Pro Asp Pro Gln Thr Ala Ser Ala Leu Pro Asp Pro Pro Ala Ala
                165                 170                 175

Ser Ala Leu Pro Ala Ala Leu Ala Val Ile Ser Phe Leu Leu Gly Leu
            180                 185                 190

Gly Leu Gly Val Ala Cys Val Leu Ala Arg Thr Gln Ile Lys Lys Leu
        195                 200                 205
```

<210> SEQ ID NO 29
<211> LENGTH: 38
<212> TYPE: DNA
<213> ORGANISM: Artificial Sequence
<220> FEATURE:
<223> OTHER INFORMATION: Forward Primer eMLV-R

<400> SEQUENCE: 29

```
tttaagcggc cgcatgggct gcaaaaacct gctcggtc                              38
```

<210> SEQ ID NO 30
<211> LENGTH: 38
<212> TYPE: DNA
<213> ORGANISM: Artificial Sequence
<220> FEATURE:

<223> OTHER INFORMATION: Reverse Primer eMLV-R

<400> SEQUENCE: 30
tttaaggatc ctcatttgca ctggtccaag ttgctgtc                38

<210> SEQ ID NO 31
<211> LENGTH: 1869
<212> TYPE: DNA
<213> ORGANISM: Mus musculus
<220> FEATURE:
<223> OTHER INFORMATION: Rec1 receptor nucleic acid

<400> SEQUENCE: 31

| | | | | | |
|---|---|---|---|---|---|
| atgggctgca | aaaacctgct | cggtctgggc | cagcagatgc | tgcgccggaa | ggtggtggac | 60 |
| tgcagccggg | aggagagccg | gctgtcccgc | tgcctcaaca | cctatgacct | ggtagctctt | 120 |
| ggggtgggca | gcaccttggg | cgctggtgtc | tatgtcctag | ccggtgccgt | ggcccgtgaa | 180 |
| aatgctggcc | ctgccatcgt | catctccttc | ttgattgctg | ctctcgcctc | cgtgctggcc | 240 |
| ggcctgtgct | acggcgagtt | tggtgcccgt | gtccccaaga | cgggctcagc | ctacctctac | 300 |
| agctacgtga | cggtggggga | gctttgggcc | ttcatcactg | gctggaacct | gattctctcc | 360 |
| tacatcatcg | gtacttcaag | cgtggcaaga | gcctggagtg | cgacttttga | cgagctgata | 420 |
| ggcaagccca | tcggagagtt | ctcacgtcag | cacatggccc | tgaatgctcc | tggggtgctg | 480 |
| gcccaaaccc | cggacatatt | tgctgtgatt | ataattatca | tcttaacagg | actgttaact | 540 |
| cttggcgtga | aggagtcagc | catggtcaac | aaaattttca | cctgtatcaa | tgtcctggtc | 600 |
| ttgtgcttca | tcgtggtgtc | cgggttcgtg | aaaggctcca | ttaaaaactg | gcagctcacg | 660 |
| gagaaaaatt | tctcctgtaa | caacaacgac | acaaacgtga | atacggtga | gggagggttt | 720 |
| atgccctttg | gattctctgg | tgtcctgtca | ggggcagcga | cctgctttta | tgccttcgtg | 780 |
| ggctttgact | gcatcgccac | cacagggaa | gaagtcaaga | ccccagaa | ggccattcct | 840 |
| gtgggcatcg | tggcgtccct | cctcatttgc | ttcatagcgt | actttggcgt | gtccgccgct | 900 |
| ctcacgctca | tgatgcctta | cttctgcctg | gacatcgaca | gcccgctgcc | tggtgccttc | 960 |
| aagcaccagg | gctgggaaga | agctaagtac | gcagtggcca | ttggctctct | ctgcgcactt | 1020 |
| tccaccagtc | tcctaggctc | catgtttccc | atgccccgag | ttatctatgc | catggctgaa | 1080 |
| gatggactac | tgtttaaatt | tttggccaaa | atcaacaata | ggaccaaaac | acccgtaatc | 1140 |
| gccactgtga | cctcaggcgc | cattgctgct | gtgatggcct | tcctctttga | actgaaggac | 1200 |
| ctggtggacc | tcatgtccat | ggcactctc | ctggcttact | cttgtggc | tgcctgtgtt | 1260 |
| ttggtcttac | ggtaccagcc | agaacaacct | aatctggtat | accagatggc | cagaaccacc | 1320 |
| gaggagctag | atcgagtaga | tcagaatgag | ctggtcagtg | ccagtgaatc | acagacaggc | 1380 |
| tttttaccgg | tagccgagaa | gttttctctg | aaatccatcc | tctcacccaa | gaacgtggag | 1440 |
| ccctccaaat | tctcagggct | aattgtgaac | atttcagccg | gcctcctagc | cgctcttatc | 1500 |
| atcaccgtgt | gcattgtggc | cgtgcttgga | agagaggccc | tggccgaagg | gacactgtgg | 1560 |
| gcagtctttg | taatgacagg | gtcagtcctc | tctgcatgc | tggtgacagg | catcatctgg | 1620 |
| agacagcctg | agagcaagac | caagctctca | tttaaggtac | cctttgtccc | cgtacttcct | 1680 |
| gtcttgagca | tcttcgtgaa | catctatctc | atgatgcagc | tggaccaggg | cacgtgggtc | 1740 |
| cggtttgcag | tgtggatgct | gataggtttc | accatctatt | tcggttatgg | gatctggcac | 1800 |
| agtgaggaag | cgtccctggc | tgctggccag | gcaaagactc | ctgacagcaa | cttggaccag | 1860 |
| tgcaaatga | | | | | | 1869 |

-continued

<210> SEQ ID NO 32
<211> LENGTH: 622
<212> TYPE: PRT
<213> ORGANISM: Mus musculus
<220> FEATURE:
<223> OTHER INFORMATION: Rec1 receptor amino acid

<400> SEQUENCE: 32

```
Met Gly Cys Lys Asn Leu Leu Gly Leu Gly Gln Gln Met Leu Arg Arg
1               5                   10                  15

Lys Val Val Asp Cys Ser Arg Glu Glu Ser Arg Leu Ser Arg Cys Leu
            20                  25                  30

Asn Thr Tyr Asp Leu Val Ala Leu Gly Val Gly Ser Thr Leu Gly Ala
        35                  40                  45

Gly Val Tyr Val Leu Ala Gly Ala Val Ala Arg Glu Asn Ala Gly Pro
    50                  55                  60

Ala Ile Val Ile Ser Phe Leu Ile Ala Ala Leu Ala Ser Val Leu Ala
65                  70                  75                  80

Gly Leu Cys Tyr Gly Glu Phe Gly Ala Arg Val Pro Lys Thr Gly Ser
                85                  90                  95

Ala Tyr Leu Tyr Ser Tyr Val Thr Val Gly Glu Leu Trp Ala Phe Ile
            100                 105                 110

Thr Gly Trp Asn Leu Ile Leu Ser Tyr Ile Ile Gly Thr Ser Ser Val
        115                 120                 125

Ala Arg Ala Trp Ser Ala Thr Phe Asp Glu Leu Ile Gly Lys Pro Ile
    130                 135                 140

Gly Glu Phe Ser Arg Gln His Met Ala Leu Asn Ala Pro Gly Val Leu
145                 150                 155                 160

Ala Gln Thr Pro Asp Ile Phe Ala Val Ile Ile Ile Ile Leu Thr
                165                 170                 175

Gly Leu Leu Thr Leu Gly Val Lys Glu Ser Ala Met Val Asn Lys Ile
            180                 185                 190

Phe Thr Cys Ile Asn Val Leu Val Leu Cys Phe Ile Val Val Ser Gly
        195                 200                 205

Phe Val Lys Gly Ser Ile Lys Asn Trp Gln Leu Thr Glu Lys Asn Phe
    210                 215                 220

Ser Cys Asn Asn Asn Asp Thr Asn Val Lys Tyr Gly Glu Gly Gly Phe
225                 230                 235                 240

Met Pro Phe Gly Phe Ser Gly Val Leu Ser Gly Ala Ala Thr Cys Phe
                245                 250                 255

Tyr Ala Phe Val Gly Phe Asp Cys Ile Ala Thr Thr Gly Glu Glu Val
            260                 265                 270

Lys Asn Pro Gln Lys Ala Ile Pro Val Gly Ile Val Ala Ser Leu Leu
        275                 280                 285

Ile Cys Phe Ile Ala Tyr Phe Gly Val Ser Ala Ala Leu Thr Leu Met
    290                 295                 300

Met Pro Tyr Phe Cys Leu Asp Ile Asp Ser Pro Leu Pro Gly Ala Phe
305                 310                 315                 320

Lys His Gln Gly Trp Glu Glu Ala Lys Tyr Ala Val Ala Ile Gly Ser
                325                 330                 335

Leu Cys Ala Leu Ser Thr Ser Leu Leu Gly Ser Met Phe Pro Met Pro
            340                 345                 350

Arg Val Ile Tyr Ala Met Ala Glu Asp Gly Leu Leu Phe Lys Phe Leu
        355                 360                 365

Ala Lys Ile Asn Asn Arg Thr Lys Thr Pro Val Ile Ala Thr Val Thr
```

```
                370           375           380
Ser Gly Ala Ile Ala Ala Val Met Ala Phe Leu Phe Glu Leu Lys Asp
385                 390                 395                 400

Leu Val Asp Leu Met Ser Ile Gly Thr Leu Leu Ala Tyr Ser Leu Val
            405                 410                 415

Ala Ala Cys Val Leu Val Leu Arg Tyr Gln Pro Glu Gln Pro Asn Leu
        420                 425                 430

Val Tyr Gln Met Ala Arg Thr Thr Glu Glu Leu Asp Arg Val Asp Gln
    435                 440                 445

Asn Glu Leu Val Ser Ala Ser Glu Ser Gln Thr Gly Phe Leu Pro Val
450                 455                 460

Ala Glu Lys Phe Ser Leu Lys Ser Ile Leu Ser Pro Lys Asn Val Glu
465                 470                 475                 480

Pro Ser Lys Phe Ser Gly Leu Ile Val Asn Ile Ser Ala Gly Leu Leu
            485                 490                 495

Ala Ala Leu Ile Ile Thr Val Cys Ile Val Ala Val Leu Gly Arg Glu
            500                 505                 510

Ala Leu Ala Glu Gly Thr Leu Trp Ala Val Phe Val Met Thr Gly Ser
        515                 520                 525

Val Leu Leu Cys Met Leu Val Thr Gly Ile Ile Trp Arg Gln Pro Glu
530                 535                 540

Ser Lys Thr Lys Leu Ser Phe Lys Val Pro Phe Val Pro Val Leu Pro
545                 550                 555                 560

Val Leu Ser Ile Phe Val Asn Ile Tyr Leu Met Met Gln Leu Asp Gln
                565                 570                 575

Gly Thr Trp Val Arg Phe Ala Val Trp Met Leu Ile Gly Phe Thr Ile
            580                 585                 590

Tyr Phe Gly Tyr Gly Ile Trp His Ser Glu Glu Ala Ser Leu Ala Ala
        595                 600                 605

Gly Gln Ala Lys Thr Pro Asp Ser Asn Leu Asp Gln Cys Lys
    610                 615                 620

<210> SEQ ID NO 33
<211> LENGTH: 10
<212> TYPE: DNA
<213> ORGANISM: Artificial Sequence
<220> FEATURE:
<223> OTHER INFORMATION: Stuffer sequence

<400> SEQUENCE: 33
ttaattaatt                                                          10

<210> SEQ ID NO 34
<211> LENGTH: 51
<212> TYPE: DNA
<213> ORGANISM: Artificial Sequence
<220> FEATURE:
<223> OTHER INFORMATION: Forward Primer Kozak Gag/Pol

<400> SEQUENCE: 34
aataagcggc cgcgccgcca ccatgggcca gactgttacc actcccttaa g           51

<210> SEQ ID NO 35
<211> LENGTH: 31
<212> TYPE: DNA
<213> ORGANISM: Artificial Sequence
<220> FEATURE:
<223> OTHER INFORMATION: Reverse Primer MLVgp RI

<400> SEQUENCE: 35
```

```
atgaattctt aggggccctc gcgggttaac c                                    31

<210> SEQ ID NO 36
<211> LENGTH: 5217
<212> TYPE: DNA
<213> ORGANISM: Murine leukemia virus
<220> FEATURE:
<223> OTHER INFORMATION: MLV gag/pol nucleic acid

<400> SEQUENCE: 36
atgggccaga ctgttaccac tcccttaagt ttgaccttag gtcactggaa agatgtcgag    60
cggatcgctc acaaccagtc ggtagatgtc aagaagagac gttgggttac cttctgctct   120
gcagaatggc caacctttaa cgtcggatgg ccgcgagacg caccttttaa ccgagacctc   180
atcacccagg ttaagatcaa ggtctttttca cctggcccgc atggacaccc agaccaggtc   240
ccctacatcg tgacctggga agccttggct tttgaccccc ctccctgggt caagcccttt   300
gtacacccta agcctccgcc tcctcttcct ccatccgccc cgtctctccc ccttgaacct   360
cctcgttcga ccccgcctcg atcctccctt tatccagccc tcactccttc tctaggcgcc   420
aaacctaaac ctcaagttct ttctgacagt ggggggccgc tcatcgacct acttacagaa   480
gaccccccgc ttatagggga cccaagacca ccccccttccg acaggggacgg aaatggtgga   540 gaagcgaccc ctgcgggaga ggcaccggac ccctccccaa tggcatctcg cctacgtggg   600
agacgggagc cccctgtggc cgactccact acctcgcagg cattcccccct ccgcgcagga   660 ggaaacggac agcttcaata ctggccgttc tcctcttctg acctttacaa ctggaaaaat   720 aataacccctt cttttttctga agatccaggt aaactgacag ctctgatcga gtctgttctc   780
atcacccatc agcccacctg ggacgactgt cagcagctgt ggggactct gctgaccgga   840 gaagaaaaac aacgggtgct cttagaggct agaaaggcgg tgcggggcga tgatgggcgc   900
cccactcaac tgcccaatga agtcgatgcc gcttttcccc tcgagcgccc agactggat     960 tacaccaccc aggcaggtag gaaccaccta gtccactatc gccagttgct cctagcgggt  1020
ctccaaaacg cgggcagaag ccccaccaat ttggccaagg taaaaggaat aacacaaggg  1080
cccaatgagt ctccctcggc cttcctagag agacttaagg aagcctatcg caggtacact  1140
ccttatgacc ctgaggaccc agggcaagaa actaatgtgt ctatgtctttt catttggcag  1200 tctgccccag acattgggag aaagttagag aggttagaag atttaaaaaaa caagacgctt  1260 ggagatttgg ttagagaggc agaaaagatc tttaataaac gagaaacccc ggaagaaaga  1320
gaggaacgta tcaggagaga aacagaggaa aagaagaac gccgtaggac agaggatgag  1380
cagaaagaga agaaagaga tcgtaggaga catagagaga tgagcaagct attggccact  1440
gtcgttagtg gacagaaaca ggatagacag ggaggagaac gaaggaggtc ccaactcgat  1500
cgcgaccagt gtgcctactg caaagaaaag gggcactggg ctaaagattg tcccaagaaa  1560
ccacgaggac ctcggggacc aagaccccag acctccctcc tgaccctaga tgactaggga  1620
ggtcagggtc aggagccccc ccctgaaccc aggataaccc tcaaagtcgg ggggcaaccc  1680
gtcaccttcc tggtagatac tggggcccaa cactccgtgc tgacccaaaa tcctggaccc  1740
ctaagtgata agtctgcctg gtccaaggg gctactggag aaagcggta tcgctggacc  1800 acggatcgca aagtacatct agctaccggt aaggtcaccc actctttcct ccatgtacca  1860
gactgtccct atcctctgtt aggaagagat ttgctgacta aactaaaagc ccaaatccac  1920
tttgagggat caggagctca ggttatggga ccaatgggc agcccctgca agtgttgacc  1980
ctaaatatag aagatgagca tcggctacat gagacctcaa aagagccaga tgtttctcta  2040
```

```
gggtccacat ggctgtctga ttttcctcag gcctgggcgg aaaccggggg catgggactg    2100
gcagttcgcc aagctcctct gatcatacct ctgaaagcaa cctctacccc cgtgtccata    2160
aaacaatacc ccatgtcaca agaagccaga ctggggatca agccccacat acagagactg    2220
ttggaccagg gaatactggt accctgccag tcccctggac acacgcccct gctacccgtt    2280
aagaaaccag ggactaatga ttataggcct gtccaggatc tgagagaagt caacaagcgg    2340
gtggaagaca tccaccccac cgtgcccaac ccttacaacc tcttgagcgg gctcccaccg    2400
tcccaccagt ggtacactgt gcttgattta aggatgcctt ttttctgcct gagactccac    2460
cccaccagtc agcctctctt cgcctttgag tggagagatc agagatggga atctcagga    2520 caattgacct ggaccagact cccacagggt ttcaaaaaca gtcccaccct gtttgatgag    2580
gcactgcaca gagacctagc agacttccgg atccagcacc cagacttgat cctgctacag    2640
tacgtggatg acttactgct ggccgccact tctgagctag actgccaaca aggtactcgg    2700
gccctgttac aaaccctagg gaacctcggg tatcgggcct cggccaagaa agcccaaatt    2760
tgccagaaac aggtcaagta tctggggtat cttctaaaag agggtcagag atggctgact    2820
gaggccagaa aagagactgt gatggggcag cctactccga agacccctcg acaactaagg    2880
gagttcctag ggacggcagg cttctgtcgc ctctggatcc ctgggtttgc agaaatggca    2940 gccccttgt accctctcac caaaacgggg actctgttta attggggccc agaccaacaa    3000
aaggcctatc aagaaatcaa gcaagctctt ctaactgccc cagccctggg gttgccagat    3060
ttgactaagc cctttgaact ctttgtcgac gagaagcagg gctacgccaa aggtgtccta    3120
acgcaaaaac tgggaccttg gcgtcggccg gtggcctacc tgtccaaaaa gctagaccca    3180
gtagcagctg ggtggccccc ttgcctacgg atggtagcag ccattgccgt actgacaaag    3240
gatgcaggca agctaaccat gggacagcca ctagtcattc tggccccca tgcagtagag    3300 gcactagtca acaaccccc cgaccgctgg ctttccaacg cccggatgac tcactatcag    3360
gccttgcttt tggacacgga ccgggtccag ttcggaccgg tggtagccct gaacccggct    3420
acgctgctcc cactgcctga ggaagggctg caacacaact gccttgatat cctggccgaa    3480
gcccacggaa cccgacccga cctaacggac cagccgctcc cagacgccga ccacacctgg    3540
tacacggatg gaagcagtct cttacaagag ggacagcgta aggcgggagc tgcggtgacc    3600
accgagaccg aggtaatctg ggctaaagcc ctgccagccg ggacatccgc tcagcgggct    3660
gaactgatag cactcacccca ggccctaaag atggcagaag gtaagaagct aaatgtttat    3720
actgatagcc gttatgcttt tgctactgcc catatccatg gagaaatata cagaaggcgt    3780
gggttgctca catcagaagg caaagagatc aaaaataaag acgagatctt ggccctacta    3840
aaagccctct ttctgcccaa aagacttagc ataatccatt gtccaggaca tcaaaaggga    3900
cacagcgccg aggctagagg caaccggatg gctgaccaag cggcccgaaa ggcagccatc    3960
acagagactc cagacacctc taccctcctc atagaaaatt catcaccta cacctcagaa    4020 cattttcatt acacagtgac tgatataaag gacctaacca agttggggc catttatgat    4080 aaaacaaaga agtattgggt ctaccaagga aaacctgtga tgcctgacca gtttactttt    4140
gaattattag actttcttca tcagctgact cacctcagct tctcaaaaat gaaggctctc    4200 ctagagaaa gccacagtcc ctactacatg ctgaaccggg atcgaacact caaaaatatc    4260
actgagacct gcaaagcttg tgcacaagtc aacgccagca agtctgccgt taaacaggga    4320
actagggtcc gcgggcatcg gcccggcact cattgggaga tcgatttcac cgagataaag    4380
cccggattgt atggctataa atatcttcta gttttatag ataccttttc tggctggata    4440
```

-continued

```
gaagccttcc caaccaagaa agaaaccgcc aaggtcgtaa ccaagaagct actagaggag    4500
atcttcccca ggttcggcat gcctcaggta ttgggaactg acaatgggcc tgccttcgtc    4560
tccaaggtga gtcagacagt ggccgatctg ttggggattg attggaaatt acattgtgca    4620
tacagacccc aaagctcagg ccaggtagaa agaatgaata gaaccatcaa ggagacttta    4680
actaaattaa cgcttgcaac tggctctaga gactgggtgc tcctactccc cttagccctg    4740
taccgagccc gcaacacgcc gggcccccat ggcctcaccc catatgagat cttatatggg    4800
gcacccccgc cccttgtaaa cttccctgac cctgacatga caagagttac taacagcccc    4860
tctctccaag ctcacttaca ggctctctac ttagtccagc acgaagtctg agacctctg    4920 gcggcagcct accaagaaca actggaccga ccggtggtac ctcaccctta ccgagtcggc    4980
gacacagtgt gggtccgccg acaccagact aagaacctag aacctcgctg aaaggacct    5040 tacacagtcc tgctgaccac ccccaccgcc ctcaaagtag acggcatcgc agcttggata    5100
cacgccgccc acgtgaaggc tgccgacccc gggggtggac catcctctag actgacatgg    5160
cgcgttcaac gctctcaaaa ccccttaaaa ataaggttaa cccgcgaggc cccctaa      5217
```

<210> SEQ ID NO 37
<211> LENGTH: 1737
<212> TYPE: PRT
<213> ORGANISM: Murine leukemia virus
<220> FEATURE:
<223> OTHER INFORMATION: MLV gag/pol amino acid

<400> SEQUENCE: 37

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
```

-continued

```
               225                 230                 235                 240
Asn Asn Pro Ser Phe Ser Glu Asp Pro Gly Lys Leu Thr Ala Leu Ile
                245                 250                 255
Glu Ser Val Leu Ile Thr His Gln Pro Thr Trp Asp Asp Cys Gln Gln
                260                 265                 270
Leu Leu Gly Thr Leu Thr Gly Glu Glu Lys Gln Arg Val Leu Leu
            275                 280                 285
Glu Ala Arg Lys Ala Val Arg Gly Asp Asp Gly Arg Pro Thr Gln Leu
        290                 295                 300
Pro Asn Glu Val Asp Ala Ala Phe Pro Leu Glu Arg Pro Asp Trp Asp
305                 310                 315                 320
Tyr Thr Thr Gln Ala Gly Arg Asn His Leu Val His Tyr Arg Gln Leu
                325                 330                 335
Leu Leu Ala Gly Leu Gln Asn Ala Gly Arg Ser Pro Thr Asn Leu Ala
            340                 345                 350
Lys Val Lys Gly Ile Thr Gln Gly Pro Asn Glu Ser Pro Ser Ala Phe
        355                 360                 365
Leu Glu Arg Leu Lys Glu Ala Tyr Arg Arg Tyr Thr Pro Tyr Asp Pro
    370                 375                 380
Glu Asp Pro Gly Gln Glu Thr Asn Val Ser Met Ser Phe Ile Trp Gln
385                 390                 395                 400
Ser Ala Pro Asp Ile Gly Arg Lys Leu Glu Arg Leu Glu Asp Leu Lys
                405                 410                 415
Asn Lys Thr Leu Gly Asp Leu Val Arg Glu Ala Glu Lys Ile Phe Asn
            420                 425                 430
Lys Arg Glu Thr Pro Glu Glu Arg Glu Arg Ile Arg Arg Glu Thr
        435                 440                 445
Glu Glu Lys Glu Glu Arg Arg Thr Glu Asp Glu Gln Lys Glu Lys
    450                 455                 460
Glu Arg Asp Arg Arg His Arg Glu Met Ser Lys Leu Leu Ala Thr
465                 470                 475                 480
Val Val Ser Gly Gln Lys Gln Asp Arg Gln Gly Gly Glu Arg Arg
                485                 490                 495
Ser Gln Leu Asp Arg Asp Gln Cys Ala Tyr Cys Lys Glu Lys Gly His
            500                 505                 510
Trp Ala Lys Asp Cys Pro Lys Lys Pro Arg Gly Pro Arg Gly Pro Arg
        515                 520                 525
Pro Gln Thr Ser Leu Leu Thr Leu Asp Asp Gly Gly Gln Gly Gln Glu
    530                 535                 540
Pro Pro Pro Glu Pro Arg Ile Thr Leu Lys Val Gly Gly Gln Pro Val
545                 550                 555                 560
Thr Phe Leu Val Asp Thr Gly Ala Gln His Ser Val Leu Thr Gln Asn
                565                 570                 575
Pro Gly Pro Leu Ser Asp Lys Ser Ala Trp Val Gln Gly Ala Thr Gly
            580                 585                 590
Gly Lys Arg Tyr Arg Trp Thr Thr Asp Arg Lys Val His Leu Ala Thr
        595                 600                 605
Gly Lys Val Thr His Ser Phe Leu His Val Pro Asp Cys Pro Tyr Pro
    610                 615                 620
Leu Leu Gly Arg Asp Leu Leu Thr Lys Leu Lys Ala Gln Ile His Phe
625                 630                 635                 640
Glu Gly Ser Gly Ala Gln Val Met Gly Pro Met Gly Gln Pro Leu Gln
                645                 650                 655
```

```
Val Leu Thr Leu Asn Ile Glu Asp Glu His Arg Leu His Glu Thr Ser
            660                 665                 670

Lys Glu Pro Asp Val Ser Leu Gly Ser Thr Trp Leu Ser Asp Phe Pro
        675                 680                 685

Gln Ala Trp Ala Glu Thr Gly Gly Met Gly Leu Ala Val Arg Gln Ala
    690                 695                 700

Pro Leu Ile Ile Pro Leu Lys Ala Thr Ser Thr Pro Val Ser Ile Lys
705                 710                 715                 720

Gln Tyr Pro Met Ser Gln Glu Ala Arg Leu Gly Ile Lys Pro His Ile
                725                 730                 735

Gln Arg Leu Leu Asp Gln Gly Ile Leu Val Pro Cys Gln Ser Pro Trp
            740                 745                 750

Asn Thr Pro Leu Leu Pro Val Lys Lys Pro Gly Thr Asn Asp Tyr Arg
        755                 760                 765

Pro Val Gln Asp Leu Arg Glu Val Asn Lys Arg Val Glu Asp Ile His
    770                 775                 780

Pro Thr Val Pro Asn Pro Tyr Asn Leu Leu Ser Gly Leu Pro Pro Ser
785                 790                 795                 800

His Gln Trp Tyr Thr Val Leu Asp Leu Lys Asp Ala Phe Phe Cys Leu
                805                 810                 815

Arg Leu His Pro Thr Ser Gln Pro Leu Phe Ala Phe Glu Trp Arg Asp
            820                 825                 830

Pro Glu Met Gly Ile Ser Gly Gln Leu Thr Trp Thr Arg Leu Pro Gln
        835                 840                 845

Gly Phe Lys Asn Ser Pro Thr Leu Phe Asp Glu Ala Leu His Arg Asp
    850                 855                 860

Leu Ala Asp Phe Arg Ile Gln His Pro Asp Leu Ile Leu Leu Gln Tyr
865                 870                 875                 880

Val Asp Asp Leu Leu Leu Ala Ala Thr Ser Glu Leu Asp Cys Gln Gln
                885                 890                 895

Gly Thr Arg Ala Leu Leu Gln Thr Leu Gly Asn Leu Gly Tyr Arg Ala
            900                 905                 910

Ser Ala Lys Lys Ala Gln Ile Cys Gln Lys Gln Val Lys Tyr Leu Gly
        915                 920                 925

Tyr Leu Leu Lys Glu Gly Gln Arg Trp Leu Thr Glu Ala Arg Lys Glu
    930                 935                 940

Thr Val Met Gly Gln Pro Thr Pro Lys Thr Pro Arg Gln Leu Arg Glu
945                 950                 955                 960

Phe Leu Gly Thr Ala Gly Phe Cys Arg Leu Trp Ile Pro Gly Phe Ala
                965                 970                 975

Glu Met Ala Ala Pro Leu Tyr Pro Leu Thr Lys Thr Gly Thr Leu Phe
            980                 985                 990

Asn Trp Gly Pro Asp Gln Gln Lys Ala Tyr Gln Glu Ile Lys Gln Ala
        995                 1000                1005

Leu Leu Thr Ala Pro Ala Leu Gly Leu Pro Asp Leu Thr Lys Pro
    1010                1015                1020

Phe Glu Leu Phe Val Asp Glu Lys Gln Gly Tyr Ala Lys Gly Val
    1025                1030                1035

Leu Thr Gln Lys Leu Gly Pro Trp Arg Arg Pro Val Ala Tyr Leu
    1040                1045                1050

Ser Lys Lys Leu Asp Pro Val Ala Ala Gly Trp Pro Pro Cys Leu
    1055                1060                1065

Arg Met Val Ala Ala Ile Ala Val Leu Thr Lys Asp Ala Gly Lys
    1070                1075                1080
```

```
Leu Thr Met Gly Gln Pro Leu Val Ile Leu Ala Pro His Ala Val
1085                1090                1095

Glu Ala Leu Val Lys Gln Pro Pro Asp Arg Trp Leu Ser Asn Ala
1100                1105                1110

Arg Met Thr His Tyr Gln Ala Leu Leu Leu Asp Thr Asp Arg Val
1115                1120                1125

Gln Phe Gly Pro Val Val Ala Leu Asn Pro Ala Thr Leu Leu Pro
1130                1135                1140

Leu Pro Glu Glu Gly Leu Gln His Asn Cys Leu Asp Ile Leu Ala
1145                1150                1155

Glu Ala His Gly Thr Arg Pro Asp Leu Thr Asp Gln Pro Leu Pro
1160                1165                1170

Asp Ala Asp His Thr Trp Tyr Thr Asp Gly Ser Ser Leu Leu Gln
1175                1180                1185

Glu Gly Gln Arg Lys Ala Gly Ala Ala Val Thr Thr Glu Thr Glu
1190                1195                1200

Val Ile Trp Ala Lys Ala Leu Pro Ala Gly Thr Ser Ala Gln Arg
1205                1210                1215

Ala Glu Leu Ile Ala Leu Thr Gln Ala Leu Lys Met Ala Glu Gly
1220                1225                1230

Lys Lys Leu Asn Val Tyr Thr Asp Ser Arg Tyr Ala Phe Ala Thr
1235                1240                1245

Ala His Ile His Gly Glu Ile Tyr Arg Arg Arg Gly Leu Leu Thr
1250                1255                1260

Ser Glu Gly Lys Glu Ile Lys Asn Lys Asp Glu Ile Leu Ala Leu
1265                1270                1275

Leu Lys Ala Leu Phe Leu Pro Lys Arg Leu Ser Ile Ile His Cys
1280                1285                1290

Pro Gly His Gln Lys Gly His Ser Ala Glu Ala Arg Gly Asn Arg
1295                1300                1305

Met Ala Asp Gln Ala Ala Arg Lys Ala Ala Ile Thr Glu Thr Pro
1310                1315                1320

Asp Thr Ser Thr Leu Leu Ile Glu Asn Ser Ser Pro Tyr Thr Ser
1325                1330                1335

Glu His Phe His Tyr Thr Val Thr Asp Ile Lys Asp Leu Thr Lys
1340                1345                1350

Leu Gly Ala Ile Tyr Asp Lys Thr Lys Lys Tyr Trp Val Tyr Gln
1355                1360                1365

Gly Lys Pro Val Met Pro Asp Gln Phe Thr Phe Glu Leu Leu Asp
1370                1375                1380

Phe Leu His Gln Leu Thr His His Leu Ser Phe Ser Lys Met Lys Ala
1385                1390                1395

Leu Leu Glu Arg Ser His Ser Pro Tyr Tyr Met Leu Asn Arg Asp
1400                1405                1410

Arg Thr Leu Lys Asn Ile Thr Glu Thr Cys Lys Ala Cys Ala Gln
1415                1420                1425

Val Asn Ala Ser Lys Ser Ala Val Lys Gln Gly Thr Arg Val Arg
1430                1435                1440

Gly His Arg Pro Gly Thr His Trp Glu Ile Asp Phe Thr Glu Ile
1445                1450                1455

Lys Pro Gly Leu Tyr Gly Tyr Lys Tyr Leu Leu Val Phe Ile Asp
1460                1465                1470

Thr Phe Ser Gly Trp Ile Glu Ala Phe Pro Thr Lys Lys Glu Thr
```

|  | 1475 |  |  | 1480 |  |  |  | 1485 |  |  |

Ala Lys Val Val Thr Lys Lys Leu Leu Glu Glu Ile Phe Pro Arg
1490                1495                1500

Phe Gly Met Pro Gln Val Leu Gly Thr Asp Asn Gly Pro Ala Phe
1505                1510                1515

Val Ser Lys Val Ser Gln Thr Val Ala Asp Leu Leu Gly Ile Asp
1520                1525                1530

Trp Lys Leu His Cys Ala Tyr Arg Pro Gln Ser Ser Gly Gln Val
1535                1540                1545

Glu Arg Met Asn Arg Thr Ile Lys Glu Thr Leu Thr Lys Leu Thr
1550                1555                1560

Leu Ala Thr Gly Ser Arg Asp Trp Val Leu Leu Leu Pro Leu Ala
1565                1570                1575

Leu Tyr Arg Ala Arg Asn Thr Pro Gly Pro His Gly Leu Thr Pro
1580                1585                1590

Tyr Glu Ile Leu Tyr Gly Ala Pro Pro Pro Leu Val Asn Phe Pro
1595                1600                1605

Asp Pro Asp Met Thr Arg Val Thr Asn Ser Pro Ser Leu Gln Ala
1610                1615                1620

His Leu Gln Ala Leu Tyr Leu Val Gln His Glu Val Trp Arg Pro
1625                1630                1635

Leu Ala Ala Tyr Gln Glu Gln Leu Asp Arg Pro Val Val Pro
1640                1645                1650

His Pro Tyr Arg Val Gly Asp Thr Val Trp Val Arg Arg His Gln
1655                1660                1665

Thr Lys Asn Leu Glu Pro Arg Trp Lys Gly Pro Tyr Thr Val Leu
1670                1675                1680

Leu Thr Thr Pro Thr Ala Leu Lys Val Asp Gly Ile Ala Ala Trp
1685                1690                1695

Ile His Ala Ala His Val Lys Ala Ala Asp Pro Gly Gly Gly Pro
1700                1705                1710

Ser Ser Arg Leu Thr Trp Arg Val Gln Arg Ser Gln Asn Pro Leu
1715                1720                1725

Lys Ile Arg Leu Thr Arg Glu Ala Pro
1730                1735

<210> SEQ ID NO 38
<211> LENGTH: 43
<212> TYPE: DNA
<213> ORGANISM: Artificial Sequence
<220> FEATURE:
<223> OTHER INFORMATION: Forward Primer Murine Ppgk

<400> SEQUENCE: 38
aattaaacgc gttcgcgaca attctaccgg gtaggggagg cgc            43

<210> SEQ ID NO 39
<211> LENGTH: 35
<212> TYPE: DNA
<213> ORGANISM: Artificial Sequence
<220> FEATURE:
<223> OTHER INFORMATION: Reverse Primer murine Ppgk

<400> SEQUENCE: 39
aattaaatcg atggtggcgg gatgcaggtc gaaag                     35

<210> SEQ ID NO 40
<211> LENGTH: 529

<212> TYPE: DNA
<213> ORGANISM: Mus musculus
<220> FEATURE:
<223> OTHER INFORMATION: Murine Ppgk nucleic acid

<400> SEQUENCE: 40

```
caattctacc gggtagggga ggcgcttttc ccaaggcagt ctggagcatg cgctttagca        60
gccccgctgg gcacttggcg ctacacaagt ggcctctggc ctcgcacaca ttccacatcc       120
accggtaggc gccaaccggc tccgttcttt ggtggcccct tcgcgccacc ttctactcct       180
cccctagtca ggaagtttcc ccccgcccc  gcagctcgcg tcgagcagga cgtgacaaat       240
ggaagtagca cgtctcacta gtctcgtgca gatggacagc accgctgagc aatggaagcg       300
ggtaggcctt tggggcaacg gccaatagca gctttgctcc ttcgctttct gggctcagag       360
gctgggaagg ggtgggtccg ggggcgggct caggggcggg ctcaggggcg gggcgggcgc       420
ccgaaggtcc tccggaggcc cggcattctg cacgcttcaa agcgcacgt  ctgccgcgct       480
gttctcctct tcctcatctc cgggcctttc gacctgcatc ccgccacca                  529
```

<210> SEQ ID NO 41
<211> LENGTH: 1215
<212> TYPE: DNA
<213> ORGANISM: Mus musculus
<220> FEATURE:
<223> OTHER INFORMATION: Vkappa promoter nucleic acid

<400> SEQUENCE: 41

```
agcttttgtg tttgacccctt ccctagccaa aggcaactat ttaaggaccc tttaaaactc       60
ttgaaactac tttagagtca ttaagtaatt taaccacttt taattacttt aaaatgatgt      120
caactcccttt ttaactatta atttatttta agggggggaaa ggctgctcat aattctattg      180
tttttcttgg taaagaactc tcagttttcg tttttactac ctctgtcacc caagagttgg      240
catctcaaca gagggggactt tccgagaggc catctggcag ttgcttaaga tcagaagtga      300
agtctgccag ttcctcccag gcaggtggcc cagattacag ttgacctgtt ctggtgtggc      360
taaaaattgt cccatgtggt tacagaccat tagaccaggg tctgatgaat tgctcagaat      420
gtttctggac acccaaatac agaccctggc ttaaggacct gtccatacag taggtttagc      480
ttggctacac caaaggaagc catagagagg ctaatattag agtattcttg gaagagacag      540
gagaaaatga aagccagttt ctgctcttac cttatgtgct tgtgttcaga ctcccaaaca      600
tcaggagtgt cagataaact ggtctggatc tctgtctgaa gcatggaact gaaaagaatg      660
tagtttcagg gaagaaaggc aatagaggga agcctgagat tatcttcaaa gggtcagact      720
caatttactt tctaaagaag tagctaggaa ctagggaata acttagaaac aacaagatcg      780
tatatatgtg catcctggcc ccattgttcc ttatctgtag ggataagcgt gcttttttgt      840
gtgtctgtct ataacataac tgtttacaca taatacactg aaatggagcc cttccttgtt      900
acttcatacc atcctctgtg cttccttcct cagatcgatc ctggtctaca gtgtgaggta      960
ctggacgacc aagaatagag aaacctgtct caaaaaaatg tatttagaag ggtcccttaa     1020
gacacatgtg atgttctagt aaatttttctg ctaacaccaa cttcctctgg gtgaaacagg     1080
ggcaggtgca catggagaaa cagtacatac tctgctgatt tgcatatgaa ataatttttat    1140
aacagcccag gcttctttaa gggcagctgc caggagccta ataaagcatc ctctcttcca     1200
gctctcagag gatct                                                      1215
```

<210> SEQ ID NO 42
<211> LENGTH: 5021

<212> TYPE: DNA
<213> ORGANISM: Artificial Sequence
<220> FEATURE:
<223> OTHER INFORMATION: pIRES-puro

<400> SEQUENCE: 42

| | | | | | |
|---|---|---|---|---|---|
| gacggatcgg | gagatctccc | gatccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gcttggtacc | 900 |
| gagctcggat | cgatatctgc | ggccgcgtcg | acggaattca | gtggatccac | tagtaacggc | 960 |
| cgccagtgtg | ctggaattaa | ttcgctgtct | gcgaggggca | gctgttgggg | tgagtactcc | 1020 |
| ctctcaaaag | cgggcatgac | ttctgcgcta | agattgtcag | tttccaaaaa | cgaggaggat | 1080 |
| ttgatattca | cctggcccgc | ggtgatgcct | ttgagggtgg | ccgcgtccat | ctggtcagaa | 1140 |
| aagacaatct | ttttgttgtc | aagcttgagg | tgtggcaggc | ttgagatctg | gccatacact | 1200 |
| tgagtgacaa | tgacatccac | tttgcctttc | tctccacagg | tgtccactcc | caggtccaac | 1260 |
| tgcaggtcga | gcatgcatct | agggcggcca | attccgcccc | tctccctccc | cccccctaa | 1320 |
| cgttactggc | cgaagccgct | tggaataagg | ccggtgtgcg | tttgtctata | tgtgattttc | 1380 |
| caccatattg | ccgtcttttg | gcaatgtgag | ggcccggaaa | cctggccctg | tcttcttgac | 1440 |
| gagcattcct | aggggtcttt | cccctctcgc | caaaggaatg | caaggtctgt | tgaatgtcgt | 1500 |
| gaaggaagca | gttcctctgg | aagcttcttg | aagacaaaca | acgtctgtag | cgacccttg | 1560 |
| caggcagcgg | aaccccccac | ctggcgacag | gtgcctctgc | ggccaaaagc | cacgtgtata | 1620 |
| agatacacct | gcaaaggcgg | cacaacccca | gtgccacgtt | gtgagttgga | tagttgtgga | 1680 |
| aagagtcaaa | tggctctcct | caagcgtatt | caacaagggg | ctgaaggatg | cccagaaggt | 1740 |
| accccattgt | atgggatctg | atctggggcc | tcggtgcaca | tgctttacat | gtgtttagtc | 1800 |
| gaggttaaaa | aaacgtctag | gccccccgaa | ccacggggac | gtggttttcc | tttgaaaaac | 1860 |
| acgatgataa | gcttgccaca | acccgggatg | accgagtaca | agcccacggt | gcgcctcgcc | 1920 |
| acccgcgacg | acgtccccag | ggccgtacgc | accctcgccg | ccgcgttcgc | cgactacccc | 1980 |
| gccacgcgcc | acaccgtcga | tccggaccgc | cacatcgagc | gggtcaccga | gctgcaagaa | 2040 |
| ctcttcctca | cgcgcgtcgg | gctcgacatc | ggcaaggtgt | gggtcgcgga | cgacggcgcc | 2100 |
| gcggtggcgt | ctggaccac | gccggagagc | gtcgaagcgg | ggcggtgtt | cgccgagatc | 2160 |
| ggcccgcgca | tggccgagtt | gagcggttcc | cggctggccg | cgcagcaaca | gatggaaggc | 2220 |

| | |
|---|---|
| ctcctggcgc cgcaccggcc caaggagccc gcgtggttcc tggccaccgt cggcgtctcg | 2280 |
| cccgaccacc agggcaaggg tctgggcagc gccgtcgtgc tccccggagt ggaggcggcc | 2340 |
| gagcgcgccg gggtgcccgc cttcctggag acctccgcgc cccgcaacct cccttctac | 2400 |
| gagcggctcg gcttcaccgt caccgccgac gtcgaggtgc ccgaaggacc gcgcacctgg | 2460 |
| tgcatgaccc gcaagcccgg tgcctgactc tagagctcgc tgatcagcct cgactgtgcc | 2520 |
| ttctagttgc cagccatctg ttgtttgccc ctccccgtg ccttccttga ccctggaagg | 2580 |
| tgccactccc actgtccttt cctaataaaa tgaggaaatt gcatcgcatt gtctgagtag | 2640 |
| gtgtcattct attctggggg gtggggtggg gcaggacagc aaggggagg attgggaaga | 2700 |
| caatagcagg catgctgggg atgcggtggg ctctatggct tctgaggcgg aaagaaccag | 2760 |
| ctggggctcg agtgcattct agttgtggtt tgtccaaact catcaatgta tcttatcatg | 2820 |
| tctgtatacc gtcgacctct agctagagct tggcgtaatc atggtcatag ctgtttcctg | 2880 |
| tgtgaaattg ttatccgctc acaattccac acaacatacg agccgaagc ataaagtgta | 2940 |
| aagcctgggg tgcctaatga gtgagctaac tcacattaat tgcgttgcgc tcactgcccg | 3000 |
| ctttccagtc gggaaacctg tcgtgccagc tgcattaatg aatcggccaa cgcgcgggga | 3060 |
| gaggcggttt gcgtattggg cgctcttccg cttcctcgct cactgactcg ctgcgctcgg | 3120 |
| tcgttcggct gcggcgagcg gtatcagctc actcaaaggc ggtaatacgg ttatccacag | 3180 |
| aatcagggga taacgcagga aagaacatgt gagcaaaagg ccagcaaaag gccaggaacc | 3240 |
| gtaaaaaggc cgcgttgctg gcgtttttcc ataggctccg ccccctgac gagcatcaca | 3300 |
| aaaatcgacg ctcaagtcag aggtggcgaa acccgacagg actataaaga taccaggcgt | 3360 |
| ttccccctgg aagctccctc gtgcgctctc ctgttccgac cctgccgctt accggatacc | 3420 |
| tgtccgcctt tctcccttcg ggaagcgtgg cgctttctca atgctcacgc tgtaggtatc | 3480 |
| tcagttcggt gtaggtcgtt cgctccaagc tgggctgtgt gcacgaaccc cccgttcagc | 3540 |
| ccgaccgctg cgccttatcc ggtaactatc gtcttgagtc aacccggta agacacgact | 3600 |
| tatcgccact ggcagcagcc actggtaaca ggattagcag agcgaggtat gtaggcggtg | 3660 |
| ctacagagtt cttgaagtgg tggcctaact acggctacac tagaaggaca gtatttggta | 3720 |
| tctgcgctct gctgaagcca gttaccttcg gaaaaagagt tggtagctct tgatccggca | 3780 |
| aacaaaccac cgctggtagc ggtggttttt tgtttgcaa gcagcagatt acgcgcagaa | 3840 |
| aaaaaggatc tcaagaagat cctttgatct tttctacggg gtctgacgct cagtggaacg | 3900 |
| aaaactcacg ttaagggatt ttggtcatga gattatcaaa aaggatcttc acctagatcc | 3960 |
| ttttaaatta aaaatgaagt tttaaatcaa tctaaagtat atatgagtaa acttggtctg | 4020 |
| acagttacca atgcttaatc agtgaggcac ctatctcagc gatctgtcta tttcgttcat | 4080 |
| ccatagttgc ctgactcccc gtcgtgtaga taactacgat acgggagggc ttaccatctg | 4140 |
| gccccagtgc tgcaatgata ccgcgagacc cacgctcacc ggctccagat ttatcagcaa | 4200 |
| taaaccagcc agccggaagg gccgagcgca gaagtggtcc tgcaacttta tccgcctcca | 4260 |
| tccagtctat taattgttgc cgggaagcta gagtaagtag ttcgccagtt aatagtttgc | 4320 |
| gcaacgttgt tgccattgct acaggcatcg tggtgtcacg ctcgtcgttt ggtatggctt | 4380 |
| cattcagctc cggttcccaa cgatcaaggc gagttacatg atcccccatg ttgtgcaaaa | 4440 |
| aagcggttag ctccttcggt cctccgatcg ttgtcagaag taagttggcc gcagtgttat | 4500 |
| cactcatggt tatggcagca ctgcataatt ctcttactgt catgccatcc gtaagatgct | 4560 |
| tttctgtgac tggtgagtac tcaaccaagt cattctgaga atagtgtatg cggcgaccga | 4620 |

| | |
|---|---|
| gttgctcttg cccggcgtca atacgggata ataccgcgcc acatagcaga actttaaaag | 4680 |
| tgctcatcat tggaaaacgt tcttcggggc gaaaactctc aaggatctta ccgctgttga | 4740 |
| gatccagttc gatgtaaccc actcgtgcac ccaactgatc ttcagcatct tttactttca | 4800 |
| ccagcgtttc tgggtgagca aaaacaggaa ggcaaaatgc cgcaaaaaag gaataagggg | 4860 |
| cgacacggaa atgttgaata ctcatactct tcctttttca atattattga agcatttatc | 4920 |
| agggttattg tctcatgagc ggatacatat ttgaatgtat ttagaaaaat aaacaaatag | 4980 |
| gggttccgcg cacatttccc cgaaaagtgc cacctgacgt c | 5021 |

<210> SEQ ID NO 43
<211> LENGTH: 6231
<212> TYPE: DNA
<213> ORGANISM: Artificial Sequence
<220> FEATURE:
<223> OTHER INFORMATION: MigR1 vector

<400> SEQUENCE: 43

| | |
|---|---|
| agtgaaagac cccacctgta ggtttggcaa gctagcttaa gtaacgccat tttgcaaggc | 60 |
| atggaaaata cataactgag aatagagaag ttcagatcaa ggttaggaac agagagacag | 120 |
| cagaatatgg gccaaacagg atatctgtgg taagcagttc ctgccccggc tcagggccaa | 180 |
| gaacagatgg tccccagatg cggtcccgcc ctcagcagtt tctagagaac catcagatgt | 240 |
| ttccagggtg ccccaaggac ctgaaaatga ccctgtgcct tatttgaact aaccaatcag | 300 |
| ttcgcttctc gcttctgttc gcgcgcttct gctccccgag ctcaataaaa gagcccacaa | 360 |
| cccctcactc ggcgcgccag tcctccgata gactgcgtcg cccgggtacc cgtattccca | 420 |
| ataaagcctc ttgctgtttg catccgaatc gtggactcgc tgatccttgg gagggtctcc | 480 |
| tcagattgat tgactgccca cctcggggt cttttcatttg gaggttccac cgagatttgg | 540 |
| agacccctgc ctagggacca ccgacccccc cgccggagg taagctggcc agcggtcgtt | 600 |
| tcgtgtctgt ctctgtcttt gtgcgtgttt gtgccggcat ctaatgtttg cgcctgcgtc | 660 |
| tgtactagtt agctaactag ctctgtatct ggcggacccg tggtggaact gacgagttct | 720 |
| gaacacccgg ccgcaaccct gggagacgtc ccagggactt gggggccgt ttttgtggcc | 780 |
| cgacctgagg aagggagtcg atgtggaatc cgacccccgtc aggatatgtg gttctggtag | 840 |
| gagacgagaa cctaaaacag ttcccgcctc cgtctgaatt tttgctttcg gtttggaacc | 900 |
| gaagccgcgc gtcttgtctg ctgcagcgct gcagcatcgt tctgtgttgt ctctgtctga | 960 |
| ctgtgtttct gtatttgtct gaaaattagg gccagactgt taccactccc ttaagtttga | 1020 |
| ccttaggtca ctggaaagat gtcgagcgga tcgctcacaa ccagtcggta gatgtcaaga | 1080 |
| agagacgttg ggttaccttc tgctctgcag aatggccaac ctttaacgtc ggatggccgc | 1140 |
| gagacggcac ctttaaccga gacctcatca cccaggttaa gatcaaggtc ttttcacctg | 1200 |
| gcccgcatgg acacccagac caggtcccct acatcgtgac ctgggaagcc ttggcttttg | 1260 |
| accccccctcc ctgggtcaag ccctttgtac accctaagcc tccgcctcct cttcctccat | 1320 |
| ccgccccgtc tctcccccctt gaacctcctc gttcgacccc gcctcgatcc tccctttatc | 1380 |
| cagccctcac tccttctcta ggcgccgaa ttagatctct cgaggttaac gaattccgcc | 1440 |
| cctctccctc ccccccccct aacgttactg gccgaagccg cttggaataa ggccggtgtg | 1500 |
| cgtttgtcta tatgttattt tccaccatat tgccgtcttt tggcaatgtg agggcccgga | 1560 |
| aacctggccc tgtcttcttg acgagcattc ctaggggtct ttcccctctc gccaaaggaa | 1620 |
| tgcaaggtct gttgaatgtc gtgaaggaag cagttcctct ggaagcttct tgaagacaaa | 1680 |

```
caacgtctgt agcgacccct tgcaggcagc ggaaccccc  acctggcgac aggtgcctct  1740
gcggccaaaa gccacgtgta taagatacac ctgcaaaggc ggcacaaccc cagtgccacg  1800
ttgtgagttg gatagttgtg gaaagagtca aatggctctc ctcaagcgta ttcaacaagg  1860
ggctgaagga tgcccagaag gtaccccatt gtatgggatc tgatctgggg cctcggtgca  1920
catgctttac atgtgtttag tcgaggttaa aaaacgtcta ggcccccga  accacgggga   1980 cgtggttttc ctttgaaaaa cacgatgata atatggccac aaccatggtg agcaagggcg  2040
aggagctgtt caccggggtg gtgcccatcc tggtcgagct ggacggcgac gtaaacggcc  2100
acaagttcag cgtgtccggc gagggcgagg gcgatgccac ctacggcaag ctgaccctga  2160
agttcatctg caccaccggc aagctgcccg tgccctggcc caccctcgtg accaccctga  2220
cctacggcgt gcagtgcttc agccgctacc ccgaccacat gaagcagcac gacttcttca  2280
agtccgccat gcccgaaggc tacgtccagg agcgcaccat cttcttcaag gacgacggca  2340
actacaagac ccgcgccgag gtgaagttcg agggcgacac cctggtgaac cgcatcgagc  2400
tgaagggcat cgacttcaag gaggacggca acatcctggg gcacaagctg gagtacaact  2460
acaacagcca caacgtctat atcatggccg acaagcagaa gaacggcatc aaggtgaact  2520
tcaagatccg ccacaacatc gaggacggca gcgtgcagct cgccgaccac taccagcaga  2580
acacccccat cggcgacggc cccgtgctgc tgcccgacaa ccactacctg agcacccagt  2640
ccgccctgag caaagacccc aacgagaagc gcgatcacat ggtcctgctg gagttcgtga  2700
ccgccgccgg gatcactctc ggcatggacg agctgtacaa gtaagtcgac ctgcagccaa  2760
gcttatcgat aaaataaaag attttattta gtctccagaa aagggggga  atgaaagacc  2820 ccacctgtag gtttggcaag ctagcttaag taacgccatt ttgcaaggca tggaaaatac  2880
ataactgaga atagagaagt tcagatcaag gttaggaaca gagagacagc agaatatggg  2940
ccaaacagga tatctgtggt aagcagttcc tgccccggct cagggccaag aacagatggt  3000
ccccagatgc ggtcccgccc tcagcagttt ctagagaacc atcagatgtt tccagggtgc  3060
cccaaggacc tgaaaatgac cctgtgcctt atttgaacta accaatcagt tcgcttctcg  3120
cttctgttcg cgcgcttctg ctccccgagc tcaataaaag agcccacaac ccctcactcg  3180
gcgcgccagt cctccgatag actgcgtcgc ccgggtaccc gtgtatccaa taaaccctct  3240
tgcagttgca tccgacttgt ggtctcgctg ttccttggga gggtctcctc tgagtgattg  3300
actacccgtc agcggggtc  tttcagaatt ggtaatcatg gtcatagctg tttcctgtgt  3360
gaaattgtta tccgctcaca attccacaca acatacgagc cggaagcata agtgtaaag   3420 cctggggtgc ctaatgagtg agctaactca cattaattgc gttgcgctca ctgcccgctt  3480
tccagtcggg aaacctgtcg tgccagctgc attaatgaat cggccaacgc gcggggagag  3540
gcggtttgcg tattgggcgc tcttccgctt cctcgctcac tgactcgctg cgctcggtcg  3600
ttcggctgcg gcgagcggta tcagctcact caaaggcggt aatacggtta tccacagaat  3660
caggggataa cgcaggaaag aacatgtgag caaaaggcca gcaaaggcc  aggaaccgta  3720 aaaaggccgc gttgctggcg ttttccata  ggctccgccc cctgacgag  catcacaaaa  3780 atcgacgctc aagtcagagg tggcgaaacc cgacaggact ataaagatac caggcgtttc  3840
cccctggaag ctccctcgtg cgctctcctg ttccgaccct gccgcttacc ggatacctgt  3900
ccgcctttct cccttcggga agcgtggcgc tttctcatag ctcacgctgt aggtatctca  3960
gttcggtgta ggtcgttcgc tccaagctgg gctgtgtgca cgaaccccc  gttcagcccg  4020 accgctgcgc cttatccggt aactatcgtc ttgagtccaa cccggtaaga cacgacttat  4080
```

```
cgccactggc agcagccact ggtaacagga ttagcagagc gaggtatgta ggcggtgcta    4140
cagagttctt gaagtggtgg cctaactacg gctacactag aaggacagta tttggtatct    4200
gcgctctgct gaagccagtt accttcggaa aaagagttgg tagctcttga tccggcaaac    4260
aaaccaccgc tggtagcggt ggttttttg tttgcaagca gcagattacg cgcagaaaaa     4320
aaggatctca agaagatcct ttgatctttt ctacggggtc tgacgctcag tggaacgaaa    4380
actcacgtta agggattttg gtcatgagat tatcaaaaag gatcttcacc tagatccttt    4440
taaattaaaa atgaagtttt aaatcaatct aaagtatata tgagtaaact tggtctgaca    4500
gttaccaatg cttaatcagt gaggcaccta tctcagcgat ctgtctattt cgttcatcca    4560
tagttgcctg actccccgtc gtgtagataa ctacgatacg ggagggctta ccatctggcc    4620
ccagtgctgc aatgataccg cgagacccac gctcaccggc tccagattta tcagcaataa    4680
accagccagc cggaagggcc gagcgcagaa gtggtcctgc aactttatcc gcctccatcc    4740
agtctattaa ttgttgccgg gaagctagag taagtagttc gccagttaat agtttgcgca    4800
acgttgttgc cattgctaca ggcatcgtgg tgtcacgctc gtcgtttggt atggcttcat    4860
tcagctccgt tcccaacga  tcaaggcgag ttacatgatc ccccatgttg tgcaaaaaag    4920
cggttagctc cttcggtcct ccgatcgttg tcagaagtaa gttggccgca gtgttatcac    4980
tcatggttat ggcagcactg cataattctc ttactgtcat gccatccgta agatgctttt    5040
ctgtgactgg tgagtactca accaagtcat tctgagaata gtgtatgcgg cgaccgagtt    5100
gctcttgccc ggcgtcaata cgggataata ccgcgccaca tagcagaact ttaaaagtgc    5160
tcatcattgg aaaacgttct cggggcgaaa actctcaag  gatcttaccg ctgttgagat    5220
ccagttcgat gtaacccact cgtgcaccca actgatcttc agcatctttt actttcacca    5280
gcgtttctgg gtgagcaaaa acaggaaggc aaaatgccgc aaaaaaggga ataagggcga    5340
cacggaaatg ttgaatactc atactcttcc tttttcaata ttattgaagc atttatcagg    5400
gttattgtct catgagcgga tacatatttg aatgtattta gaaaaataaa caaatagggg    5460
ttccgcgcac atttccccga aaagtgccac ctgacgtcta agaaaccatt attatcatga    5520
cattaaccta taaaaatagg cgtatcacga ggccctttcg tctcgcgcgt ttcggtgatg    5580
acggtgaaaa cctctgacac atgcagctcc cggagacggt cacagcttgt ctgtaagcgg    5640
atgccgggag cagacaagcc cgtcagggcg cgtcagcggg tgttggcggg tgtcggggct    5700
ggcttaacta tgcggcatca gagcagattg tactgagagt gcaccatatg cggtgtgaaa    5760
taccgcacag atgcgtaagg agaaaatacc gcatcaggcg ccattcgcca ttcaggctgc    5820
gcaactgttg ggaagggcga tcggtgcggg cctcttcgct attacgccag ctggcgaaag    5880
ggggatgtgc tgcaaggcga ttaagttggg taacgccagg gttttcccag tcacgacgtt    5940
gtaaaacgac ggccagtgcc acgctctccc ttatgcgact cctgcattag gaagcagccc    6000
agtagtaggt tgaggccgtt gagcaccgcc gccgcaagga tggtgcatg  caaggagatg    6060 gcgcccaaca gtcccccggc cacgggggcct gccaccatac ccacgccgaa acaagcgctc    6120
atgagcccga agtggcgagc ccgatcttcc ccatcggtga tgtcggcgat ataggcgcca    6180
gcaaccgcac ctgtggcgcc ggtgatgccg gccacgatgc gtccggcgta g             6231
```

<210> SEQ ID NO 44
<211> LENGTH: 49
<212> TYPE: DNA
<213> ORGANISM: Artificial Sequence
<220> FEATURE:
<223> OTHER INFORMATION: Forward primer VEGF121

<400> SEQUENCE: 44
aataagcggc cgcgccacca tgaactttct gctgtcttgg gtgcattgg         49

<210> SEQ ID NO 45
<211> LENGTH: 68
<212> TYPE: DNA
<213> ORGANISM: Artificial Sequence
<220> FEATURE:
<223> OTHER INFORMATION: Reverse primer VEGF121

<400> SEQUENCE: 45
ataattgaat tctcaatgat gatgatgatg atgatctccc cgcctcggct tgtcacattt    60
ttcttgtc                                                            68

<210> SEQ ID NO 46
<211> LENGTH: 468
<212> TYPE: DNA
<213> ORGANISM: Homo sapiens
<220> FEATURE:
<223> OTHER INFORMATION: VEGF121-6xHis nucleic acid

<400> SEQUENCE: 46
atgaactttc tgctgtcttg ggtgcattgg agccttgcct tgctgctcta cctccaccat    60
gccaagtggt cccaggctgc acccatggca gaaggaggag ggcagaatca tcacgaagtg   120
gtgaagttca tggatgtcta tcagcgcagc tactgccatc caatcgagac cctggtggac   180
atcttccagg agtaccctga tgagatcgag tacatcttca gccatcctg tgtgcccctg    240
atgcgatgcg ggggctgctg caatgacgag ggcctggagt gtgtgcccac tgaggagtcc   300
aacatcacca tgcagattat gcggatcaaa cctcaccaag gccagcacat aggagagatg   360
agcttcctac agcacaacaa atgtgaatgc agaccaaaga agatagagc aagacaagaa   420
aaatgtgaca gccgaggcg gggagatcat catcatcatc atcattga                 468

<210> SEQ ID NO 47
<211> LENGTH: 155
<212> TYPE: PRT
<213> ORGANISM: Homo sapiens
<220> FEATURE:
<223> OTHER INFORMATION: VEGF121-6xHis amino acid

<400> SEQUENCE: 47

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys

```
                   130                 135                 140
Pro Arg Arg Gly Asp His His His His His
145                 150                 155

<210> SEQ ID NO 48
<211> LENGTH: 478
<212> TYPE: DNA
<213> ORGANISM: Mus musculus
<220> FEATURE:
<223> OTHER INFORMATION: kappa intron enhancer

<400> SEQUENCE: 48
agcttttgtg tttgacccct ccctgccaaa ggcaactatt taaggaccct ttaaaactct    60
tgaaactact ttagagtcat taagttattt aaccacttttt aattacttta aaatgatgtc   120
aattcccttt taactattaa tttattttaa gggggaaaag gctgctcata attctattgt   180
ttttcttggt aaagaactct cagtttctgt tttactacct ctgtcaccca agagttggca   240
tctcaacaga ggggactttc cgagagccat ctggcagttg cttaagatca gaagtgaagt   300
ctgccagttc ctcctaggca ggtggcccag attacagttg acctgttctg gtgtggctaa   360
aaattgtccc atgtggttac aaaccattag accagggtct gatgaattgc tcagaatatt   420
tctggacacc caaatacaga ccctggctta aggcctgtcc atacagtagg tttagctt    478

<210> SEQ ID NO 49
<211> LENGTH: 411
<212> TYPE: DNA
<213> ORGANISM: Homo sapiens
<220> FEATURE:
<223> OTHER INFORMATION: 146B7 Vh nucleic acid

<400> SEQUENCE: 49
atggggtcaa ccgccatcct cgccctcctc ctggctgttc tccaaggagt ctgtgccgag    60
gtgcagctgg tgcagtctgg agcagaggtg aaaaagcccg gggagtctct gaagatctcc   120
tgtaaggttt ctggatactt ctttaccacc tactggatcg gctgggtgcg ccagatgccc   180
gggaaaggcc tggagtatat ggggatcatc tatcctggtg actctgatac cagatacagc   240
ccgtccttcc aaggccaggt caccatctca gccgacaagt ccatcagcac cgcctacctg   300
cagtggagca gcctgaaggc ctcggacacc gccatgtatt actgtgcgag aggggggtaac  360 tggaactgct ttgactactg gggccaggga accctggtca ccgtctccag c            411

<210> SEQ ID NO 50
<211> LENGTH: 137
<212> TYPE: PRT
<213> ORGANISM: Homo sapiens
<220> FEATURE:
<223> OTHER INFORMATION: 146B7 Vh amino acid

<400> SEQUENCE: 50

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Val Ser Gly Tyr Phe Phe
        35                  40                  45

Thr Thr Tyr Trp Ile Gly Trp Val Arg Gln Met Pro Gly Lys Gly Leu
    50                  55                  60

Glu Tyr Met Gly Ile Ile Tyr Pro Gly Asp Ser Asp Thr Arg Tyr Ser
65                  70                  75                  80
```

```
Pro Ser Phe Gln Gly Gln Val Thr Ile Ser Ala Asp Lys Ser Ile Ser
            85                  90                  95

Thr Ala Tyr Leu Gln Trp Ser Ser Leu Lys Ala Ser Asp Thr Ala Met
            100                 105                 110

Tyr Tyr Cys Ala Arg Gly Gly Asn Trp Asn Cys Phe Asp Tyr Trp Gly
        115                 120                 125

Gln Gly Thr Leu Val Thr Val Ser Ser
    130                 135
```

<210> SEQ ID NO 51
<211> LENGTH: 992
<212> TYPE: DNA
<213> ORGANISM: Homo sapiens
<220> FEATURE:
<223> OTHER INFORMATION: sIgH constant region nucleic acid

<400> SEQUENCE: 51

```
cctccaccaa gggcccatcg gtcttccccc tggcaccctc ctccaagagc acctctgggg      60
gcacagcggc cctgggctgc ctggtcaagg actacttccc cgaaccggtg acggtgtcgt     120
ggaactcagg cgccctgacc agcggcgtgc acaccttccc ggctgtccta cagtcctcag     180
gactctactc cctcagcagc gtggtgaccg tgccctccag cagcttgggc acccagacct     240
acatctgcaa cgtgaatcac aagcccagca acaccaaggt ggacaagaaa gttgagccca     300
aatcttgtga caaaactcac acatgcccac cgtgcccagc acctgaactc ctggggggac     360
cgtcagtctt cctcttcccc ccaaaaccca aggacaccct catgatctcc cggacccctg     420
aggtcacatg cgtggtggtg gacgtgagcc acgaagaccc tgaggtcaag ttcaactggt     480
acgtggacgg cgtggaggtg cataatgcca agacaaagcc gcgggaggag cagtacaaca     540
gcacgtaccg ggtggtcagc gtcctcaccg tcctgcacca ggactggctg aatggcaagg     600
agtacaagtg caaggtctcc aacaaagccc tcccagcccc catcgagaaa accatctcca     660
aagccaaagg gcagccccga gaaccacagg tgtacaccct gcccccatcc cgggatgagc     720
tgaccaagaa ccaggtcagc ctgacctgcc tggtcaaagg cttctatccc agcgacatcg     780
ccgtggagtg ggagagcaat gggcagccgg agaacaacta caagaccacg cctcccgtgc     840
tggactccga cggctccttc ttcctctaca gcaagctcac cgtggacaag agcaggtggc     900
agcagggaa cgtcttctca tgctccgtga tgcatgaggc tctgcacaac cactacacgc     960
agaagagcct ctccctgtct ccgggtaaat ga                                    992
```

<210> SEQ ID NO 52
<211> LENGTH: 330
<212> TYPE: PRT
<213> ORGANISM: Homo sapiens
<220> FEATURE:
<223> OTHER INFORMATION: sIgH constant region amino acid

<400> SEQUENCE: 52

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 53
<211> LENGTH: 381
<212> TYPE: DNA
<213> ORGANISM: Homo sapiens
<220> FEATURE:
<223> OTHER INFORMATION: 146B7 Vk nucleic acid

<400> SEQUENCE: 53
atggaagccc cagcgcagct tctcttcctc ctgctactct ggctcccaga taccaccgga     60
gaaattgtgt tgacgcagtc tccaggcacc ctgtctttgt ctccagggga agagccacc    120 ctctcctgca gggccagtca gagtgttagc agcagctact tagcctgta ccagcagaaa    180 cctggccagg ctcccaggct cctcatctat ggtgcatccc gcaggccac tggcatccca    240 gacaggttca gtggcagtgg gtctgggaca gacttcactc tcaccatcag cagactggag    300
cctgaagatt ttgcagtgta ttactgtcag cggtatggta gctcacacac ttttggccag    360
gggaccaagc tggagatcaa g                                              381

<210> SEQ ID NO 54
<211> LENGTH: 127
<212> TYPE: PRT
<213> ORGANISM: Homo sapiens
<220> FEATURE:
<223> OTHER INFORMATION: 146B7 Vk amino acid

<400> SEQUENCE: 54

Met Glu Ala Pro Ala Gln Leu Leu Phe Leu Leu Leu Leu Trp Leu Pro
1               5                   10                  15
Asp Thr Thr Gly Glu Ile Val Leu Thr Gln Ser Pro Gly Thr Leu Ser
            20                  25                  30
Leu Ser Pro Gly Glu Arg Ala Thr Leu Ser Cys Arg Ala Ser Gln Ser
        35                  40                  45
Val Ser Ser Ser Tyr Leu Ala Trp Tyr Gln Gln Lys Pro Gly Gln Ala
    50                  55                  60
Pro Arg Leu Leu Ile Tyr Gly Ala Ser Arg Arg Ala Thr Gly Ile Pro
65                  70                  75                  80
Asp Arg Phe Ser Gly Ser Gly Ser Gly Thr Asp Phe Thr Leu Thr Ile
                85                  90                  95
Ser Arg Leu Glu Pro Glu Asp Phe Ala Val Tyr Tyr Cys Gln Arg Tyr
            100                 105                 110
Gly Ser Ser His Thr Phe Gly Gln Gly Thr Lys Leu Glu Ile Lys
        115                 120                 125

<210> SEQ ID NO 55
<211> LENGTH: 321
<212> TYPE: DNA
<213> ORGANISM: Homo sapiens
<220> FEATURE:
<223> OTHER INFORMATION: kappa constant region nucleic acid

<400> SEQUENCE: 55
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                               321

<210> SEQ ID NO 56
<211> LENGTH: 106
<212> TYPE: PRT
<213> ORGANISM: Homo sapiens
<220> FEATURE:
<223> OTHER INFORMATION: kappa constant region amino acid

<400> SEQUENCE: 56

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 57
<211> LENGTH: 417
<212> TYPE: DNA
<213> ORGANISM: Mus musculus
<220> FEATURE:
<223> OTHER INFORMATION: SK48E26 Vh nucleic acid

<400> SEQUENCE: 57

```
atgaactttg ggctcagatt gattttcctt gtccttactt taaaaggtgt gaagtgtgaa      60
gtgcacctgg tggagtctgg gggaggctta gtgaagcctg agggtccct gaaactctcc     120
tgtgcagcct ctggattcgc tttcagtagc tatgacatgt cttgggttcg ccagactccg     180
gagaagaggc tggactgggt cgcatacatt agtagtggtg gtggtggcac ctactatcca     240
gacactgtga agggccgatt caccatctcc agggacaatg ccaagaacac cctgtacctg     300
caaatgagca gtctgaagtc tgaggacaca gccatgtatc actgtgcaag ggggggggta     360
cgacgagggt acttcgatgt ctggggcgca gggaccacgg tcaccgtctc cagcgct       417
```

<210> SEQ ID NO 58
<211> LENGTH: 139
<212> TYPE: PRT
<213> ORGANISM: Mus musculus
<220> FEATURE:
<223> OTHER INFORMATION: SK48E26 Vh amino acid

<400> SEQUENCE: 58

```
Met Asn Phe Gly Leu Arg Leu Ile Phe Leu Val Leu Thr Leu Lys Gly
1               5                   10                  15
Val Lys Cys Glu Val His Leu Val Glu Ser Gly Gly Gly Leu Val Lys
            20                  25                  30
Pro Gly Gly Ser Leu Lys Leu Ser Cys Ala Ala Ser Gly Phe Ala Phe
        35                  40                  45
Ser Ser Tyr Asp Met Ser Trp Val Arg Gln Thr Pro Glu Lys Arg Leu
    50                  55                  60
Asp Trp Val Ala Tyr Ile Ser Ser Gly Gly Gly Gly Thr Tyr Tyr Pro
65                  70                  75                  80
Asp Thr Val Lys Gly Arg Phe Thr Ile Ser Arg Asp Asn Ala Lys Asn
                85                  90                  95
Thr Leu Tyr Leu Gln Met Ser Ser Leu Lys Ser Glu Asp Thr Ala Met
            100                 105                 110
Tyr His Cys Ala Arg Gly Gly Val Arg Arg Gly Tyr Phe Asp Val Trp
        115                 120                 125
Gly Ala Gly Thr Thr Val Thr Val Ser Ser Ala
    130                 135
```

<210> SEQ ID NO 59
<211> LENGTH: 381
<212> TYPE: DNA
<213> ORGANISM: Mus musculus
<220> FEATURE:
<223> OTHER INFORMATION: SK48E26 Vk nucleic acid

<400> SEQUENCE: 59

```
atgagtgtgc tcactcaggt cctggcgttg ctgctgctgt ggcttacagg tgccagatgt      60
gacatccaga tgactcagtc tccagcctcc ctatctgcat ctgtgggaga aactgtcacc     120
atcacatgtc gagcaagtgg gaatattcac aattatttaa catggtatca gcagaaacag     180
ggaaaatctc ctcagctcct ggtctataat gcaaaaacct tagcagatgg tgtgccgtca     240
aggttcagtg gcagtggatc aggaacacaa tattctctca agatcaacag cctgcagcct     300
```

```
gaagattttg ggagttatta ctgtcaacat ttttggagta ttccgtacac gttcggaggg    360
gggaccaagc tggaaataaa g                                              381

<210> SEQ ID NO 60
<211> LENGTH: 127
<212> TYPE: PRT
<213> ORGANISM: Mus musculus
<220> FEATURE:
<223> OTHER INFORMATION: SK48E26 Vk amino acid

<400> SEQUENCE: 60

Met Ser Val Leu Thr Gln Val Leu Ala Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Thr Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Ile Pro Tyr Thr Phe Gly Gly Gly Thr Lys Leu Glu Ile Lys
        115                 120                 125

<210> SEQ ID NO 61
<211> LENGTH: 42
<212> TYPE: DNA
<213> ORGANISM: Artificial Sequence
<220> FEATURE:
<223> OTHER INFORMATION: Forward primer murine bcl2A

<400> SEQUENCE: 61
attgctagca tggcgcaagc cgggagaaca gggtatgata ac                       42

<210> SEQ ID NO 62
<211> LENGTH: 39
<212> TYPE: DNA
<213> ORGANISM: Artificial Sequence
<220> FEATURE:
<223> OTHER INFORMATION: Reverse primer murine bcl2A

<400> SEQUENCE: 62
cgcacgcgtc acttgtggcc caggtatgca cccagagtg                           39

<210> SEQ ID NO 63
<211> LENGTH: 708
<212> TYPE: DNA
<213> ORGANISM: Mus musculus
<220> FEATURE:
<223> OTHER INFORMATION: bcl2A nucleic acid

<400> SEQUENCE: 63
atggcgcacg ctgggcgaac agggtatgat aaccgggaga tcgtgatgaa gtacatacat    60
tataagctgt cacagagggg ctacgagtgg gatgctggag atgcggacgc ggcgcccctg    120
ggggctgccc ccaccctgg catcttctcc ttcagcctg agagcaaccc aatgcctgct     180
gtgcaccggg acatggctgc caggacgtct cctctcaggc ccctcgttgc caccgctggg    240
```

```
cctgcgctca gccctgtgcc acctgtggtc catctgaccc tccgccgggc tggggatgac    300
ttctctcgtc gctaccgtcg tgacttcgca gagatgtcca gtcagctgca cctgacgccc    360
ttcaccgcga ggggacgctt tgccacggtg gtggaggaac tcttcaggga tggggtgaac    420
tgggggagga ttgtggcctt ctttgagttc ggtgggggtca tgtgtgtgga gagcgtcaac    480
agggagatgt cacccctggt ggacaacatc gccctgtgga tgactgagta cctgaaccgg    540
catctgcaca cctggatcca ggataacgga ggctgggatg cctttgtgga actatatggc    600
cccagcatgc gacctctgtt tgatttctcc tggctgtctc tgaagaccct gctcagcctg    660
gccctggtcg gggcctgcat cactctgggt gcctatctga ccacaag               708

<210> SEQ ID NO 64
<211> LENGTH: 639
<212> TYPE: DNA
<213> ORGANISM: Homo sapiens
<220> FEATURE:
<223> OTHER INFORMATION: IL-6 nucleic acid

<400> SEQUENCE: 64
atgaactcct tctccacaag cgccttcggt ccagttgcct tctccctggg gctgctcctg     60
gtgttgcctg ctgccttccc tgccccagta cccccaggag aagattccaa agatgtagcc    120
gccccacaca gacagccact cacctcttca gaacgaattg acaaacaaat tcggtacatc    180
ctcgacggca tctcagccct gagaaaggag acatgtaaca gagtaacat gtgtgaaagc    240 agcaaagagg cactggcaga aaacaacctg aaccttccaa agatggctga aaagatgga    300 tgcttccaat ctggattcaa tgaggagact tgcctggtga aaatcatcac tggtcttttg    360
gagtttgagg tatacctaga gtacctccag aacagatttg agagtagtga ggaacaagcc    420
agagctgtgc agatgagtac aaaagtcctg atccagttcc tgcagaaaaa ggcaaagaat    480
ctagatgcaa taaccacccc ctgacccaac acaaatgcca gctgctgac gaagctgcag    540 gcacagaacc agtggctgca ggacatgaca actcatctca ttctgcgcag ctttaaggag    600
ttcctgcagt ccagcctgag ggctcttcgg caaatgtag                           639

<210> SEQ ID NO 65
<211> LENGTH: 702
<212> TYPE: DNA
<213> ORGANISM: Homo sapiens
<220> FEATURE:
<223> OTHER INFORMATION: TNFalpha nucleic acid

<400> SEQUENCE: 65
atgagcactg aaagcatgat ccgggacgtg gagctggccg aggaggcgct ccccaagaag     60 acagggggc cccagggctc caggcggtgc ttgttcctca gcctcttctc cttcctgatc    120
gtggcaggcg ccaccacgct cttctgcctg ctgcactttg gagtgatcgg cccccagagg    180
gaagagttcc ccagggacct ctctctaatc agccctctgg cccaggcagt cagatcatct    240
tctcgaaccc cgagtgacaa gcctgtagcc catgttgtag caaacccctca agctgagggg    300 cagctccagt ggctgaaccg ccgggccaat gccctcctgg ccaatggcgt ggagctgaga    360
gataaccagc tggtggtgcc atcagagggc ctgtacctca tctactccca ggtcctcttc    420
aagggccaag gctgcccctc cacccatgtg ctcctcaccc acaccatcag ccgcatcgcc    480
gtctcctacc agaccaaggt caacctcctc tctgccatca agagccctg ccagagggag    540 accccagagg gggctgaggc caagccctgg tatgagccca tctatctggg aggggtcttc    600
cagctggaga agggtgaccg actcagcgct gagatcaatc ggcccgacta tctcgacttt    660
```

```
gccgagtctg ggcaggtcta ctttgggatc attgccctgt ga                702

<210> SEQ ID NO 66
<211> LENGTH: 276
<212> TYPE: DNA
<213> ORGANISM: Homo sapiens
<220> FEATURE:
<223> OTHER INFORMATION: CCL5 nucleic acid

<400> SEQUENCE: 66
atgaaggtct ccgcggcagc cctcgctgtc atcctcattg ctactgccct ctgcgctcct    60
gcatctgcct ccccatattc ctcggacacc acaccctgct gctttgccta cattgcccgc   120
ccactgcccc gtgcccacat caaggagtat ttctacacca gtggcaagtg ctccaaccca   180
gcagtcgtct ttgtcacccg aaagaaccgc caagtgtgtg ccaacccaga gaagaaatgg   240
gttcgggagt acatcaactc tttggagatg agctag                            276
```